US007399474B2

(12) United States Patent
Altboum et al.

(10) Patent No.: US 7,399,474 B2
(45) Date of Patent: Jul. 15, 2008

(54) **ISOLATION AND CHARACTERIZATION OF THE *CSA* OPERON (ETEC-CS4 PILI) AND METHODS OF USING SAME**

(75) Inventors: Zeev Altboum, Ramat Aviv (IL); Myron M. Levine, Columbia, MD (US); Eileen M. Barry, Elkridge, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 11/053,876

(22) Filed: Feb. 10, 2005

(65) Prior Publication Data

US 2005/0136070 A1   Jun. 23, 2005

Related U.S. Application Data

(62) Division of application No. 09/839,894, filed on Apr. 20, 2001, now Pat. No. 6,902,736.

(60) Provisional application No. 60/198,626, filed on Apr. 20, 2000.

(51) Int. Cl.
*A61K 39/108* (2006.01)
(52) U.S. Cl. .................. 424/190.1; 424/257.1
(58) Field of Classification Search ........................ None
See application file for complete search history.

(56) References Cited

U.S. PATENT DOCUMENTS

| 4,946,778 | A | 8/1990 | Ladner et al. |
| 5,417,986 | A | 5/1995 | Reid et al. |
| 5,932,715 | A | 8/1999 | Scott et al. |
| 6,110,898 | A | 8/2000 | Malone et al. |
| 6,187,344 | B1 | 2/2001 | Eljamal et al. |
| 6,190,669 | B1 | 2/2001 | Noriega et al. |

FOREIGN PATENT DOCUMENTS

WO     WO 96 38171     12/1996

OTHER PUBLICATIONS

Greenspan et al. (Nature Biotechnology 7: 936-937, 1999).*
Cruse et al., Illustrated Dict. of Immunology, 2nd ed., CRC Press, 2003, p. 46.*
McGuinness et al. (Mol. Microbiol., 7:505-514, 1993).*
Moudallal et al. (EMBO Journal, 1:1005-1010, 1982.*
Freedman et al, *J. Infect. Disease*, 177:662-667 (1998).
Levine et al, *Infect. Immun.*, 23:729-736 (1979).
Altboum et al, *Infect. Immun.*, 71:1352-1360 (2003).
Cancer WEB Online Medical Dictionary, "Gene Product" (2002).
Scott et al, *Mol. Micro.*, 6(3):293-300 (1992).
Watson et al, Recombinant DNA, Scientific America Books, N.Y. (1992).
Altboum et al, Construction of a Bivalent Shigella-ETEC Vaccine Expressing CS2 and CS3 Pili, Abstract, 99th General Meeting of the American Society for Microbiology, 99:293 (1999).
Altboum et al, Construction of a Bivalent Shigella-ETEC Vaccine Expressing CS4 Pili, Abstract, 100th General Meeting of the American Society for Microbiology, 100:303 (2000).
Koprowski et al, Construction and Analysis of a Shigella Flexneri 2a/CFA/I Vaccine, Abstract, 99th General Meeting of the American Society for Microbiology, 99:293 (1999).
Holger et al, *J. of Bacteriology*, 181(11):3578-3581 (1999).
Hinxton, Database EBI "online", Van Dijk, United Kingdom (May 7, 1996).
Altboum et al, *Infect. Immun.*, 69(5):3150-3158 (2001).
Black et al, *Bulletin of the World Organization*, 59(2):263-268 (1981).
Black, *Reviews of the Infect. Dis.*, 8(2):S131-S135 (1986).
Blomfield et al, *Mol. Microbiology*, 5(6):1447-1457 (1991).
Bolivar et al. *Gene*, 2:95-113 (1977).
Chang et al, *Nature*, 275:617-624 (1978).
Cote et al, *Proc. Natl. Acad. Sci.*, 80:2026-2030 (1983).
deHaan et al, *FEMS Microbiology Letters*, 83:341-346 (1991).
DuPont et al, *New England J. of Med.*, 295(27):1520-1521 (1976).
Duthy et al, *J. of Bacteriology*, 181(18):5847-5851 (1999).
deBoer et al, *Proc. Natl. Acad. Sci.*, 80:21-25 (1983).
Engvall et al, *Meth. Enzymol.*, 70:419-439 (1980).
Felgner et al, *Proc. Natl. Acad. Sci.*, 84:7413-7417 (1987).
Fraley et al, TIBS, 6:77-80 (1981).
Froelich et al, *Mol. Microbiology*, 12(3):387-401 (1994).
Lodish et al, *Mol. Cell Biol.*, Third Ed., pp. 252-254, Scientific American Books, Inc. (1995).
Frolich et al, *Infect. and Immunity*, 63(12):4849-4856 (1995).
Gaastra et al, *Trends in Microbiology*, 4(11):444-452 (1996).
Galen et al, *Infection and Immunity*, 67(12):6424-6433 (1999).
Goeddel et al, *Nature*, 281:544-548 (1979).
Goeddel et al, *Nucleic Acids Research*, 8(18):4057-4075 (1980).
Grewal et al, *Vaccine*, 11(2):221-226 (1993).
Hall et al, *J. of Bacteriology*, 171(11):6372-6374 (1989).
Hamers et al, *Microbiol Pathogenesis*, 6:297-309 (1989).
Hitzeman et al, *J. of Biological Chemistry*, 255(24):12073-12080 (1980).
Holland et al, *Biochemistry*, 17(23):4900-4907 (1978).
Huse et al, *Science*, 246:1275-1281 (1989).
Hyams et al, *The New England Journal of Medicine*, 325(20):1423-1428 (1991).
Jalajakumari et al, *Mol. Microbiology*, 3(12):1685-1695 (1989).
Jaye et al, *Nucleic Acids Res.*, 11(8):2325-2335 (1983).
Jertborn et al, *Vaccine*, 16(2/3):255-260 (1998).
Knutton et al, *Infect. Immun.*, 57(11):3364-3371 (1989).
Kohler et al, *Nature*, 256:495-497 (1975).

(Continued)

*Primary Examiner*—Shanon A. Foley
*Assistant Examiner*—Brian J Gangle

(57) ABSTRACT

Compositions comprising products of the csa operon, an isolated nucleic acid encoding the csa operon or functional fragments thereof, purified polypeptide products of the csa operon or functional fragments thereof, methods of eliciting an immune response to these products, and methods of producing products of the csa operon are disclosed herein.

6 Claims, 4 Drawing Sheets

OTHER PUBLICATIONS

Koprowski et al, *Infect. Immun.*, 68(9):4884-4892 (2000).
Kotloff et al, *Vaccine*, 13(5):495-502 (1995).
Levine et al, *Infect. Immun.*, 44(2):409-420 (1984).
Levine, *J. of Infect. Dis.*, 155(3):377-389 (1987).
Levine, *Journal of Pediatric Gastroenterology and Nutrition*, 31:336-355 (2000).
Manning et al, *Mol. Gen. Genet.*, 200:322-327 (1985).
Mannino et al, *BioTechniques*, 6(7):682-690 (1988).
Maxam et al, *Methods in Enzymology*, 65:499-561 (1980).
McConnell et al, *Infection and Immunity*, 56(8):1974-1980 (1980).
McConnell et al, *FEMS Microbiology Letters*, 61:105-108 (1989).
McConnell et al, *Epidermiol. Infect.*, 106:477-484 (1991).
Merson et al, *The New England Journal of Medicine*, 294(24):1299-1305 (1976).
Riffkin et al, *Gene*, 167:279-283 (1995).
Messing et al, *Nucleic Acids Research*, 9(2):309-321 (1981).
Morrison et al, *Proc. Natl. Acad. Sci.*, 81:6851-6855 (1984).
Neuberger et al, *Nature*, 312:604-608 (1984).
Noriega et al, *Infect. and Immunity*, 64(1)23-27 (1996).
Orlandi et al, *Proc. Natl. Acad. Sci.*, 86:3833-3837 (1989).
Qadri et al, *J. of Clinical Microbiology*, 38(1):27-31 (2000).
Rudin et al, *Microbial Pathogenesis*, 16:131-139 (1994).
Rudin et al, *Microbial Pathogenesis*, 20:35-45 (1996).
Rudin et al, *Epidemiol. Infect.*, 119:391-393 (1997).
Sakellaris et al, *Molecular Microbiology*, 30(4):681-687 (1998).
Sakellaris et al, *PNAS*, 96(22):12828-12832 (1999).
Savalkoul et al, *Microbial Pathogenesis*, 8:91-99 (1990).
Siebenlist et al, *Cell*, 20:269-281 (1980).
Sommerfelt et al, *Microbial Pathogenesis*, 11:297-304 (1991).
Sommerfelt et al, *J. of Clinical Microbiology*, 30(7):1823-1828 (1992).
Sommerfelt et al, *Infect. and Immunity*, 60(9):3799-3806 (1992).
Svennerholm et al, *Infect. and Immunity*, 56(2):523-528 (1988).
Takeda et al, *Nature*, 314:452-454 (1985).
Thomas et al, *J. of General Microbiology*, 131:2319-2326 (1985).
Vaitukaitis et al, *J. Clin. Endocr.*, 33:988-991 (1971).
Viboud et al, *Microbial Pathogenesis*, 21:139-147 (1996).
Wallace et al, *Nucleic Acids Research*, 9:879-895 (1981).
Willshaw et al, *FEMS Microbiology Letters*, 49:473-478 (1988).
Willshaw et al, *FEMS Microbiology Letters*, 68:255-260 (1990).
Willshaw et al, *FEMS Microbiology Letters*, 82:125-130 (1991).
Winter et al, *Nature*, 349:293-299 (1991).
Wolf et al, *Infection and Immunity*, 57(1):164-173 (1989).
Wolf et al, *FEMS Microbiology Letters*, 148:35-42 (1997).
Bowie et al, *Science*, 247(4948):1306-1310 (1990).
Abaza et al, *J. Protein Chem.*, 11(13):433-444 (1992).
Altboum et al. Construction of a bivalent *Shigella*-ETEC vaccine expressing CS2 and CS3 pili. Abstract E-113. Abstracts of the 99th General Meeting of the American Society for Microbiology, May 30, 1999 (available electronically on or about Apr. 25, 1999).
Altboum et al. Construction of bivalent *Shigella*-ETEC vaccine expressing CS4 pili, Abstract E-46. Abstracts of the 100th General Meeting of the American Society for Microbiology, May 21, 2000 (available electronically on or about Apr. 16, 2000).

* cited by examiner

```
              1 .................................................................50
    CsaE   TMNKILFIFT LFFSSVLFTF AVSADKIPGD ESITNIFGP. RDRNESS ................P
    CfaE   .MNKILFIFT LFFSSGFFTF AVSADKNPGS ENMTNTIGP. HDRGGSS ................P
    CotD   .MKKVIFVLS MFLCSQVYGQ SWHTNVEAGS INKTFSIGP. IDRSAAASY ...............P
    CooD   ..MKKIFIFL SIIFSAVVSA GRYPETTVGN LTKSFQAPR. LDRSVQS ................P
    TsaD   MSNIC4KWTSM TAHWSAIINF IRKYVYPARI IAIL114AGAT LPQVADAITV
 Consensus ..nK........f ........ ......Sa .......f r ............ag. i .................ag.- ldr.a.a ...............p 51                                                              100
    CsaE   KHNILNNHIT A .... YSESH TLYDRMT.FL CLSSHNTLNG ACPTSENPSS
    CfaE   IYNILNSYLT A .... YNGSH HLYDRMS.FL CLSSQNTLNG ACPSSDAPGT
    CotD   AHYIFHEBVA G .... YNKDH SLFDRMT.FL CMSSTDASKG ACPTGENSKS
    CooD   IYNIFTNHVA G .... YSLSH SLYDRIV.FL CTSSSNPVNG ACPTIGTSGV
    TsaD   DLNYDKNNVA VITPVWSQEW SVANVLGGWV CRSNRNENEG CEETHLVWW
 Consensus ..ni..nhva .....ys..h sljr-fl C.Ss.#...G ACpt .......

101                                                             150
    CsaE   SSVSGETNIT LQFTEKRSLI KRELQIKGYK QLLFKSVNC. ..PSGLTLNS
    CfaE   ATIDGETNIT LQFTEKRSLI KRELQIKGYK QFLFKNANC. ..pSKLALNS
    CotD   S..QGETNIK LIFTEKKSLA RKTLNLKGYK RFLYESDRCI HYVDKMNLNS
    CooD   Q..YGTTTIT LQFTEKRSLI KRNINIAGNK KPIWENQSC. DFSNIMVLNS
    TsaD.  YAFGAYSXIR LRFREQISHA EITLILLGSV R DAC. TGVINMNA
 Consensus -.g.t.I. L.FtEk.Sla ..U.I.G.k r .............d-C. y .........n$Ns 151 .........................................................200
    CsaE   AHFNCNKNA. ASGASLYLYI PAGELKNLPF GGIWDATLKL RVKRR ... YS
    CfaE   SHFQCNREQ. ASGATLSLYI PAGELNKLPF GGVWNAVLKL NvKRR ... Y
    CotD   HTVKCVGSF. TRGVDFTLYI PQGEIDGLLT GGIWKATLEL RVKRH . YD
    CooD   KSWSCGA.HGN ANGTILNLYI PAGEINKLPF GGIWEATLIL RLSRYGEVSS
    TsaD   AACQW GRSLKLRI PSEELAKIPT SGTWKATLVL DYLQWG. .GD
 Consensus ......c ................G.....l.Lyl P.gEl.klpt gGiW.AtL.L r .............r.g d 201 .........................................................250
    CsaE   ETYGTYTINI TIKLTDK-.G NIQIWLPQF- KSDARVDLNL RPTGGGTYIG
    CfaE   TTYGTYTINI TVNLTDK..G NIQIWLPQF. KSNARVDLNL RPTGGGTYIG
    CotD   YNHGTYKVNI TVDLTDK..G NIQVWTPKF- HSDPRIDLNL RPEGNGKYSG
    CooD   THYGNYTVNI TVDLTDK-.G NIQVWLPGF. HSNPRVDLNL RPIGNYKYSG
    TsaD   DPLGTSTTDI TLNVTDHFAE NAAIYFPQFG TATPRVDLNL HRMNASQMSG
 Consensus --- Gtyt-#l Tv.ITDk..g Niq!w.PqF. s.pR!DLNL rp.g ... ysG 251                                                             300
    CsaE   RNSVDMCFYD       GYSTNSSSLE IRFQDNNPKS DGKFYLRKIN DDTKEIAYTL
    CfaE   RNSVDMCFYD       GYSTMSSSLE IRFQDDNSKS DGKFYLKKIN DDSKELVYTL
    CotD   SNVLEMCLYD       GYSTHSQSIE MRFQDDSQTG NNEYNLIKTG EPLKKLPYKL
    CooD   SNSLDMCFYD       GYSTNSDSMV IKFQDDNPTN SSEEYNLYKIG G.TEKLPYAV
    TsaD   RANLDMCLYD       G.GVKARSLQ MMEGSNKSG TG.FQVIK.S DSADTIDYAV
 Consensus m.l#MC1YD Gyst.s.Sl. mkf#ddn..g                g-%.IiK.. d .... l. Yav 301                                                             350
    CsaE   SLLLAGXSLT PTNGTSLNIA DAASLFTNWN RITAVTMPEI SVPVLCWPGR
    CfaE   SLLLAGKNLT PTNGQALNI. NTASLETNWN RITAVTMPEI SVPVLCWPGR
    CotD   SLLLGGREFY PNNGKAFTIN DTSSLFINWN RIKSVSLPQI SIPVLCWPAR
    CooD   SLI14GEKIFY PVNGQSFTIN DSSVLETNWN RVTAVAMPEV NVPVLCWPAR
    TsaD   SMNYGGRSIP VTRGVEFSLD NVDKAATR. .PVVLPGQ RQAVRCVPVP
 Consensus S$l.ggr............ -- ptnG- ........f.i. # --- l.tnwn r ............V.7$P pVlcwp 351                                                             383
    CsaE   LQLDAK ... V ENPEAGQYMG NINVTFTPSS       QTL
    CfaE   LQLDAK ... V KNPEAGQYMG NIKITFTPSS       QTL
    CotD   LTFMSE ... L NNPEAGEYSG ILNVTFTPSS       SSL
    CooD   LLLNAD ... V NAPDAGQYSG QIYITFTPSV       ENL
    TsaD   LTLTTQPFNI REKRSGEYQG TLTVTMLMGT        QTP
 Consensus Ltl ........................p.aG#Y.G .l-!Tftps. qtl
```

```
               1                                                            60
    CsaB   MKLKKTIGAM ALTTMFVAMS ASAVEKNITV TASVDPTIDI LQADGSSLPT AVELTYSPAA
    CfaA   MKFKKTIGAM ALTTMFVAVS ASAVEKNITV TASVDPAIDL LQADGNALPS VKLAYSPAS
    CooA   MKLKKTIGAM ALATLFATMG ASAVEKTISV TASVDPTVDL LQSDGSALPN VALTYSPAV
    CotA   MKLNKIIGAL VLSSTFVSMG ASAAEKNITV TASVDPTIDL MQSDGTALPS AVNIAYLPGE
    CsuAI  MKLKYTIGAM ALSTIFVAVS ASAVEKNITV TASVDPTIDI,LQANGSALPT AVDLTYLPGA
    CsuA2                                  VDPTIDI LQANGSALPT AVDLTYLPGA
    CsdA                                   VDPKLDL LQADGTSLPD SIALTYSSAS
    CsbA                                   VDPKLDL LQADGTSLPD SIALTYSSAS
 Consensus  mk..k.iga. .1 ... f .... asa.ek.i.v tasVDPtiDl $Qa#GtaLP. a!.ltYspa.

61                                                                     120
    CsaB   SRFENYKIAT KVHTNVINKN VLVKLVNDPK -LTNVLDSTK QLPITVSYGG K-LSTADVTF
    CfaA   KIFESYRVMT QVHTNDATKK VIVKLADTPQ -LTDV LNSTV QMPISVSWGG VLSTTAKEF
    CooA   NNFEAHTINT VVHTNDSDKG VVVKLSADPV -LSNVLNPTL QIPVSVNFAG KPLSTTGITI
    CotA   KRFESARINT QVHTNNKTKG IQIKLTNDNV VMTNLSDPSK TIPLEVSFAG TKLSTAATSI
    CsuAI  KTFENYSVLT QIYTNDPSKG LDVRLVDTPK -LTNILQPTS TIPLTVSWAG RTLSTSAQKI
    CsuA2  KTFENYSVLT QIYTNDPSKG LDVRLVDTPK -LTNILQPTS TIPLTVSWAG KTLSTSAQKJ
    CsdA   NNFEVYSLNT AIHTNDKTKA VVVKLSAPAV -LSNIMKPSS QIPMKVTLGG KTLSTADAEF
    CsbA   NNFEVYSLNT AIHTNDKSKG VVVKLSASPV -LSNIMXPNS QIPMKVTLGG ETLNTTDTEF
 Consensus  ..FE.ys.nT .!hTN#k.Kg v.!kL...pv .$tNi..p.s qiP..Vs.gG tLsT .... f, 121                                                                    179
    CsaB   EPAELNFGTS GVTGVSSSQD LVIGA----T TAQAPSA-NY SGVVSILMTL AS
    CfaA   EAAALGYSAS GVNGVSSSQE LVISA-APKT AGTAPTAGNY SGVVSLVMTL GS
    CooA   DSNDLNFASS GVNYVSSTQK LSIHADATRV TGGALTAGQY QGLVSIILTK ST
    CotA   TADQLNFGAA GVETVSATKE LVINAGSTQQ TN--IVAGNY QGLVSIVLTQ EP
    CsuAI  AVGDLGFGST GTAGVSNSKE LVIGA---TT SGK-PSAGKY QGVVSIVMTQ STN
    CsuA2  AVGDLGFGST GTAGVSNSKE LVIGA---TT SGTAPSAGKY QGVVSIVMTQ STDTAAPVP
    CsdA   AADTLNFGAS GVENVSSVQQ LTIHA --- EA --APPEAGNY QGVISLIMTQ KT
    CsbA   TVDTLNFGTS GVENVSSTQQ LTIHA --- DT QGTAPEAGNY QGIISLIMTQ KT
Consensus-.d.LnFg.s Gve.VSs.q. Lvl.A .... t        g.ap.AGnY qGv!Si!$Tq   t .......
```

Multalin (version 5.4. 1). Consensus symbols: ! is anyone of IV; $ is anyone of LM; % is anyone of FY; # is anyone of NDQEBZ

Fig. 4.

SEQUENCE LISTING

```
<160> NUMBER OF SEQ ID NOS: 40

<210> SEQ ID NO 1
<211> LENGTH: 717
<212> TYPE: DNA
<213> ORGANISM: E. coli
<220> FEATURE:
<221> NAME/KEY: CDS
<222> LOCATION: (1)...(717)

<400> SEQUENCE: 1 atg cat aaa tta ttt tgt tta cta agt tta ctc ata act cca ttt gtt      48
Met His Lys Leu Phe Cys Leu Leu Ser Leu Leu Ile Thr Pro Phe Val
 1               5                  10                  15 gca aat gca aac ttt atg ata tat cca ata tca aaa gat tta aag aat      96
Ala Asn Ala Asn Phe Met Ile Tyr Pro Ile Ser Lys Asp Leu Lys Asn
             20                  25                  30 gga aat agc gag tta att cgt gtt tat tca aaa tca aaa gag ata caa     144
Gly Asn Ser Glu Leu Ile Arg Val Tyr Ser Lys Ser Lys Glu Ile Gln
         35                  40                  45 tat ata aaa ata tat aca aaa aag att att aat ccc ggc aca act gaa     192
Tyr Ile Lys Ile Tyr Thr Lys Lys Ile Ile Asn Pro Gly Thr Thr Glu
     50                  55                  60 gaa cat gaa gtt gat atg ccc aat tgg gat ggt ggg ttt gta gtt act     240
Glu His Glu Val Asp Met Pro Asn Trp Asp Gly Gly Phe Val Val Thr
 65                  70                  75                  80 cct caa aaa gtt att ctt cct gca gga ggg agt aaa tca ata cgt tta     288
Pro Gln Lys Val Ile Leu Pro Ala Gly Gly Ser Lys Ser Ile Arg Leu
                 85                  90                  95 act caa ttt aga ata cca aaa aaa gag gaa att tat aga gta tat ttt     336
Thr Gln Phe Arg Ile Pro Lys Lys Glu Glu Ile Tyr Arg Val Tyr Phe
            100                 105                 110 gag gcg gta aaa cca gat agc aaa gaa aat gta att gat aat aaa aaa     384
Glu Ala Val Lys Pro Asp Ser Lys Glu Asn Val Ile Asp Asn Lys Lys
        115                 120                 125 cta aca aca gag cta tct gtt aat ata att tat gcg gct cta atc aga     432
Leu Thr Thr Glu Leu Ser Val Asn Ile Ile Tyr Ala Ala Leu Ile Arg
    130                 135                 140 tct tta cca agt gaa caa aac ata tca cta aac att tct aga aat gca     480
Ser Leu Pro Ser Glu Gln Asn Ile Ser Leu Asn Ile Ser Arg Asn Ala
145                 150                 155                 160 aga aaa aat ata att att tat aat aat ggg aat gtt aga gca ggt gtt     528
Arg Lys Asn Ile Ile Ile Tyr Asn Asn Gly Asn Val Arg Ala Gly Val
                165                 170                 175 aaa gat att tat ttt tgt aag tca tct aat atc gat gat agc tgt gta     576
Lys Asp Ile Tyr Phe Cys Lys Ser Ser Asn Ile Asp Asp Ser Cys Val
```

```
                180                 185                 190
aaa aaa acg cat aac aag aat ata tat cca gaa aag tca ttt gat acg        624
Lys Lys Thr His Asn Lys Asn Ile Tyr Pro Glu Lys Ser Phe Asp Thr
        195                 200                 205 ctg gtt aat aac aat ttt tct tat gtt ttc att aaa tta aac cat gaa        672
Leu Val Asn Asn Asn Phe Ser Tyr Val Phe Ile Lys Leu Asn His Glu
    210                 215                 220 gac ata gaa aaa gag caa gga cta ata caa tta aaa gtt cct tga            717
Asp Ile Glu Lys Glu Gln Gly Leu Ile Gln Leu Lys Val Pro *
225                 230                 235
```

<210> SEQ ID NO 2
<211> LENGTH: 238
<212> TYPE: PRT
<213> ORGANISM: E. coli

<400> SEQUENCE: 2

```
Met His Lys Leu Phe Cys Leu Leu Ser Leu Leu Ile Thr Pro Phe Val
1               5                   10                  15

Ala Asn Ala Asn Phe Met Ile Tyr Pro Ile Ser Lys Asp Leu Lys Asn
            20                  25                  30

Gly Asn Ser Glu Leu Ile Arg Val Tyr Ser Lys Ser Lys Glu Ile Gln
        35                  40                  45

Tyr Ile Lys Ile Tyr Thr Lys Lys Ile Ile Asn Pro Gly Thr Thr Glu
    50                  55                  60

Glu His Glu Val Asp Met Pro Asn Trp Asp Gly Gly Phe Val Val Thr
65                  70                  75                  80

Pro Gln Lys Val Ile Leu Pro Ala Gly Gly Ser Lys Ser Ile Arg Leu
                85                  90                  95

Thr Gln Phe Arg Ile Pro Lys Lys Glu Ile Tyr Arg Val Tyr Phe
            100                 105                 110

Glu Ala Val Lys Pro Asp Ser Lys Glu Asn Val Ile Asp Asn Lys Lys
        115                 120                 125

Leu Thr Thr Glu Leu Ser Val Asn Ile Ile Tyr Ala Ala Leu Ile Arg
    130                 135                 140

Ser Leu Pro Ser Glu Gln Asn Ile Ser Leu Asn Ile Ser Arg Asn Ala
145                 150                 155                 160

Arg Lys Asn Ile Ile Ile Tyr Asn Asn Gly Asn Val Arg Ala Gly Val
                165                 170                 175

Lys Asp Ile Tyr Phe Cys Lys Ser Ser Asn Ile Asp Asp Ser Cys Val
            180                 185                 190

Lys Lys Thr His Asn Lys Asn Ile Tyr Pro Glu Lys Ser Phe Asp Thr
        195                 200                 205

Leu Val Asn Asn Asn Phe Ser Tyr Val Phe Ile Lys Leu Asn His Glu
    210                 215                 220

Asp Ile Glu Lys Glu Gln Gly Leu Ile Gln Leu Lys Val Pro
225                 230                 235
```

<210> SEQ ID NO 3
<211> LENGTH: 504
<212> TYPE: DNA
<213> ORGANISM: E. coli
<220> FEATURE:
<221> NAME/KEY: CDS
<222> LOCATION: (1)...(504)

<400> SEQUENCE: 3

```
atg aaa tta aaa aaa act att ggt gca atg gca ctg acc aca atg ttt        48
```

```
Met Lys Leu Lys Lys Thr Ile Gly Ala Met Ala Leu Thr Thr Met Phe
 1               5                  10                  15 gta gct atg agt gct tct gca gta gag aaa aat atc act gta aca gct        96
Val Ala Met Ser Ala Ser Ala Val Glu Lys Asn Ile Thr Val Thr Ala
                20                  25                  30 agt gtt gat cct aca att gat att ttg caa gct gat ggt agt agt tta       144
Ser Val Asp Pro Thr Ile Asp Ile Leu Gln Ala Asp Gly Ser Ser Leu
            35                  40                  45 cct act gct gta gaa tta acc tat tca cct gcg gca agt cgt ttt gaa       192
Pro Thr Ala Val Glu Leu Thr Tyr Ser Pro Ala Ala Ser Arg Phe Glu
        50                  55                  60 aat tat aaa atc gca act aaa gtt cat aca aat gtt ata aat aaa aat       240
Asn Tyr Lys Ile Ala Thr Lys Val His Thr Asn Val Ile Asn Lys Asn
    65                  70                  75                  80 gta cta gtt aag ctt gta aat gat cca aaa ctt aca aat gtt ttg gat       288
Val Leu Val Lys Leu Val Asn Asp Pro Lys Leu Thr Asn Val Leu Asp
                85                  90                  95 tct aca aaa caa ctc ccc att act gta tca tat gga gga aag act cta       336
Ser Thr Lys Gln Leu Pro Ile Thr Val Ser Tyr Gly Gly Lys Thr Leu
            100                 105                 110 tca acc gca gat gtg act ttt gaa cct gca gaa tta aat ttt gga acg       384
Ser Thr Ala Asp Val Thr Phe Glu Pro Ala Glu Leu Asn Phe Gly Thr
        115                 120                 125 tca ggt gta act ggt gta tct tct tcc caa gat tta gtg att ggt gcg       432
Ser Gly Val Thr Gly Val Ser Ser Ser Gln Asp Leu Val Ile Gly Ala
    130                 135                 140 act aca gca caa gca cca acg gcg gga aat tat agt ggg gtc gtt tct       480
Thr Thr Ala Gln Ala Pro Thr Ala Gly Asn Tyr Ser Gly Val Val Ser
145                 150                 155                 160 atc tta atg acc tta gca tca taa                                       504
Ile Leu Met Thr Leu Ala Ser  *
                165

<210> SEQ ID NO 4
<211> LENGTH: 167
<212> TYPE: PRT
<213> ORGANISM: E. coli

<400> SEQUENCE: 4

Met Lys Leu Lys Lys Thr Ile Gly Ala Met Ala Leu Thr Thr Met Phe
 1               5                  10                  15

Val Ala Met Ser Ala Ser Ala Val Glu Lys Asn Ile Thr Val Thr Ala
                20                  25                  30

Ser Val Asp Pro Thr Ile Asp Ile Leu Gln Ala Asp Gly Ser Ser Leu
            35                  40                  45

Pro Thr Ala Val Glu Leu Thr Tyr Ser Pro Ala Ala Ser Arg Phe Glu
        50                  55                  60

Asn Tyr Lys Ile Ala Thr Lys Val His Thr Asn Val Ile Asn Lys Asn
 65                 70                  75                  80

Val Leu Val Lys Leu Val Asn Asp Pro Lys Leu Thr Asn Val Leu Asp
                85                  90                  95

Ser Thr Lys Gln Leu Pro Ile Thr Val Ser Tyr Gly Gly Lys Thr Leu
            100                 105                 110

Ser Thr Ala Asp Val Thr Phe Glu Pro Ala Glu Leu Asn Phe Gly Thr
        115                 120                 125

Ser Gly Val Thr Gly Val Ser Ser Ser Gln Asp Leu Val Ile Gly Ala
    130                 135                 140

Thr Thr Ala Gln Ala Pro Thr Ala Gly Asn Tyr Ser Gly Val Val Ser
```

```
                                145                 150                 155                 160
                                Ile Leu Met Thr Leu Ala Ser
                                                165

<210> SEQ ID NO 5
<211> LENGTH: 2604
<212> TYPE: DNA
<213> ORGANISM: E. coli
<220> FEATURE:
<221> NAME/KEY: CDS
<222> LOCATION: (1)...(2604)

<400> SEQUENCE: 5 atg aca aaa aaa aat aca tta tat ata acg atc atc gca atg cta act         48
Met Thr Lys Lys Asn Thr Leu Tyr Ile Thr Ile Ile Ala Met Leu Thr
 1               5                  10                  15 cca tat tca gtt ttt tcc gga gat ata ccc aac tct ttc cgt gat tta         96
Pro Tyr Ser Val Phe Ser Gly Asp Ile Pro Asn Ser Phe Arg Asp Leu
                20                  25                  30 tgg gga gaa caa gat gaa ttt tat gaa gta aaa cta tat gga caa act        144
Trp Gly Glu Gln Asp Glu Phe Tyr Glu Val Lys Leu Tyr Gly Gln Thr
            35                  40                  45 cta gga ata cat cga att aaa aca acc cca aca cat att aag ttt tat        192
Leu Gly Ile His Arg Ile Lys Thr Thr Pro Thr His Ile Lys Phe Tyr
        50                  55                  60 tca ccc gaa agc att tta gat aaa ata aat gta aaa aaa gaa aag gaa        240
Ser Pro Glu Ser Ile Leu Asp Lys Ile Asn Val Lys Lys Glu Lys Glu
 65                  70                  75                  80 aag aaa ttg agt gtt ttg ttc act aat tct ttt tca aga aat ggc aat        288
Lys Lys Leu Ser Val Leu Phe Thr Asn Ser Phe Ser Arg Asn Gly Asn
                 85                  90                  95 atg agt tgt cag ggg aat gct act ata cag tat aac tgc aat tac att        336
Met Ser Cys Gln Gly Asn Ala Thr Ile Gln Tyr Asn Cys Asn Tyr Ile
            100                 105                 110 aaa aca aaa tca gta gat gtc atc gtt gat gat gtt gat aat gtt gtt        384
Lys Thr Lys Ser Val Asp Val Ile Val Asp Asp Val Asp Asn Val Val
        115                 120                 125 aac ctt ttt ata ggt aat gaa ttt ctg gat tct gaa gca cac aat gat        432
Asn Leu Phe Ile Gly Asn Glu Phe Leu Asp Ser Glu Ala His Asn Asp
    130                 135                 140 gaa tat cat caa tta tca cga aat gta aaa aaa gct ttt ata caa agc        480
Glu Tyr His Gln Leu Ser Arg Asn Val Lys Lys Ala Phe Ile Gln Ser
145                 150                 155                 160 cag aca att aat gtc tca gat tct ggg aag tat aaa agt ttg tct gtt        528
Gln Thr Ile Asn Val Ser Asp Ser Gly Lys Tyr Lys Ser Leu Ser Val
                165                 170                 175 tca ggg aat agc gcg ctg ggt att aca gat aca agt tat gct gtc tta        576
Ser Gly Asn Ser Ala Leu Gly Ile Thr Asp Thr Ser Tyr Ala Val Leu
            180                 185                 190 aat tgg tgg atg aat tac aat aaa ttt aat ggt tac agc aac aac gaa        624
Asn Trp Trp Met Asn Tyr Asn Lys Phe Asn Gly Tyr Ser Asn Asn Glu
        195                 200                 205 aga aca atc aat agt ttg tac ttt aga cat gat tta gat aag aga tat        672
Arg Thr Ile Asn Ser Leu Tyr Phe Arg His Asp Leu Asp Lys Arg Tyr
    210                 215                 220 tat tat caa ttt gga cga atg gat cgt aca gat ttg tca caa agt att        720
Tyr Tyr Gln Phe Gly Arg Met Asp Arg Thr Asp Leu Ser Gln Ser Ile
225                 230                 235                 240 agc ggg aac ttt aat ttt aac tta ctt cct tta ccc gat att gat ggt        768
Ser Gly Asn Phe Asn Phe Asn Leu Leu Pro Leu Pro Asp Ile Asp Gly
                245                 250                 255
```

|         |         |         |         |         |         |         |         |         |         |         |         |         |         |         |         |      |
|---------|---------|---------|---------|---------|---------|---------|---------|---------|---------|---------|---------|---------|---------|---------|---------|------|
| ata     | agg     | aca     | gga     | acc     | aca     | caa     | tct     | tat     | atc     | aaa     | aat     | aca     | gat     | aag     | ttt     | 816  |
| Ile     | Arg     | Thr     | Gly     | Thr     | Thr     | Gln     | Ser     | Tyr     | Ile     | Lys     | Asn     | Thr     | Asp     | Lys     | Phe     |      |
|         |         |         | 260     |         |         |         |         | 265     |         |         |         |         | 270     |         |         |      |
| atc     | gca     | tcc     | cct     | gta     | act     | gtt     | atg     | tta     | act     | aat     | ttt     | tcc     | aga     | gtg     | gaa     | 864  |
| Ile     | Ala     | Ser     | Pro     | Val     | Thr     | Val     | Met     | Leu     | Thr     | Asn     | Phe     | Ser     | Arg     | Val     | Glu     |      |
|         |         |         |         | 275     |         |         |         |         | 280     |         |         |         |         | 285     |         |      |
| gct     | ttt     | cgc     | aat     | aat     | caa     | tta     | ttg     | ggc     | gta     | tgg     | tat     | tta     | gat     | tct     | gga     | 912  |
| Ala     | Phe     | Arg     | Asn     | Asn     | Gln     | Leu     | Leu     | Gly     | Val     | Trp     | Tyr     | Leu     | Asp     | Ser     | Gly     |      |
|         | 290     |         |         |         |         | 295     |         |         |         |         | 300     |         |         |         |         |      |
| gta     | aat     | gaa     | tta     | gat     | aca     | gct     | cgt     | tta     | cct     | tat     | ggt     | agt     | tac     | gat     | ctt     | 960  |
| Val     | Asn     | Glu     | Leu     | Asp     | Thr     | Ala     | Arg     | Leu     | Pro     | Tyr     | Gly     | Ser     | Tyr     | Asp     | Leu     |      |
| 305     |         |         |         |         | 310     |         |         |         |         | 315     |         |         |         |         | 320     |      |
| aaa     | tta     | aaa     | att     | ttt     | gaa     | aat     | act     | cag     | tta     | gtt     | cgt     | gaa     | gaa     | ata     | att     | 1008 |
| Lys     | Leu     | Lys     | Ile     | Phe     | Glu     | Asn     | Thr     | Gln     | Leu     | Val     | Arg     | Glu     | Glu     | Ile     | Ile     |      |
|         |         |         |         | 325     |         |         |         |         | 330     |         |         |         |         | 335     |         |      |
| cct     | ttt     | aat     | aaa     | ggg     | aga     | agt     | tct     | att     | ggt     | gat     | atg     | caa     | tgg     | gac     | gtt     | 1056 |
| Pro     | Phe     | Asn     | Lys     | Gly     | Arg     | Ser     | Ser     | Ile     | Gly     | Asp     | Met     | Gln     | Trp     | Asp     | Val     |      |
|         |         |         | 340     |         |         |         |         | 345     |         |         |         |         | 350     |         |         |      |
| ttc     | att     | cag     | gga     | ggg     | aat     | att     | att     | aat     | gac     | aag     | gat     | cgt     | tac     | ata     | gaa     | 1104 |
| Phe     | Ile     | Gln     | Gly     | Gly     | Asn     | Ile     | Ile     | Asn     | Asp     | Lys     | Asp     | Arg     | Tyr     | Ile     | Glu     |      |
|         |         + 355 |         |         |         |         | 360     |         |         |         |         | 365     |         |         |         |         |      |
| aaa     | caa     | aat     | aat     | cat     | aag     | tca     | tca     | gtt     | aat     | gct     | ggg     | cta     | cgt     | tta     | cca     | 1152 |
| Lys     | Gln     | Asn     | Asn     | His     | Lys     | Ser     | Ser     | Val     | Asn     | Ala     | Gly     | Leu     | Arg     | Leu     | Pro     |      |
| 370     |         |         |         |         | 375     |         |         |         |         | 380     |         |         |         |         |         |      |
| att     | acg     | aaa     | aat     | atc     | tct     | gtt     | caa     | caa     | gga     | gca     | tct     | gtt     | ata     | gat     | aat     | 1200 |
| Ile     | Thr     | Lys     | Asn     | Ile     | Ser     | Val     | Gln     | Gln     | Gly     | Ala     | Ser     | Val     | Ile     | Asp     | Asn     |      |
| 385     |         |         |         |         | 390     |         |         |         |         | 395     |         |         |         |         | 400     |      |
| aaa     | aat     | tat     | tat     | gaa     | ggg     | agt     | ctc     | aaa     | tgg     | aat     | tcc     | ggc     | att     | ctg     | tct     | 1248 |
| Lys     | Asn     | Tyr     | Tyr     | Glu     | Gly     | Ser     | Leu     | Lys     | Trp     | Asn     | Ser     | Gly     | Ile     | Leu     | Ser     |      |
|         |         |         |         | 405     |         |         |         |         | 410     |         |         |         |         | 415     |         |      |
| ggc     | tca     | cta     | aat     | agt     | gag     | ttc     | agt     | ttt     | ctt     | tgg     | gga     | gat     | aat     | gca     | aaa     | 1296 |
| Gly     | Ser     | Leu     | Asn     | Ser     | Glu     | Phe     | Ser     | Phe     | Leu     | Trp     | Gly     | Asp     | Asn     | Ala     | Lys     |      |
|         |         |         | 420     |         |         |         |         | 425     |         |         |         |         | 430     |         |         |      |
| ggt     | aat     | tat     | caa     | agt     | atc     | tcg     | tat     | acc     | gat     | gga     | ttt     | agt     | tta     | tca     | ttt     | 1344 |
| Gly     | Asn     | Tyr     | Gln     | Ser     | Ile     | Ser     | Tyr     | Thr     | Asp     | Gly     | Phe     | Ser     | Leu     | Ser     | Phe     |      |
|         |         |         | 435     |         |         |         |         | 440     |         |         |         |         | 445     |         |         |      |
| tat     | cat     | aat     | gat     | aag     | cgg     | gtc     | gat     | aat     | tgt     | gga     | aga     | aat     | tac     | aat     | gct     | 1392 |
| Tyr     | His     | Asn     | Asp     | Lys     | Arg     | Val     | Asp     | Asn     | Cys     | Gly     | Arg     | Asn     | Tyr     | Asn     | Ala     |      |
| 450     |         |         |         |         | 455     |         |         |         |         | 460     |         |         |         |         |         |      |
| ggt     | tgg     | agt     | gga     | tgc     | tac     | gaa     | tca     | tat     | tcg     | gca     | tct     | tta     | agt     | att     | cct     | 1440 |
| Gly     | Trp     | Ser     | Gly     | Cys     | Tyr     | Glu     | Ser     | Tyr     | Ser     | Ala     | Ser     | Leu     | Ser     | Ile     | Pro     |      |
| 465     |         |         |         | 470     |         |         |         |         | 475     |         |         |         |         | 480     |         |      |
| tta     | ttg     | gga     | tgg     | aca     | agt     | act     | ctg     | gga     | tat     | agt     | gac     | act     | tat     | agt     | gaa     | 1488 |
| Leu     | Leu     | Gly     | Trp     | Thr     | Ser     | Thr     | Leu     | Gly     | Tyr     | Ser     | Asp     | Thr     | Tyr     | Ser     | Glu     |      |
|         |         |         |         | 485     |         |         |         |         | 490     |         |         |         |         | 495     |         |      |
| tca     | gtt     | tat     | aaa     | aac     | cat     | att     | ctt     | tct     | gaa     | tat     | ggt     | ttt     | tat     | aat     | caa     | 1536 |
| Ser     | Val     | Tyr     | Lys     | Asn     | His     | Ile     | Leu     | Ser     | Glu     | Tyr     | Gly     | Phe     | Tyr     | Asn     | Gln     |      |
|         |         |         | 500     |         |         |         |         | 505     |         |         |         |         | 510     |         |         |      |
| aac     | ata     | tat     | aaa     | ggg     | aga     | acc     | caa     | aga     | tgg     | caa     | ctg     | act     | tcg     | tcc     | acc     | 1584 |
| Asn     | Ile     | Tyr     | Lys     | Gly     | Arg     | Thr     | Gln     | Arg     | Trp     | Gln     | Leu     | Thr     | Ser     | Ser     | Thr     |      |
|         |         | 515     |         |         |         |         | 520     |         |         |         |         | 525     |         |         |         |      |
| tct     | tta     | aaa     | tgg     | atg     | gat     | tat     | aat     | ttt     | atg     | cca     | gca     | att     | gga     | ata     | tat     | 1632 |
| Ser     | Leu     | Lys     | Trp     | Met     | Asp     | Tyr     | Asn     | Phe     | Met     | Pro     | Ala     | Ile     | Gly     | Ile     | Tyr     |      |
|         |         | 530     |         |         |         |         | 535     |         |         |         |         | 540     |         |         |         |      |
| aac     | agt     | gag     | caa     | aga     | caa     | ctg     | act     | gat     | aaa     | ggc     | gga     | tat     | ata     | tct     | gta     | 1680 |
| Asn     | Ser     | Glu     | Gln     | Arg     | Gln     | Leu     | Thr     | Asp     | Lys     | Gly     | Gly     | Tyr     | Ile     | Ser     | Val     |      |
| 545     |         |         |         |         | 550     |         |         |         |         | 555     |         |         |         |         | 560     |      |
| act     | ctc     | acc     | cga     | gcc     | agc     | aga     | gaa     | aat     | tca     | tta     | aac     | gca     | ggg     | tat     | tct     | 1728 |
| Thr     | Leu     | Thr     | Arg     | Ala     | Ser     | Arg     | Glu     | Asn     | Ser     | Leu     | Asn     | Ala     | Gly     | Tyr     | Ser     |      |

-continued

```
                565                 570                 575
tac aac tat tcc aga gga aag tat tct tct aac gaa tta ttt gtt gat      1776
Tyr Asn Tyr Ser Arg Gly Lys Tyr Ser Ser Asn Glu Leu Phe Val Asp
        580                 585                 590 gga tat atg aca tca aca aat aat ggt gac tat cat gag gta aga atg      1824
Gly Tyr Met Thr Ser Thr Asn Asn Gly Asp Tyr His Glu Val Arg Met
            595                 600                 605 cgt ttt aat aaa aat aga cat aat gca gaa ggt aga ctt tca ggt cgt      1872
Arg Phe Asn Lys Asn Arg His Asn Ala Glu Gly Arg Leu Ser Gly Arg
        610                 615                 620 ata aac aat cga ttt gga gat tta aat ggt tca ttc agc atg aat aaa      1920
Ile Asn Asn Arg Phe Gly Asp Leu Asn Gly Ser Phe Ser Met Asn Lys
625                 630                 635                 640 aac aga aac acc aac agt agc aat cat tct ctc act ggt ggt tat aat      1968
Asn Arg Asn Thr Asn Ser Ser Asn His Ser Leu Thr Gly Gly Tyr Asn
                645                 650                 655 tcc tca ttt gct ctt aca agt gat gga ttt tac tgg gga gga agt gca      2016
Ser Ser Phe Ala Leu Thr Ser Asp Gly Phe Tyr Trp Gly Gly Ser Ala
            660                 665                 670 tct ggt ttg aca aaa cta gct ggc ggt att atc aag gtt aaa tca aac      2064
Ser Gly Leu Thr Lys Leu Ala Gly Gly Ile Ile Lys Val Lys Ser Asn
        675                 680                 685 gat act aaa aaa aat ctg gta aaa gtg act ggg gca ttg tac ggt gat      2112
Asp Thr Lys Lys Asn Leu Val Lys Val Thr Gly Ala Leu Tyr Gly Asp
    690                 695                 700 tat tcg cta ggg agc aac gat aat gct ttt att cct gta cca gca tta      2160
Tyr Ser Leu Gly Ser Asn Asp Asn Ala Phe Ile Pro Val Pro Ala Leu
705                 710                 715                 720 act cca gcc agt tta att att gaa gat aat aat tat ggt gac aag aat      2208
Thr Pro Ala Ser Leu Ile Ile Glu Asp Asn Asn Tyr Gly Asp Lys Asn
                725                 730                 735 att tct gta ctt gca cca acg aac aac gat atg ttt ata ttg ccg ggt      2256
Ile Ser Val Leu Ala Pro Thr Asn Asn Asp Met Phe Ile Leu Pro Gly
            740                 745                 750 aat gtt tat cct gtt gaa att gaa acc aaa gta agt gtt tct tat att      2304
Asn Val Tyr Pro Val Glu Ile Glu Thr Lys Val Ser Val Ser Tyr Ile
        755                 760                 765 ggt aga ggt ttt gac aaa aac ggc acg cca ctt tct ggc gca cat gtt      2352
Gly Arg Gly Phe Asp Lys Asn Gly Thr Pro Leu Ser Gly Ala His Val
    770                 775                 780 ttg aat gaa cca cat gtt atc ctg gat gag gac ggt gga ttt tcg ttt      2400
Leu Asn Glu Pro His Val Ile Leu Asp Glu Asp Gly Gly Phe Ser Phe
785                 790                 795                 800 gaa tat aca ggt aat gag aaa aca ctt ttt tta tta aag ggc aga act      2448
Glu Tyr Thr Gly Asn Glu Lys Thr Leu Phe Leu Leu Lys Gly Arg Thr
                805                 810                 815 att tat aca tgt caa ctg ggg aaa aat aaa gtt cac aaa ggc att gtt      2496
Ile Tyr Thr Cys Gln Leu Gly Lys Asn Lys Val His Lys Gly Ile Val
            820                 825                 830 ttc gtc gga gat gtt ata tgt gat gtt aat agc aca agt tcc tta cca      2544
Phe Val Gly Asp Val Ile Cys Asp Val Asn Ser Thr Ser Ser Leu Pro
        835                 840                 845 gat gaa ttt gta aag aac cca cgt gtg cag gat ttg ctg gca aag aat      2592
Asp Glu Phe Val Lys Asn Pro Arg Val Gln Asp Leu Leu Ala Lys Asn
    850                 855                 860 gat aaa gga taa                                                      2604
Asp Lys Gly  *
865
```

<210> SEQ ID NO 6
<211> LENGTH: 867
<212> TYPE: PRT
<213> ORGANISM: E. coli

<400> SEQUENCE: 6

```
Met Thr Lys Lys Asn Thr Leu Tyr Ile Thr Ile Ala Met Leu Thr
 1               5                  10                  15

Pro Tyr Ser Val Phe Ser Gly Asp Ile Pro Asn Ser Phe Arg Asp Leu
                20                  25                  30

Trp Gly Glu Gln Asp Glu Phe Tyr Glu Val Lys Leu Tyr Gly Gln Thr
            35                  40                  45

Leu Gly Ile His Arg Ile Lys Thr Thr Pro Thr His Ile Lys Phe Tyr
 50                  55                  60

Ser Pro Glu Ser Ile Leu Asp Lys Ile Asn Val Lys Lys Glu Lys Glu
 65                  70                  75                  80

Lys Lys Leu Ser Val Leu Phe Thr Asn Ser Phe Ser Arg Asn Gly Asn
                85                  90                  95

Met Ser Cys Gln Gly Asn Ala Thr Ile Gln Tyr Asn Cys Asn Tyr Ile
               100                 105                 110

Lys Thr Lys Ser Val Asp Val Ile Val Asp Asp Val Asp Asn Val Val
           115                 120                 125

Asn Leu Phe Ile Gly Asn Glu Phe Leu Asp Ser Glu Ala His Asn Asp
       130                 135                 140

Glu Tyr His Gln Leu Ser Arg Asn Val Lys Lys Ala Phe Ile Gln Ser
145                 150                 155                 160

Gln Thr Ile Asn Val Ser Asp Ser Gly Lys Tyr Lys Ser Leu Ser Val
               165                 170                 175

Ser Gly Asn Ser Ala Leu Gly Ile Thr Asp Thr Ser Tyr Ala Val Leu
           180                 185                 190

Asn Trp Trp Met Asn Tyr Asn Lys Phe Asn Gly Tyr Ser Asn Asn Glu
       195                 200                 205

Arg Thr Ile Asn Ser Leu Tyr Phe Arg His Asp Leu Asp Lys Arg Tyr
   210                 215                 220

Tyr Tyr Gln Phe Gly Arg Met Asp Arg Thr Asp Leu Ser Gln Ser Ile
225                 230                 235                 240

Ser Gly Asn Phe Asn Phe Asn Leu Leu Pro Leu Pro Asp Ile Asp Gly
               245                 250                 255

Ile Arg Thr Gly Thr Thr Gln Ser Tyr Ile Lys Asn Thr Asp Lys Phe
           260                 265                 270

Ile Ala Ser Pro Val Thr Val Met Leu Thr Asn Phe Ser Arg Val Glu
       275                 280                 285

Ala Phe Arg Asn Asn Gln Leu Leu Gly Val Trp Tyr Leu Asp Ser Gly
   290                 295                 300

Val Asn Glu Leu Asp Thr Ala Arg Leu Pro Tyr Gly Ser Tyr Asp Leu
305                 310                 315                 320

Lys Leu Lys Ile Phe Glu Asn Thr Gln Leu Val Arg Glu Glu Ile Ile
               325                 330                 335

Pro Phe Asn Lys Gly Arg Ser Ser Ile Gly Asp Met Gln Trp Asp Val
           340                 345                 350

Phe Ile Gln Gly Gly Asn Ile Ile Asn Asp Lys Asp Arg Tyr Ile Glu
       355                 360                 365

Lys Gln Asn Asn His Lys Ser Ser Val Asn Ala Gly Leu Arg Leu Pro
   370                 375                 380
```

-continued

```
Ile Thr Lys Asn Ile Ser Val Gln Gln Gly Ala Ser Val Ile Asp Asn
385                 390                 395                 400

Lys Asn Tyr Tyr Glu Gly Ser Leu Lys Trp Asn Ser Gly Ile Leu Ser
            405                 410                 415

Gly Ser Leu Asn Ser Glu Phe Ser Phe Leu Trp Gly Asp Asn Ala Lys
        420                 425                 430

Gly Asn Tyr Gln Ser Ile Ser Tyr Thr Asp Gly Phe Ser Leu Ser Phe
    435                 440                 445

Tyr His Asn Asp Lys Arg Val Asp Asn Cys Gly Arg Asn Tyr Asn Ala
450                 455                 460

Gly Trp Ser Gly Cys Tyr Glu Ser Tyr Ser Ala Ser Leu Ser Ile Pro
465                 470                 475                 480

Leu Leu Gly Trp Thr Ser Thr Leu Gly Tyr Ser Asp Thr Tyr Ser Glu
            485                 490                 495

Ser Val Tyr Lys Asn His Ile Leu Ser Glu Tyr Gly Phe Tyr Asn Gln
        500                 505                 510

Asn Ile Tyr Lys Gly Arg Thr Gln Arg Trp Gln Leu Thr Ser Ser Thr
    515                 520                 525

Ser Leu Lys Trp Met Asp Tyr Asn Phe Met Pro Ala Ile Gly Ile Tyr
530                 535                 540

Asn Ser Glu Gln Arg Gln Leu Thr Asp Lys Gly Gly Tyr Ile Ser Val
545                 550                 555                 560

Thr Leu Thr Arg Ala Ser Arg Glu Asn Ser Leu Asn Ala Gly Tyr Ser
            565                 570                 575

Tyr Asn Tyr Ser Arg Gly Lys Tyr Ser Ser Asn Glu Leu Phe Val Asp
        580                 585                 590

Gly Tyr Met Thr Ser Thr Asn Asn Gly Asp Tyr His Glu Val Arg Met
    595                 600                 605

Arg Phe Asn Lys Asn Arg His Asn Ala Glu Gly Arg Leu Ser Gly Arg
610                 615                 620

Ile Asn Asn Arg Phe Gly Asp Leu Asn Gly Ser Phe Ser Met Asn Lys
625                 630                 635                 640

Asn Arg Asn Thr Asn Ser Ser Asn His Ser Leu Thr Gly Gly Tyr Asn
            645                 650                 655

Ser Ser Phe Ala Leu Thr Ser Asp Gly Phe Tyr Trp Gly Gly Ser Ala
        660                 665                 670

Ser Gly Leu Thr Lys Leu Ala Gly Gly Ile Ile Lys Val Lys Ser Asn
    675                 680                 685

Asp Thr Lys Lys Asn Leu Val Lys Val Thr Gly Ala Leu Tyr Gly Asp
690                 695                 700

Tyr Ser Leu Gly Ser Asn Asp Asn Ala Phe Ile Pro Val Pro Ala Leu
705                 710                 715                 720

Thr Pro Ala Ser Leu Ile Ile Glu Asp Asn Asn Tyr Gly Asp Lys Asn
            725                 730                 735

Ile Ser Val Leu Ala Pro Thr Asn Asn Asp Met Phe Ile Leu Pro Gly
        740                 745                 750

Asn Val Tyr Pro Val Glu Ile Glu Thr Lys Val Ser Val Ser Tyr Ile
    755                 760                 765

Gly Arg Gly Phe Asp Lys Asn Gly Thr Pro Leu Ser Gly Ala His Val
770                 775                 780

Leu Asn Glu Pro His Val Ile Leu Asp Glu Asp Gly Gly Phe Ser Phe
785                 790                 795                 800

Glu Tyr Thr Gly Asn Glu Lys Thr Leu Phe Leu Leu Lys Gly Arg Thr
```

```
                      805                 810                 815
Ile Tyr Thr Cys Gln Leu Gly Lys Asn Lys Val His Lys Gly Ile Val
            820                 825                 830

Phe Val Gly Asp Val Ile Cys Asp Val Asn Ser Thr Ser Ser Leu Pro
            835                 840                 845

Asp Glu Phe Val Lys Asn Pro Arg Val Gln Asp Leu Leu Ala Lys Asn
            850                 855                 860

Asp Lys Gly
865

<210> SEQ ID NO 7
<211> LENGTH: 330
<212> TYPE: DNA
<213> ORGANISM: E. coli
<220> FEATURE:
<221> NAME/KEY: CDS
<222> LOCATION: (1)...(330)

<400> SEQUENCE: 7 atc agt aag ttg gca gca tca cct gta ttt ctt gaa aga ggg gtg aat        48
Ile Ser Lys Leu Ala Ala Ser Pro Val Phe Leu Glu Arg Gly Val Asn
 1               5                  10                  15 ata tct gta aga ata cag aag caa att tta tca gaa aaa cca tat gtt        96
Ile Ser Val Arg Ile Gln Lys Gln Ile Leu Ser Glu Lys Pro Tyr Val
            20                  25                  30 gca ttc aga ttg aac gga gac ata cta aga cat tta aag gat gca ttg       144
Ala Phe Arg Leu Asn Gly Asp Ile Leu Arg His Leu Lys Asp Ala Leu
        35                  40                  45 atg ata ata tat ggt atg tca aaa ata gat acc aat gat tgt aga aat       192
Met Ile Ile Tyr Gly Met Ser Lys Ile Asp Thr Asn Asp Cys Arg Asn
    50                  55                  60 atg tca agg aaa ata atg aaa aca gaa gtg gat aaa acc tta ctg gat       240
Met Ser Arg Lys Ile Met Lys Thr Glu Val Asp Lys Thr Leu Leu Asp
65                  70                  75                  80 gta tta aaa aat ata aat agc tat gat gac tca gct ttt ata tct aat       288
Val Leu Lys Asn Ile Asn Ser Tyr Asp Asp Ser Ala Phe Ile Ser Asn
                85                  90                  95 ttg ata tat tta att tca aag atc gag aat aat aaa aaa taa              330
Leu Ile Tyr Leu Ile Ser Lys Ile Glu Asn Asn Lys Lys *
            100                 105

<210> SEQ ID NO 8
<211> LENGTH: 109
<212> TYPE: PRT
<213> ORGANISM: E. coli

<400> SEQUENCE: 8

Ile Ser Lys Leu Ala Ala Ser Pro Val Phe Leu Glu Arg Gly Val Asn
 1               5                  10                  15

Ile Ser Val Arg Ile Gln Lys Gln Ile Leu Ser Glu Lys Pro Tyr Val
            20                  25                  30

Ala Phe Arg Leu Asn Gly Asp Ile Leu Arg His Leu Lys Asp Ala Leu
        35                  40                  45

Met Ile Ile Tyr Gly Met Ser Lys Ile Asp Thr Asn Asp Cys Arg Asn
    50                  55                  60

Met Ser Arg Lys Ile Met Lys Thr Glu Val Asp Lys Thr Leu Leu Asp
65                  70                  75                  80

Val Leu Lys Asn Ile Asn Ser Tyr Asp Asp Ser Ala Phe Ile Ser Asn
                85                  90                  95
```

Leu Ile Tyr Leu Ile Ser Lys Ile Glu Asn Asn Lys Lys
            100                 105

<210> SEQ ID NO 9
<211> LENGTH: 1086
<212> TYPE: DNA
<213> ORGANISM: E. coli
<220> FEATURE:
<221> NAME/KEY: CDS
<222> LOCATION: (1)...(1086)

<400> SEQUENCE: 9

| | | | | | | | | | | | | | | | |
|---|---|---|---|---|---|---|---|---|---|---|---|---|---|---|---|
| atg | aat | aag | att | tta | ttt | att | ttt | aca | ttg | ttt | ttc | tct | tca | gta | ctt | 48 |
| Met | Asn | Lys | Ile | Leu | Phe | Ile | Phe | Thr | Leu | Phe | Phe | Ser | Ser | Val | Leu | |
| 1 | | | | 5 | | | | | 10 | | | | | 15 | | | ttt aca ttt gct gta tcg gca gat aaa att ccc gga gat gaa agc ata    96
Phe Thr Phe Ala Val Ser Ala Asp Lys Ile Pro Gly Asp Glu Ser Ile
            20                  25                  30 act aat att ttt ggc ccg cgt gac agg aac gaa tct tcc ccc aaa cat   144
Thr Asn Ile Phe Gly Pro Arg Asp Arg Asn Glu Ser Ser Pro Lys His
        35                  40                  45 aat ata tta aat aac cat att aca gca tac agt gaa agt cat act ctg   192
Asn Ile Leu Asn Asn His Ile Thr Ala Tyr Ser Glu Ser His Thr Leu
    50                  55                  60 tat gat agg atg act ttt tta tgt ttg tct tct cac aat aca ctt aat   240
Tyr Asp Arg Met Thr Phe Leu Cys Leu Ser Ser His Asn Thr Leu Asn
65                  70                  75                  80 gga gca tgt cca acc agt gag aat cct agc agt tca tcg gtc agc ggt   288
Gly Ala Cys Pro Thr Ser Glu Asn Pro Ser Ser Ser Val Ser Gly
                85                  90                  95 gaa aca aat ata aca tta caa ttt acg gaa aaa aga agt tta ata aaa   336
Glu Thr Asn Ile Thr Leu Gln Phe Thr Glu Lys Arg Ser Leu Ile Lys
            100                 105                 110 aga gag cta caa att aaa ggc tat aaa caa tta ttg ttc aaa agt gtt   384
Arg Glu Leu Gln Ile Lys Gly Tyr Lys Gln Leu Leu Phe Lys Ser Val
        115                 120                 125 aac tgc cca tcc ggc cta aca ctt aac tca gct cat ttt aac tgt aat   432
Asn Cys Pro Ser Gly Leu Thr Leu Asn Ser Ala His Phe Asn Cys Asn
    130                 135                 140 aaa aac gcg gct tca ggt gca agt tta tat tta tat att cct gct ggc   480
Lys Asn Ala Ala Ser Gly Ala Ser Leu Tyr Leu Tyr Ile Pro Ala Gly
145                 150                 155                 160 gaa cta aaa aat ttg cct ttt ggt ggt atc tgg gat gct act ctg aag   528
Glu Leu Lys Asn Leu Pro Phe Gly Gly Ile Trp Asp Ala Thr Leu Lys
                165                 170                 175 tta aga gta aaa aga cga tat agt gag acc tat gga act tac act ata   576
Leu Arg Val Lys Arg Arg Tyr Ser Glu Thr Tyr Gly Thr Tyr Thr Ile
            180                 185                 190 aat atc act att aaa tta act gat aag gga aat att cag ata tgg tta   624
Asn Ile Thr Ile Lys Leu Thr Asp Lys Gly Asn Ile Gln Ile Trp Leu
        195                 200                 205 cct cag ttc aaa agt gac gct cgc gtc gat ctt aac ttg cgt cca act   672
Pro Gln Phe Lys Ser Asp Ala Arg Val Asp Leu Asn Leu Arg Pro Thr
    210                 215                 220 ggt ggg ggc aca tat att gga aga aat tct gtt gat atg tgc ttt tat   720
Gly Gly Gly Thr Tyr Ile Gly Arg Asn Ser Val Asp Met Cys Phe Tyr
225                 230                 235                 240 gat gga tat agt act aac agc agc tct ttg gag ata aga ttt cag gat   768
Asp Gly Tyr Ser Thr Asn Ser Ser Ser Leu Glu Ile Arg Phe Gln Asp
                245                 250                 255 aac aat cct aaa tct gat ggg aaa ttt tat cta agg aaa ata aat gat   816
Asn Asn Pro Lys Ser Asp Gly Lys Phe Tyr Leu Arg Lys Ile Asn Asp -continued

```
Asn Asn Pro Lys Ser Asp Gly Lys Phe Tyr Leu Arg Lys Ile Asn Asp
            260                 265                 270 gac acc aaa gaa att gca tat act ttg tca ctt ctc ttg gcg ggt aaa       864
Asp Thr Lys Glu Ile Ala Tyr Thr Leu Ser Leu Leu Leu Ala Gly Lys
        275                 280                 285 agt tta act cca aca aat gga acg tca tta aat att gct gac gca gct       912
Ser Leu Thr Pro Thr Asn Gly Thr Ser Leu Asn Ile Ala Asp Ala Ala
    290                 295                 300 tct ctg gaa aca aac tgg aat aga att aca gct gtc acc atg cca gaa       960
Ser Leu Glu Thr Asn Trp Asn Arg Ile Thr Ala Val Thr Met Pro Glu
305                 310                 315                 320 atc agt gtt ccg gtg ttg tgt tgg cct gga cgt ttg caa ttg gat gca      1008
Ile Ser Val Pro Val Leu Cys Trp Pro Gly Arg Leu Gln Leu Asp Ala
                325                 330                 335 aaa gtg gaa aat ccc gag gct gga caa tat atg ggt aat att aat gtt      1056
Lys Val Glu Asn Pro Glu Ala Gly Gln Tyr Met Gly Asn Ile Asn Val
            340                 345                 350 act ttc aca cca agt agt caa aca ctc tag                              1086
Thr Phe Thr Pro Ser Ser Gln Thr Leu *
        355                 360
```

<210> SEQ ID NO 10
<211> LENGTH: 361
<212> TYPE: PRT
<213> ORGANISM: E. coli

<400> SEQUENCE: 10

```
Met Asn Lys Ile Leu Phe Ile Phe Thr Leu Phe Phe Ser Ser Val Leu
  1               5                  10                  15

Phe Thr Phe Ala Val Ser Ala Asp Lys Ile Pro Gly Asp Glu Ser Ile
             20                  25                  30

Thr Asn Ile Phe Gly Pro Arg Asp Arg Asn Glu Ser Ser Pro Lys His
         35                  40                  45

Asn Ile Leu Asn Asn His Ile Thr Ala Tyr Ser Glu Ser His Thr Leu
     50                  55                  60

Tyr Asp Arg Met Thr Phe Leu Cys Leu Ser Ser His Asn Thr Leu Asn
 65                  70                  75                  80

Gly Ala Cys Pro Thr Ser Glu Asn Pro Ser Ser Ser Val Ser Gly
                 85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Leu Leu Phe Lys Ser Val
        115                 120                 125

Asn Cys Pro Ser Gly Leu Thr Leu Asn Ser Ala His Phe Asn Cys Asn
    130                 135                 140

Lys Asn Ala Ala Ser Gly Ala Ser Leu Tyr Leu Tyr Ile Pro Ala Gly
145                 150                 155                 160

Glu Leu Lys Asn Leu Pro Phe Gly Gly Ile Trp Asp Ala Thr Leu Lys
                165                 170                 175

Leu Arg Val Lys Arg Arg Tyr Ser Glu Thr Tyr Gly Thr Tyr Thr Ile
            180                 185                 190

Asn Ile Thr Ile Lys Leu Thr Asp Lys Gly Asn Ile Gln Ile Trp Leu
        195                 200                 205

Pro Gln Phe Lys Ser Asp Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240
```

Asp Gly Tyr Ser Thr Asn Ser Ser Leu Glu Ile Arg Phe Gln Asp
            245                 250                 255

Asn Asn Pro Lys Ser Asp Gly Lys Phe Tyr Leu Arg Lys Ile Asn Asp
        260                 265                 270

Asp Thr Lys Glu Ile Ala Tyr Thr Leu Ser Leu Leu Leu Ala Gly Lys
    275                 280                 285

Ser Leu Thr Pro Thr Asn Gly Thr Ser Leu Asn Ile Ala Asp Ala Ala
    290                 295                 300

Ser Leu Glu Thr Asn Trp Asn Arg Ile Thr Ala Val Thr Met Pro Glu
305                 310                 315                 320

Ile Ser Val Pro Val Leu Cys Trp Pro Gly Arg Leu Gln Leu Asp Ala
                325                 330                 335

Lys Val Glu Asn Pro Glu Ala Gly Gln Tyr Met Gly Asn Ile Asn Val
            340                 345                 350

Thr Phe Thr Pro Ser Ser Gln Thr Leu
        355                 360

<210> SEQ ID NO 11
<211> LENGTH: 29
<212> TYPE: DNA
<213> ORGANISM: Artificial Sequence
<220> FEATURE:
<223> OTHER INFORMATION: PCR Primer

<400> SEQUENCE: 11
gttgacccta caattgatat tttgcaagc                              29

<210> SEQ ID NO 12
<211> LENGTH: 30
<212> TYPE: DNA
<213> ORGANISM: Artificial Sequence
<220> FEATURE:
<223> OTHER INFORMATION: PCR Primer

<400> SEQUENCE: 12
cgaccccact ataattcccg ccgttggtgc                             30

<210> SEQ ID NO 13
<211> LENGTH: 30
<212> TYPE: DNA
<213> ORGANISM: Artificial Sequence
<220> FEATURE:
<223> OTHER INFORMATION: PCR Primer

<400> SEQUENCE: 13
gtgatatgtt tgttcacttt ggtaaagatc                             30

<210> SEQ ID NO 14
<211> LENGTH: 36
<212> TYPE: DNA
<213> ORGANISM: Artificial Sequence
<220> FEATURE:
<223> OTHER INFORMATION: PCR Primer

<400> SEQUENCE: 14
ctcatggctc catttgttgc aaatgcaaac tttatg                      36

<210> SEQ ID NO 15
<211> LENGTH: 60
<212> TYPE: DNA
<213> ORGANISM: Artificial Sequence
<220> FEATURE:

<223> OTHER INFORMATION: PCR Primer

<400> SEQUENCE: 15
gggatcgatc ccggggcggc cgcgggcccg gtaccaggcc ttctagaaag cttgacgtcg    60

<210> SEQ ID NO 16
<211> LENGTH: 61
<212> TYPE: DNA
<213> ORGANISM: Artificial Sequence
<220> FEATURE:
<223> OTHER INFORMATION: PCR Primer

<400> SEQUENCE: 16
cccgctagcg gcgcgcctcg cgaggatccg tcgacgacgt caagctttct agaaggcctg    60
g                                                                    61

<210> SEQ ID NO 17
<211> LENGTH: 20
<212> TYPE: DNA
<213> ORGANISM: Artificial Sequence
<220> FEATURE:
<223> OTHER INFORMATION: PCR Primer

<400> SEQUENCE: 17
aagcttgacg tcgtcgacgg                                                 20

<210> SEQ ID NO 18
<211> LENGTH: 22
<212> TYPE: DNA
<213> ORGANISM: Artificial Sequence
<220> FEATURE:
<223> OTHER INFORMATION: PCR Primer

<400> SEQUENCE: 18
cccgctagcg gcgcgcctcg cg                                              22

<210> SEQ ID NO 19
<211> LENGTH: 26
<212> TYPE: DNA
<213> ORGANISM: Artificial Sequence
<220> FEATURE:
<223> OTHER INFORMATION: PCR Primer

<400> SEQUENCE: 19
ccgtgctgac tctacacccc cagatg                                          26

<210> SEQ ID NO 20
<211> LENGTH: 25
<212> TYPE: DNA
<213> ORGANISM: Artificial Sequence
<220> FEATURE:
<223> OTHER INFORMATION: PCR Primer

<400> SEQUENCE: 20
gcacatagag aggatagtaa cgccg                                           25

<210> SEQ ID NO 21
<211> LENGTH: 25
<212> TYPE: DNA
<213> ORGANISM: Artificial Sequence
<220> FEATURE:
<223> OTHER INFORMATION: PCR Primer

<400> SEQUENCE: 21
cggtcattgt tggccgtgcg ctgcc                                           25

<210> SEQ ID NO 22
<211> LENGTH: 28
<212> TYPE: DNA
<213> ORGANISM: Artificial Sequence
<220> FEATURE:
<223> OTHER INFORMATION: PCR Primer

<400> SEQUENCE: 22
cacgcagcgc gctgatgcct tccacgcg                                                    28

<210> SEQ ID NO 23
<211> LENGTH: 25
<212> TYPE: DNA
<213> ORGANISM: Artificial Sequence
<220> FEATURE:
<223> OTHER INFORMATION: PCR Primer

<400> SEQUENCE: 23
catatttgat atctgagata tctgg                                                       25

<210> SEQ ID NO 24
<211> LENGTH: 23
<212> TYPE: DNA
<213> ORGANISM: Artificial Sequence
<220> FEATURE:
<223> OTHER INFORMATION: PCR Primer

<400> SEQUENCE: 24
tgttgcattc agattgaacg gag                                                         23

<210> SEQ ID NO 25
<211> LENGTH: 24
<212> TYPE: DNA
<213> ORGANISM: Artificial Sequence
<220> FEATURE:
<223> OTHER INFORMATION: PCR Primer

<400> SEQUENCE: 25
tattatgatt cataaataca ctgt                                                        24

<210> SEQ ID NO 26
<211> LENGTH: 50
<212> TYPE: DNA
<213> ORGANISM: Artificial Sequence
<220> FEATURE:
<223> OTHER INFORMATION: PCR Primer

<400> SEQUENCE: 26
tgtgggtatt tgtttggaca tcgcagcatt aaatataaaa atagcacagg                            50

<210> SEQ ID NO 27
<211> LENGTH: 7239
<212> TYPE: DNA
<213> ORGANISM: E. coli
<220> FEATURE:
<221> NAME/KEY: CDS
<222> LOCATION: (283)...(999)
<220> FEATURE:
<221> NAME/KEY: CDS
<222> LOCATION: (1028)...(1531)
<220> FEATURE:
<221> NAME/KEY: CDS
<222> LOCATION: (1589)...(4192)
<220> FEATURE:
<221> NAME/KEY: CDS
<222> LOCATION: (4196)...(5281)
<220> FEATURE:

```
<221> NAME/KEY: CDS
<222> LOCATION: (5790)...(6119)

<400> SEQUENCE: 27
atatatctta ttgaggaata tcggtgtcat tgagtaccgt taacttaaga taaagaatct      60
gtctggaaat cgcaggacca agaactctca gtacatctgt ggcgataata ttatcgcttc     120
ttatacattc caatatgcag ttcttgtggg tatttgtttg gacatcgcag cattaaatat     180
aaaaatagca caggaggcat aattatttgt ttttactgtc ttattttttt atcccatttt     240 ttttttgtttt gatttatctt tgatgaaagc tcaggaggga atatg cat aaa tta ttt    297
                                               His Lys Leu Phe
                                                 1 tgt tta cta agt tta ctc ata act cca ttt gtt gca aat gca aac ttt       345
Cys Leu Leu Ser Leu Leu Ile Thr Pro Phe Val Ala Asn Ala Asn Phe
  5              10                  15                  20 atg ata tat cca ata tca aaa gat tta aag aat gga aat agc gag tta       393
Met Ile Tyr Pro Ile Ser Lys Asp Leu Lys Asn Gly Asn Ser Glu Leu
             25                  30                  35 att cgt gtt tat tca aaa tca aaa gag ata caa tat ata aaa ata tat       441
Ile Arg Val Tyr Ser Lys Ser Lys Glu Ile Gln Tyr Ile Lys Ile Tyr
         40                  45                  50 aca aaa aag att att aat ccc ggc aca act gaa gaa cat gaa gtt gat       489
Thr Lys Lys Ile Ile Asn Pro Gly Thr Thr Glu Glu His Glu Val Asp
     55                  60                  65 atg ccc aat tgg gat ggt ggg ttt gta gtt act cct caa aaa gtt att       537
Met Pro Asn Trp Asp Gly Gly Phe Val Val Thr Pro Gln Lys Val Ile
 70                  75                  80 ctt cct gca gga ggg agt aaa tca ata cgt tta act caa ttt aga ata       585
Leu Pro Ala Gly Gly Ser Lys Ser Ile Arg Leu Thr Gln Phe Arg Ile
 85                  90                  95                 100 cca aaa aaa gag gaa att tat aga gta tat ttt gag gcg gta aaa cca       633
Pro Lys Lys Glu Glu Ile Tyr Arg Val Tyr Phe Glu Ala Val Lys Pro
                105                 110                 115 gat agc aaa gaa aat gta att gat aat aaa aaa cta aca aca gag cta       681
Asp Ser Lys Glu Asn Val Ile Asp Asn Lys Lys Leu Thr Thr Glu Leu
            120                 125                 130 tct gtt aat ata att tat gcg gct cta atc aga tct tta cca agt gaa       729
Ser Val Asn Ile Ile Tyr Ala Ala Leu Ile Arg Ser Leu Pro Ser Glu
        135                 140                 145 caa aac ata tca cta aac att tct aga aat gca aga aaa aat ata att       777
Gln Asn Ile Ser Leu Asn Ile Ser Arg Asn Ala Arg Lys Asn Ile Ile
    150                 155                 160 att tat aat aat ggg aat gtt aga gca ggt gtt aaa gat att tat ttt       825
Ile Tyr Asn Asn Gly Asn Val Arg Ala Gly Val Lys Asp Ile Tyr Phe
165                 170                 175                 180 tgt aag tca tct aat atc gat gat agc tgt gta aaa aaa acg cat aac       873
Cys Lys Ser Ser Asn Ile Asp Asp Ser Cys Val Lys Lys Thr His Asn
                185                 190                 195 aag aat ata tat cca gaa aag tca ttt gat acg ctg gtt aat aac aat       921
Lys Asn Ile Tyr Pro Glu Lys Ser Phe Asp Thr Leu Val Asn Asn Asn
            200                 205                 210 ttt tct tat gtt ttc att aaa tta aac cat gaa gac ata gaa aaa gag       969
Phe Ser Tyr Val Phe Ile Lys Leu Asn His Glu Asp Ile Glu Lys Glu
        215                 220                 225 caa gga cta ata caa tta aaa gtt cct tga tta ctcatctata tactaaggag    1022
Gln Gly Leu Ile Gln Leu Lys Val Pro *   Leu
    230                 235 ttctaatgaa attaaaaaaa actattggtg caatg gca ctg acc aca atg ttt       1075
                                       Ala Leu Thr Thr Met Phe
```

-continued

```
                                  240
gta gct atg agt gct tct gca gta gag aaa aat atc act gta aca gct    1123
Val Ala Met Ser Ala Ser Ala Val Glu Lys Asn Ile Thr Val Thr Ala
245             250                 255                 260 agt gtt gat cct aca att gat att ttg caa gct gat ggt agt agt tta    1171
Ser Val Asp Pro Thr Ile Asp Ile Leu Gln Ala Asp Gly Ser Ser Leu
                265                 270                 275 cct act gct gta gaa tta acc tat tca cct gcg gca agt cgt ttt gaa    1219
Pro Thr Ala Val Glu Leu Thr Tyr Ser Pro Ala Ala Ser Arg Phe Glu
280                 285                 290 aat tat aaa atc gca act aaa gtt cat aca aat gtt ata aat aaa aat    1267
Asn Tyr Lys Ile Ala Thr Lys Val His Thr Asn Val Ile Asn Lys Asn
    295                 300                 305 gta cta gtt aag ctt gta aat gat cca aaa ctt aca aat gtt ttg gat    1315
Val Leu Val Lys Leu Val Asn Asp Pro Lys Leu Thr Asn Val Leu Asp
310                 315                 320 tct aca aaa caa ctc ccc att act gta tca tat gga gga aag act cta    1363
Ser Thr Lys Gln Leu Pro Ile Thr Val Ser Tyr Gly Gly Lys Thr Leu
325                 330                 335                 340 tca acc gca gat gtg act ttt gaa cct gca gaa tta aat ttt gga acg    1411
Ser Thr Ala Asp Val Thr Phe Glu Pro Ala Glu Leu Asn Phe Gly Thr
                345                 350                 355 tca ggt gta act ggt gta tct tct tcc caa gat tta gtg att ggt gcg    1459
Ser Gly Val Thr Gly Val Ser Ser Ser Gln Asp Leu Val Ile Gly Ala
                360                 365                 370 act aca gca caa gca cca acg gcg gga aat tat agt ggg gtc gtt tct    1507
Thr Thr Ala Gln Ala Pro Thr Ala Gly Asn Tyr Ser Gly Val Val Ser
                375                 380                 385 atc tta atg acc tta gca tca taa ata ttttaatata taaaggagca          1554
Ile Leu Met Thr Leu Ala Ser  *  Ile
                390                 395 ggcacactgc tccttattat atggcaataa taaaatg aca aaa aaa aat aca tta   1609
                                         Thr Lys Lys Asn Thr Leu
                                                             400 tat ata acg atc atc gca atg cta act cca tat tca gtt ttt tcc gga    1657
Tyr Ile Thr Ile Ile Ala Met Leu Thr Pro Tyr Ser Val Phe Ser Gly
            405                 410                 415 gat ata ccc aac tct ttc cgt gat tta tgg gga gaa caa gat gaa ttt    1705
Asp Ile Pro Asn Ser Phe Arg Asp Leu Trp Gly Glu Gln Asp Glu Phe
        420                 425                 430 tat gaa gta aaa cta tat gga caa act cta gga ata cat cga att aaa    1753
Tyr Glu Val Lys Leu Tyr Gly Gln Thr Leu Gly Ile His Arg Ile Lys
435                 440                 445                 450 aca acc cca aca cat att aag ttt tat tca ccc gaa agc att tta gat    1801
Thr Thr Pro Thr His Ile Lys Phe Tyr Ser Pro Glu Ser Ile Leu Asp
                455                 460                 465 aaa ata aat gta aaa aaa gaa aag gaa aag aaa ttg agt gtt ttg ttc    1849
Lys Ile Asn Val Lys Lys Glu Lys Glu Lys Lys Leu Ser Val Leu Phe
            470                 475                 480 act aat tct ttt tca aga aat ggc aat atg agt tgt cag ggg aat gct    1897
Thr Asn Ser Phe Ser Arg Asn Gly Asn Met Ser Cys Gln Gly Asn Ala
        485                 490                 495 act ata cag tat aac tgc aat tac att aaa aca aaa tca gta gat gtc    1945
Thr Ile Gln Tyr Asn Cys Asn Tyr Ile Lys Thr Lys Ser Val Asp Val
500                 505                 510 atc gtt gat gat gtt gat aat gtt gtt aac ctt ttt ata ggt aat gaa    1993
Ile Val Asp Asp Val Asp Asn Val Val Asn Leu Phe Ile Gly Asn Glu
515                 520                 525                 530 ttt ctg gat tct gaa gca cac aat gat gaa tat cat caa tta tca cga    2041
```

|          |          |          |          |          |          |          |          |          |          |          |          |          |          |          |          |      |
|----------|----------|----------|----------|----------|----------|----------|----------|----------|----------|----------|----------|----------|----------|----------|----------|------|
| Phe      | Leu      | Asp      | Ser      | Glu      | Ala      | His      | Asn      | Asp      | Glu      | Tyr      | His      | Gln      | Leu      | Ser      | Arg      |      |
|          |          |          |          | 535      |          |          |          |          | 540      |          |          |          |          | 545      |          |      |
| aat      | gta      | aaa      | aaa      | gct      | ttt      | ata      | caa      | agc      | cag      | aca      | att      | aat      | gtc      | tca      | gat      | 2089 |
| Asn      | Val      | Lys      | Lys      | Ala      | Phe      | Ile      | Gln      | Ser      | Gln      | Thr      | Ile      | Asn      | Val      | Ser      | Asp      |      |
|          |          |          | 550      |          |          |          |          | 555      |          |          |          |          | 560      |          |          |      |
| tct      | ggg      | aag      | tat      | aaa      | agt      | ttg      | tct      | gtt      | tca      | ggg      | aat      | agc      | gcg      | ctg      | ggt      | 2137 |
| Ser      | Gly      | Lys      | Tyr      | Lys      | Ser      | Leu      | Ser      | Val      | Ser      | Gly      | Asn      | Ser      | Ala      | Leu      | Gly      |      |
|          |          | 565      |          |          |          |          | 570      |          |          |          |          | 575      |          |          |          |      |
| att      | aca      | gat      | aca      | agt      | tat      | gct      | gtc      | tta      | aat      | tgg      | tgg      | atg      | aat      | tac      | aat      | 2185 |
| Ile      | Thr      | Asp      | Thr      | Ser      | Tyr      | Ala      | Val      | Leu      | Asn      | Trp      | Trp      | Met      | Asn      | Tyr      | Asn      |      |
|          |          |          | 580      |          |          |          |          | 585      |          |          |          |          | 590      |          |          |      |
| aaa      | ttt      | aat      | ggt      | tac      | agc      | aac      | aac      | gaa      | aga      | aca      | atc      | aat      | agt      | ttg      | tac      | 2233 |
| Lys      | Phe      | Asn      | Gly      | Tyr      | Ser      | Asn      | Asn      | Glu      | Arg      | Thr      | Ile      | Asn      | Ser      | Leu      | Tyr      |      |
| 595      |          |          |          |          | 600      |          |          |          |          | 605      |          |          |          |          | 610      |      |
| ttt      | aga      | cat      | gat      | tta      | gat      | aag      | aga      | tat      | tat      | tat      | caa      | ttt      | gga      | cga      | atg      | 2281 |
| Phe      | Arg      | His      | Asp      | Leu      | Asp      | Lys      | Arg      | Tyr      | Tyr      | Tyr      | Gln      | Phe      | Gly      | Arg      | Met      |      |
|          |          |          |          | 615      |          |          |          |          | 620      |          |          |          |          | 625      |          |      |
| gat      | cgt      | aca      | gat      | ttg      | tca      | caa      | agt      | att      | agc      | ggg      | aac      | ttt      | aat      | ttt      | aac      | 2329 |
| Asp      | Arg      | Thr      | Asp      | Leu      | Ser      | Gln      | Ser      | Ile      | Ser      | Gly      | Asn      | Phe      | Asn      | Phe      | Asn      |      |
|          |          |          | 630      |          |          |          |          | 635      |          |          |          |          | 640      |          |          |      |
| tta      | ctt      | cct      | tta      | ccc      | gat      | att      | gat      | ggt      | ata      | agg      | aca      | gga      | acc      | aca      | caa      | 2377 |
| Leu      | Leu      | Pro      | Leu      | Pro      | Asp      | Ile      | Asp      | Gly      | Ile      | Arg      | Thr      | Gly      | Thr      | Thr      | Gln      |      |
|          |          | 645      |          |          |          |          | 650      |          |          |          |          | 655      |          |          |          |      |
| tct      | tat      | atc      | aaa      | aat      | aca      | gat      | aag      | ttt      | atc      | gca      | tcc      | cct      | gta      | act      | gtt      | 2425 |
| Ser      | Tyr      | Ile      | Lys      | Asn      | Thr      | Asp      | Lys      | Phe      | Ile      | Ala      | Ser      | Pro      | Val      | Thr      | Val      |      |
|          | 660      |          |          |          |          | 665      |          |          |          |          | 670      |          |          |          |          |      |
| atg      | tta      | act      | aat      | ttt      | tcc      | aga      | gtg      | gaa      | gct      | ttt      | cgc      | aat      | aat      | caa      | tta      | 2473 |
| Met      | Leu      | Thr      | Asn      | Phe      | Ser      | Arg      | Val      | Glu      | Ala      | Phe      | Arg      | Asn      | Asn      | Gln      | Leu      |      |
| 675      |          |          |          |          | 680      |          |          |          |          | 685      |          |          |          |          | 690      |      |
| ttg      | ggc      | gta      | tgg      | tat      | tta      | gat      | tct      | gga      | gta      | aat      | gaa      | tta      | gat      | aca      | gct      | 2521 |
| Leu      | Gly      | Val      | Trp      | Tyr      | Leu      | Asp      | Ser      | Gly      | Val      | Asn      | Glu      | Leu      | Asp      | Thr      | Ala      |      |
|          |          |          |          | 695      |          |          |          |          | 700      |          |          |          |          | 705      |          |      |
| cgt      | tta      | cct      | tat      | ggt      | agt      | tac      | gat      | ctt      | aaa      | tta      | aaa      | att      | ttt      | gaa      | aat      | 2569 |
| Arg      | Leu      | Pro      | Tyr      | Gly      | Ser      | Tyr      | Asp      | Leu      | Lys      | Leu      | Lys      | Ile      | Phe      | Glu      | Asn      |      |
|          |          |          | 710      |          |          |          |          | 715      |          |          |          |          | 720      |          |          |      |
| act      | cag      | tta      | gtt      | cgt      | gaa      | gaa      | ata      | att      | cct      | ttt      | aat      | aaa      | ggg      | aga      | agt      | 2617 |
| Thr      | Gln      | Leu      | Val      | Arg      | Glu      | Glu      | Ile      | Ile      | Pro      | Phe      | Asn      | Lys      | Gly      | Arg      | Ser      |      |
|          |          | 725      |          |          |          |          | 730      |          |          |          |          | 735      |          |          |          |      |
| tct      | att      | ggt      | gat      | atg      | caa      | tgg      | gac      | gtt      | ttc      | att      | cag      | gga      | ggg      | aat      | att      | 2665 |
| Ser      | Ile      | Gly      | Asp      | Met      | Gln      | Trp      | Asp      | Val      | Phe      | Ile      | Gln      | Gly      | Gly      | Asn      | Ile      |      |
|          |          |          | 740      |          |          |          |          | 745      |          |          |          |          | 750      |          |          |      |
| att      | aat      | gac      | aag      | gat      | cgt      | tac      | ata      | gaa      | aaa      | caa      | aat      | aat      | cat      | aag      | tca      | 2713 |
| Ile      | Asn      | Asp      | Lys      | Asp      | Arg      | Tyr      | Ile      | Glu      | Lys      | Gln      | Asn      | Asn      | His      | Lys      | Ser      |      |
| 755      |          |          |          |          | 760      |          |          |          |          | 765      |          |          |          |          | 770      |      |
| tca      | gtt      | aat      | gct      | ggg      | cta      | cgt      | tta      | cca      | att      | acg      | aaa      | aat      | atc      | tct      | gtt      | 2761 |
| Ser      | Val      | Asn      | Ala      | Gly      | Leu      | Arg      | Leu      | Pro      | Ile      | Thr      | Lys      | Asn      | Ile      | Ser      | Val      |      |
|          |          |          |          | 775      |          |          |          |          | 780      |          |          |          |          | 785      |          |      |
| caa      | caa      | gga      | gca      | tct      | gtt      | ata      | gat      | aat      | aaa      | aat      | tat      | tat      | gaa      | ggg      | agt      | 2809 |
| Gln      | Gln      | Gly      | Ala      | Ser      | Val      | Ile      | Asp      | Asn      | Lys      | Asn      | Tyr      | Tyr      | Glu      | Gly      | Ser      |      |
|          |          |          |          | 790      |          |          |          |          | 795      |          |          |          |          | 800      |          |      |
| ctc      | aaa      | tgg      | aat      | tcc      | ggc      | att      | ctg      | tct      | ggc      | tca      | cta      | aat      | agt      | gag      | ttc      | 2857 |
| Leu      | Lys      | Trp      | Asn      | Ser      | Gly      | Ile      | Leu      | Ser      | Gly      | Ser      | Leu      | Asn      | Ser      | Glu      | Phe      |      |
|          |          | 805      |          |          |          |          | 810      |          |          |          |          | 815      |          |          |          |      |
| agt      | ttt      | ctt      | tgg      | gga      | gat      | aat      | gca      | aaa      | ggt      | aat      | tat      | caa      | agt      | atc      | tcg      | 2905 |
| Ser      | Phe      | Leu      | Trp      | Gly      | Asp      | Asn      | Ala      | Lys      | Gly      | Asn      | Tyr      | Gln      | Ser      | Ile      | Ser      |      |
|          |          |          | 820      |          |          |          |          | 825      |          |          |          |          | 830      |          |          |      |
| tat      | acc      | gat      | gga      | ttt      | agt      | tta      | tca      | ttt      | tat      | cat      | aat      | gat      | aag      | cgg      | gtc      | 2953 |
| Tyr      | Thr      | Asp      | Gly      | Phe      | Ser      | Leu      | Ser      | Phe      | Tyr      | His      | Asn      | Asp      | Lys      | Arg      | Val      |      |
| 835      |          |          |          |          | 840      |          |          |          |          | 845      |          |          |          |          | 850      |      |

```
gat aat tgt gga aga aat tac aat gct ggt tgg agt gga tgc tac gaa    3001
Asp Asn Cys Gly Arg Asn Tyr Asn Ala Gly Trp Ser Gly Cys Tyr Glu
            855                 860                 865 tca tat tcg gca tct tta agt att cct tta ttg gga tgg aca agt act    3049
Ser Tyr Ser Ala Ser Leu Ser Ile Pro Leu Leu Gly Trp Thr Ser Thr
        870                 875                 880 ctg gga tat agt gac act tat agt gaa tca gtt tat aaa aac cat att    3097
Leu Gly Tyr Ser Asp Thr Tyr Ser Glu Ser Val Tyr Lys Asn His Ile
                885                 890                 895 ctt tct gaa tat ggt ttt tat aat caa aac ata tat aaa ggg aga acc    3145
Leu Ser Glu Tyr Gly Phe Tyr Asn Gln Asn Ile Tyr Lys Gly Arg Thr
900                 905                 910 caa aga tgg caa ctg act tcg tcc acc tct tta aaa tgg atg gat tat    3193
Gln Arg Trp Gln Leu Thr Ser Ser Thr Ser Leu Lys Trp Met Asp Tyr
915                 920                 925                 930 aat ttt atg cca gca att gga ata tat aac agt gag caa aga caa ctg    3241
Asn Phe Met Pro Ala Ile Gly Ile Tyr Asn Ser Glu Gln Arg Gln Leu
                935                 940                 945 act gat aaa ggc gga tat ata tct gta act ctc acc cga gcc agc aga    3289
Thr Asp Lys Gly Gly Tyr Ile Ser Val Thr Leu Thr Arg Ala Ser Arg
            950                 955                 960 gaa aat tca tta aac gca ggg tat tct tac aac tat tcc aga gga aag    3337
Glu Asn Ser Leu Asn Ala Gly Tyr Ser Tyr Asn Tyr Ser Arg Gly Lys
        965                 970                 975 tat tct tct aac gaa tta ttt gtt gat gga tat atg aca tca aca aat    3385
Tyr Ser Ser Asn Glu Leu Phe Val Asp Gly Tyr Met Thr Ser Thr Asn
    980                 985                 990 aat ggt gac tat cat gag gta aga atg cgt ttt aat aaa aat aga cat    3433
Asn Gly Asp Tyr His Glu Val Arg Met Arg Phe Asn Lys Asn Arg His
995                 1000                1005                1010 aat gca gaa ggt aga ctt tca ggt cgt ata aac aat cga ttt gga gat    3481
Asn Ala Glu Gly Arg Leu Ser Gly Arg Ile Asn Asn Arg Phe Gly Asp
                1015                1020                1025 tta aat ggt tca ttc agc atg aat aaa aac aga aac acc aac agt agc    3529
Leu Asn Gly Ser Phe Ser Met Asn Lys Asn Arg Asn Thr Asn Ser Ser
            1030                1035                1040 aat cat tct ctc act ggt ggt tat aat tcc tca ttt gct ctt aca agt    3577
Asn His Ser Leu Thr Gly Gly Tyr Asn Ser Ser Phe Ala Leu Thr Ser
        1045                1050                1055 gat gga ttt tac tgg gga gga agt gca tct ggt ttg aca aaa cta gct    3625
Asp Gly Phe Tyr Trp Gly Gly Ser Ala Ser Gly Leu Thr Lys Leu Ala
    1060                1065                1070 ggc ggt att atc aag gtt aaa tca aac gat act aaa aaa aat ctg gta    3673
Gly Gly Ile Ile Lys Val Lys Ser Asn Asp Thr Lys Lys Asn Leu Val
1075                1080                1085                1090 aaa gtg act ggg gca ttg tac ggt gat tat tcg cta ggg agc aac gat    3721
Lys Val Thr Gly Ala Leu Tyr Gly Asp Tyr Ser Leu Gly Ser Asn Asp
                1095                1100                1105 aat gct ttt att cct gta cca gca tta act cca gcc agt tta att att    3769
Asn Ala Phe Ile Pro Val Pro Ala Leu Thr Pro Ala Ser Leu Ile Ile
            1110                1115                1120 gaa gat aat aat tat ggt gac aag aat att tct gta ctt gca cca acg    3817
Glu Asp Asn Asn Tyr Gly Asp Lys Asn Ile Ser Val Leu Ala Pro Thr
        1125                1130                1135 aac aac gat atg ttt ata ttg ccg ggt aat gtt tat cct gtt gaa att    3865
Asn Asn Asp Met Phe Ile Leu Pro Gly Asn Val Tyr Pro Val Glu Ile
    1140                1145                1150 gaa acc aaa gta agt gtt tct tat att ggt aga ggt ttt gac aaa aac    3913
Glu Thr Lys Val Ser Val Ser Tyr Ile Gly Arg Gly Phe Asp Lys Asn
1155                1160                1165                1170
```

| | |
|---|---|
| ggc acg cca ctt tct ggc gca cat gtt ttg aat gaa cca cat gtt atc<br>Gly Thr Pro Leu Ser Gly Ala His Val Leu Asn Glu Pro His Val Ile<br>                 1175                       1180                1185 | 3961 |
| ctg gat gag gac ggt gga ttt tcg ttt gaa tat aca ggt aat gag aaa<br>Leu Asp Glu Asp Gly Gly Phe Ser Phe Glu Tyr Thr Gly Asn Glu Lys<br>        1190                     1195                 1200 | 4009 |
| aca ctt ttt tta tta aag ggc aga act att tat aca tgt caa ctg ggg<br>Thr Leu Phe Leu Leu Lys Gly Arg Thr Ile Tyr Thr Cys Gln Leu Gly<br>        1205                     1210                 1215 | 4057 |
| aaa aat aaa gtt cac aaa ggc att gtt ttc gtc gga gat gtt ata tgt<br>Lys Asn Lys Val His Lys Gly Ile Val Phe Val Gly Asp Val Ile Cys<br>      1220                 1225               1230 | 4105 |
| gat gtt aat agc aca agt tcc tta cca gat gaa ttt gta aag aac cca<br>Asp Val Asn Ser Thr Ser Ser Leu Pro Asp Glu Phe Val Lys Asn Pro<br>1235               1240               1245              1250 | 4153 |
| cgt gtg cag gat ttg ctg gca aag aat gat aaa gga taa acg<br>Arg Val Gln Asp Leu Leu Ala Lys Asn Asp Lys Gly * Thr<br>              1255                 1260 | 4195 |
| atg aat aag att tta ttt att ttt aca ttg ttt ttc tct tca gta ctt<br>    Asn Lys Ile Leu Phe Ile Phe Thr Leu Phe Phe Ser Ser Val Leu<br>        1265                     1270                 1275 | 4243 |
| ttt aca ttt gct gta tcg gca gat aaa att ccc gga gat gaa agc ata<br>Phe Thr Phe Ala Val Ser Ala Asp Lys Ile Pro Gly Asp Glu Ser Ile<br>        1280                     1285                 1290 | 4291 |
| act aat att ttt ggc ccg cgt gac agg aac gaa tct tcc ccc aaa cat<br>Thr Asn Ile Phe Gly Pro Arg Asp Arg Asn Glu Ser Ser Pro Lys His<br>1295               1300               1305              1310 | 4339 |
| aat ata tta aat aac cat att aca gca tac agt gaa agt cat act ctg<br>Asn Ile Leu Asn Asn His Ile Thr Ala Tyr Ser Glu Ser His Thr Leu<br>              1315               1320               1325 | 4387 |
| tat gat agg atg act ttt tta tgt ttg tct tct cac aat aca ctt aat<br>Tyr Asp Arg Met Thr Phe Leu Cys Leu Ser Ser His Asn Thr Leu Asn<br>        1330                     1335                 1340 | 4435 |
| gga gca tgt cca acc agt gag aat cct agc agt tca tcg gtc agc ggt<br>Gly Ala Cys Pro Thr Ser Glu Asn Pro Ser Ser Ser Ser Val Ser Gly<br>        1345                     1350                 1355 | 4483 |
| gaa aca aat ata aca tta caa ttt acg gaa aaa aga agt tta ata aaa<br>Glu Thr Asn Ile Thr Leu Gln Phe Thr Glu Lys Arg Ser Leu Ile Lys<br>        1360                     1365                 1370 | 4531 |
| aga gag cta caa att aaa ggc tat aaa caa tta ttg ttc aaa agt gtt<br>Arg Glu Leu Gln Ile Lys Gly Tyr Lys Gln Leu Leu Phe Lys Ser Val<br>1375               1380               1385               1390 | 4579 |
| aac tgc cca tcc ggc cta aca ctt aac tca gct cat ttt aac tgt aat<br>Asn Cys Pro Ser Gly Leu Thr Leu Asn Ser Ala His Phe Asn Cys Asn<br>              1395               1400               1405 | 4627 |
| aaa aac gcg gct tca ggt gca agt tta tat tta tat att cct gct ggc<br>Lys Asn Ala Ala Ser Gly Ala Ser Leu Tyr Leu Tyr Ile Pro Ala Gly<br>        1410                     1415                 1420 | 4675 |
| gaa cta aaa aat ttg cct ttt ggt ggt atc tgg gat gct act ctg aag<br>Glu Leu Lys Asn Leu Pro Phe Gly Gly Ile Trp Asp Ala Thr Leu Lys<br>        1425                     1430                 1435 | 4723 |
| tta aga gta aaa aga cga tat agt gag acc tat gga act tac act ata<br>Leu Arg Val Lys Arg Arg Tyr Ser Glu Thr Tyr Gly Thr Tyr Thr Ile<br>        1440                     1445                 1450 | 4771 |
| aat atc act att aaa tta act gat aag gga aat att cag ata tgg tta<br>Asn Ile Thr Ile Lys Leu Thr Asp Lys Gly Asn Ile Gln Ile Trp Leu<br>1455               1460               1465              1470 | 4819 |
| cct cag ttc aaa agt gac gct cgc gtc gat ctt aac ttg cgt cca act<br>Pro Gln Phe Lys Ser Asp Ala Arg Val Asp Leu Asn Leu Arg Pro Thr | 4867 |

-continued

```
                  1475              1480              1485
ggt ggg ggc aca tat att gga aga aat tct gtt gat atg tgc ttt tat    4915
Gly Gly Gly Thr Tyr Ile Gly Arg Asn Ser Val Asp Met Cys Phe Tyr
            1490              1495              1500 gat gga tat agt act aac agc agc tct ttg gag ata aga ttt cag gat    4963
Asp Gly Tyr Ser Thr Asn Ser Ser Leu Glu Ile Arg Phe Gln Asp
        1505              1510              1515 aac aat cct aaa tct gat ggg aaa ttt tat cta agg aaa ata aat gat    5011
Asn Asn Pro Lys Ser Asp Gly Lys Phe Tyr Leu Arg Lys Ile Asn Asp
        1520              1525              1530 gac acc aaa gaa att gca tat act ttg tca ctt ctc ttg gcg ggt aaa    5059
Asp Thr Lys Glu Ile Ala Tyr Thr Leu Ser Leu Leu Leu Ala Gly Lys
1535              1540              1545              1550 agt tta act cca aca aat gga acg tca tta aat att gct gac gca gct    5107
Ser Leu Thr Pro Thr Asn Gly Thr Ser Leu Asn Ile Ala Asp Ala Ala
                1555              1560              1565 tct ctg gaa aca aac tgg aat aga att aca gct gtc acc atg cca gaa    5155
Ser Leu Glu Thr Asn Trp Asn Arg Ile Thr Ala Val Thr Met Pro Glu
            1570              1575              1580 atc agt gtt ccg gtg ttg tgt tgg cct gga cgt ttg caa ttg gat gca    5203
Ile Ser Val Pro Val Leu Cys Trp Pro Gly Arg Leu Gln Leu Asp Ala
        1585              1590              1595 aaa gtg gaa aat ccc gag gct gga caa tat atg ggt aat att aat gtt    5251
Lys Val Glu Asn Pro Glu Ala Gly Gln Tyr Met Gly Asn Ile Asn Val
        1600              1605              1610 act ttc aca cca agt agt caa aca ctc tag ata acaacaatat tggcgctatt  5304
Thr Phe Thr Pro Ser Ser Gln Thr Leu  *  Ile
1615              1620 gcgcgccaat attgtaaagg ggtaatctgt ttgttaacaa acatttttgt ttcaattcag  5364
tttgcatcgc aataaatctc tactagagac attttttatac agcatagtat tatacaacac 5424 attcaaaata aggatatttt tatccaccctt taaaataagt aaaaaactgc tttggtataa  5484
caccataatg tttattaaaa acctaataa aataagatgt actggaaatt ccaatcatat    5544
ttgatatctg agatatctgg tatgaattt caagtagtaa taacgctgcc ttgctcattc    5604
tcaattgcat taagaactgg ttaaaattag tattctcaga ttctagtctt tttctgatgg   5664
ttatttctga ttcattaaac atatctgcaa tgatagccag tgtccatttt ctggatagat   5724 cttttttcgat aatatttctg accttgtcag aaaaaaattc acagatgata tataaattga  5784 ttctatta ttt ttt att att ctc gat ctt tga aat taa ata tat caa att   5834
         Phe Phe Ile Ile Leu Asp Leu  *  Asn  *  Ile Tyr Gln Ile
              1625              1630              1635 aga tat aaa agc tga gtc atc ata gct att tat att ttt taa tac atc    5882
Arg Tyr Lys Ser  *  Val Ile Ile Ala Ile Tyr Ile Phe  *  Tyr Ile
            1640              1645              1650 cag taa ggt ttt atc cac ttc tgt ttt cat tat ttt cct tga cat att    5930
Gln  *  Gly Phe Ile His Phe Cys Phe His Tyr Phe Pro  *  His Ile
            1655              1660 tct aca atc att ggt atc tat ttt tga cat acc ata tat tat cat caa    5978
Ser Thr Ile Ile Gly Ile Tyr Phe  *  His Thr Ile Tyr Tyr His Gln
1665              1670              1675 tgc atc ctt taa atg tct tag tat gtc tcc gtt caa tct gaa tgc aac    6026
Cys Ile Leu  *  Met Ser  *  Tyr Val Ser Val Gln Ser Glu Cys Asn
1680              1685              1690 ata tgg ttt ttc tga taa aat ttg ctt ctg tat tct tac aga tat att    6074
Ile Trp Phe Phe  *   *  Asn Leu Leu Leu Tyr Ser Tyr Arg Tyr Ile
        1695              1700              1705 cac ccc tct ttc aag aaa tac agg t gatgctgcca acttactgat             6119
```

```
His Pro Ser Phe Lys Lys Tyr Arg
        1710                1715
```

| | |
|---|---:|
| ttagtgtatg atggtgtttt tgaggtgctc cagtggcttc tgtttctatc agctgtccct | 6179 |
| cctgttcagc tactgacggg gtggtgcgta acggcaaaag cactgccgga catcagcgct | 6239 |
| atctctgctc tcactgccgt aaaacatggc aactgcagtt cacttacact gcttctcaac | 6299 |
| ccggtacgca ccagaaaatc attgatatgg ccatgaatgg cgttggatgc cgggcaacag | 6359 |
| cccgcattat gggcgttggc ctcaacacga ttttacgtca cttaaaaaac tcaggccgca | 6419 |
| gtcggtaacc tcgcgcatac agccgggcag tgacgtcatc gtctgcgcgg aaatggacga | 6479 |
| acagtggggc tatgtcgggg ctaaatcgcg ccagcgctgg ctgttttacg cgtatgacag | 6539 |
| gctccggaag acggttgttg cgcacgtatt cggtgaacgc actatggcga cgctggggcg | 6599 |
| tcttatgagc ctgctgtcac cctttgacgt ggtgatatgg atgacggatg gctggccgct | 6659 |
| gtatgaatcc cgcctgaagg gaaagctgca cgtaatcagc aagcgatata cgcagcgaat | 6719 |
| tgagcggcat aacctgaatc tgaggcagca cctggcacgg ctgggacgga agtcgctgtc | 6779 |
| gttctcaaaa tcggtggagc tgcatgacaa agtcatcggg cattatctga acataaaaca | 6839 |
| ctatcaataa gttagagtca ttacctggtt cacgtattat tatccgtgac tctttcctgg | 6899 |
| taactcccgc ataataacct cacttttcca gtattccaga agatgatgtt ttttcctcga | 6959 |
| taataaaaat gtgccaatat ggaaataaga aatcggattt tttatcagca tacgcaaatt | 7019 |
| ttcagataac aatgaataca gatgtatttt atatacacag ataaaaccgc gcaacagaca | 7079 |
| taaatatgac agtagcatga aaaagcagag agagacaggg tgatacagaa aagtaactat | 7139 |
| tttttttagct atagtattat tggttttacc tattttcgtg attgtgtttc tgtatatttg | 7199 |
| acaatgagtc tctcagaatc ggtttctcga agtgacgagc | 7239 |

```
<210> SEQ ID NO 28
<211> LENGTH: 361
<212> TYPE: PRT
<213> ORGANISM: Artificial Sequence
<220> FEATURE:
<223> OTHER INFORMATION: ETEC Protein Homology Sequence

<400> SEQUENCE: 28

Thr Met Asn Lys Ile Leu Phe Ile Phe Thr Leu Phe Phe Ser Ser Val
 1               5                  10                  15

Leu Phe Thr Phe Ala Val Ser Ala Asp Lys Ile Pro Gly Asp Glu Ser
            20                  25                  30

Ile Thr Asn Ile Phe Gly Pro Arg Asp Arg Asn Glu Ser Ser Pro Lys
        35                  40                  45

His Asn Ile Leu Asn Asn His Ile Thr Ala Tyr Ser Glu Ser His Thr
    50                  55                  60

Leu Tyr Asp Arg Met Thr Phe Leu Cys Leu Ser Ser His Asn Thr Leu
65                  70                  75                  80

Asn Gly Ala Cys Pro Thr Ser Glu Asn Pro Ser Ser Ser Val Ser
                85                  90                  95

Gly Glu Thr Asn Ile Thr Leu Gln Phe Thr Glu Lys Arg Ser Leu Ile
            100                 105                 110

Lys Arg Glu Leu Gln Ile Lys Gly Tyr Lys Gln Leu Leu Phe Lys Ser
        115                 120                 125

Val Asn Cys Pro Ser Gly Leu Thr Leu Asn Ser Ala His Phe Asn Cys
    130                 135                 140

Asn Lys Asn Ala Ala Ser Gly Ala Ser Leu Tyr Leu Tyr Ile Pro Ala
```

```
                    145                 150                 155                 160
Gly Glu Leu Lys Asn Leu Pro Phe Gly Gly Ile Trp Asp Ala Thr Leu
                165                 170                 175

Lys Leu Arg Val Lys Arg Arg Tyr Ser Glu Thr Tyr Gly Thr Tyr Thr
            180                 185                 190

Ile Asn Ile Thr Ile Lys Leu Thr Asp Lys Gly Asn Ile Gln Ile Trp
        195                 200                 205

Leu Pro Gln Phe Lys Ser Asp Ala Arg Val Asp Leu Asn Leu Arg Pro
    210                 215                 220

Thr Gly Gly Thr Tyr Ile Gly Arg Asn Ser Val Asp Met Cys Phe
225                 230                 235                 240

Tyr Asp Gly Tyr Ser Thr Asn Ser Ser Leu Glu Ile Arg Phe Gln
                245                 250                 255

Asp Asn Asn Pro Lys Ser Asp Gly Lys Phe Tyr Leu Arg Lys Ile Asn
                260                 265                 270

Asp Asp Thr Lys Glu Ile Ala Tyr Thr Leu Ser Leu Leu Ala Gly
            275                 280                 285

Ser Leu Thr Pro Thr Asn Gly Thr Ser Leu Asn Ile Ala Asp Ala Ala
        290                 295                 300

Ser Leu Phe Thr Asn Trp Asn Arg Ile Thr Ala Val Thr Met Pro Glu
305                 310                 315                 320

Ile Ser Val Pro Val Leu Cys Trp Pro Gly Arg Leu Gln Leu Asp Ala
                325                 330                 335

Lys Val Glu Asn Pro Glu Ala Gly Gln Tyr Met Gly Asn Ile Asn Val
            340                 345                 350

Thr Phe Thr Pro Ser Ser Gln Thr Leu
        355                 360

<210> SEQ ID NO 29
<211> LENGTH: 359
<212> TYPE: PRT
<213> ORGANISM: Artificial Sequence
<220> FEATURE:
<223> OTHER INFORMATION: ETEC Protein Homology Sequence

<400> SEQUENCE: 29

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
```

```
                145                 150                 155                 160
Glu Leu Asn Lys Leu Pro Phe Gly Gly Val Trp Asn Ala Val Leu Lys
                165                 170                 175

Leu Asn Val Lys Arg Arg Tyr Thr Thr Tyr Gly Thr Tyr Thr Ile Asn
                180                 185                 190

Ile Thr Val Asn Leu Thr Asp Lys Gly Asn Ile Gln Ile Trp Leu Pro
                195                 200                 205

Gln Phe Lys Ser Asn Ala Arg Val Asp Leu Asn Leu Arg Pro Thr Gly
                210                 215                 220

Gly Gly Thr Tyr Ile Gly Arg Asn Ser Val Asp Met Cys Phe Tyr Asp
225                 230                 235                 240

Gly Tyr Ser Thr Met Ser Ser Ser Leu Glu Ile Arg Phe Gln Asp Asp
                245                 250                 255

Asn Ser Lys Ser Asp Gly Lys Phe Tyr Leu Lys Lys Ile Asn Asp Asp
                260                 265                 270

Ser Lys Glu Leu Val Tyr Thr Leu Ser Leu Leu Leu Ala Gly Lys Asn
                275                 280                 285

Leu Thr Pro Thr Asn Gly Gln Ala Leu Asn Ile Asn Thr Ala Ser Leu
                290                 295                 300

Glu Thr Asn Trp Asn Arg Ile Thr Ala Val Thr Met Pro Glu Ile Ser
305                 310                 315                 320

Val Pro Val Leu Cys Trp Pro Gly Arg Leu Gln Leu Asp Ala Lys Val
                325                 330                 335

Lys Asn Pro Glu Ala Gly Gln Tyr Met Gly Asn Ile Lys Ile Thr Phe
                340                 345                 350

Thr Pro Ser Ser Gln Thr Leu
                355

<210> SEQ ID NO 30
<211> LENGTH: 364
<212> TYPE: PRT
<213> ORGANISM: Artificial Sequence
<220> FEATURE:
<223> OTHER INFORMATION: ETEC Protein Homology Sequence

<400> SEQUENCE: 30

Met Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
                20                  25                  30

Thr Phe Ser Ile Gly Pro Ile Asp Arg Ser Ala Ala Ala Ser Tyr Pro
            35                  40                  45

Ala His Tyr Ile Phe His Glu Asx Val Ala Gly Tyr Asn Lys Asp His
        50                  55                  60

Ser Leu Phe Asp Arg Met Thr Phe Leu Cys Met Ser Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
                100                 105                 110

Lys Thr Leu Asn Leu Lys Gly Tyr Lys Arg Phe Leu Tyr Glu Ser Asp
            115                 120                 125

Arg Cys Ile His Tyr Val Asp Lys Met Asn Leu Asn Ser His Thr Val
        130                 135                 140

Lys Cys Val Gly Ser Phe Thr Arg Gly Val Asp Phe Thr Leu Tyr Ile
```

-continued

```
                145                 150                 155                 160
Pro Gln Gly Glu Ile Asp Gly Leu Leu Thr Gly Gly Ile Trp Lys Ala
                165                 170                 175

Thr Leu Glu Leu Arg Val Lys Arg His Tyr Asp Tyr Asn His Gly Thr
            180                 185                 190

Tyr Lys Val Asn Ile Thr Val Asp Leu Thr Lys Gly Asn Ile Gln
        195                 200                 205

Val Trp Thr Pro Lys Phe His Ser Asp Pro Arg Ile Asp Leu Asn Leu
    210                 215                 220

Arg Pro Glu Gly Asn Gly Lys Tyr Ser Gly Ser Asn Val Leu Glu Met
225                 230                 235                 240

Cys Leu Tyr Asp Gly Tyr Ser Thr His Ser Gln Ser Ile Glu Met Arg
                245                 250                 255

Phe Gln Asp Asp Ser Gln Thr Gly Asn Asn Glu Tyr Asn Leu Ile Lys
                260                 265                 270

Thr Gly Glu Pro Leu Lys Lys Leu Pro Tyr Lys Leu Ser Leu Leu Leu
            275                 280                 285

Gly Gly Arg Glu Phe Tyr Pro Asn Asn Gly Lys Ala Phe Thr Ile Asn
        290                 295                 300

Asp Thr Ser Ser Leu Phe Ile Asn Trp Asn Arg Ile Lys Ser Val Ser
305                 310                 315                 320

Leu Pro Gln Ile Ser Ile Pro Val Leu Cys Trp Pro Ala Asn Leu Thr
                325                 330                 335

Phe Met Ser Glu Leu Asn Asn Pro Glu Ala Gly Glu Tyr Ser Gly Ile
                340                 345                 350

Leu Asn Val Thr Phe Thr Pro Ser Ser Ser Leu
            355                 360

<210> SEQ ID NO 31
<211> LENGTH: 362
<212> TYPE: PRT
<213> ORGANISM: Artificial Sequence
<220> FEATURE:
<223> OTHER INFORMATION: ETEC Protein Homology Sequence

<400> SEQUENCE: 31

Met Lys Lys Ile Phe Ile Phe Leu Ser Ile Ile Phe Ser Ala Val Val
  1               5                  10                  15

Ser Ala Gly Arg Tyr Pro Glu Thr Thr Val Gly Asn Leu Thr Lys Ser
                20                  25                  30

Phe Gln Ala Pro Arg Leu Asp Arg Ser Val Gln Ser Pro Ile Tyr Asn
            35                  40                  45

Ile Phe Thr Asn His Val Ala Gly Tyr Ser Leu Ser His Ser Leu Tyr
        50                  55                  60

Asp Arg Ile Val Phe Leu Cys Thr Ser Ser Asn Pro Val Asn Gly
 65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Ile Ala Gly Asn Lys Lys Pro Ile Trp Glu Asn Gln Ser Cys Asp
        115                 120                 125

Phe Ser Asn Ile Met Val Leu Asn Ser Lys Ser Trp Ser Cys Gly Ala
    130                 135                 140

His Gly Asn Ala Asn Gly Thr Ile Leu Asn Leu Tyr Ile Pro Ala Gly
```

-continued

```
            145                 150                 155                 160
Glu Ile Asn Lys Leu Pro Phe Gly Gly Ile Trp Glu Ala Thr Leu Ile
                165                 170                 175
Leu Arg Leu Ser Arg Tyr Gly Glu Val Ser Ser Thr His Tyr Gly Asn
            180                 185                 190
Tyr Thr Val Asn Ile Thr Val Asp Leu Thr Asp Lys Gly Asn Ile Gln
            195                 200                 205
Val Trp Leu Pro Gly Phe His Ser Asn Pro Arg Val Asp Leu Asn Leu
    210                 215                 220
Arg Pro Ile Gly Asn Tyr Lys Tyr Ser Gly Ser Asn Ser Leu Asp Met
225                 230                 235                 240
Cys Phe Tyr Asp Gly Tyr Ser Thr Asn Ser Asp Ser Met Val Ile Lys
                245                 250                 255
Phe Gln Asp Asp Asn Pro Thr Asn Ser Ser Glu Tyr Asn Leu Tyr Lys
                260                 265                 270
Ile Gly Gly Thr Glu Lys Leu Pro Tyr Ala Val Ser Leu Ile Gly Glu
                275                 280                 285
Lys Ile Phe Tyr Pro Val Asn Gly Gln Ser Phe Thr Ile Asn Asp Ser
            290                 295                 300
Ser Val Leu Glu Thr Asn Trp Asn Arg Val Thr Ala Val Ala Met Pro
305                 310                 315                 320
Glu Val Asn Val Pro Val Leu Cys Trp Pro Ala Arg Leu Leu Leu Asn
                325                 330                 335
Ala Asp Val Asn Ala Pro Asp Ala Gly Gln Tyr Ser Gly Gln Ile Tyr
            340                 345                 350
Ile Thr Phe Thr Pro Ser Val Glu Asn Leu
            355                 360

<210> SEQ ID NO 32
<211> LENGTH: 353
<212> TYPE: PRT
<213> ORGANISM: Artificial Sequence
<220> FEATURE:
<223> OTHER INFORMATION: ETEC Protein Homology Sequence

<400> SEQUENCE: 32

Met Ser Asn Ile Cys Lys Trp Thr Ser Met Thr Ala His Trp Ser Ala
1               5                   10                  15
Ile Ile Asn Phe Ile Arg Lys Tyr Val Tyr Pro Ala Arg Ile Ile Ala
                20                  25                  30
Ile Leu Ala Gly Ala Thr Leu Pro Gln Val Ala Asp Ala Ile Thr Val
            35                  40                  45
Asp Leu Asn Tyr Asp Lys Asn Asn Val Ala Val Ile Thr Pro Val Trp
    50                  55                  60
Ser Gln Glu Trp Ser Val Ala Asn Val Leu Gly Gly Trp Val Cys Arg
65                  70                  75                  80
Ser Asn Arg Asn Glu Asn Glu Gly Cys Glu Glu Thr His Leu Val Trp
                85                  90                  95
Trp Tyr Ala Phe Gly Ala Tyr Ser Ile Arg Leu Arg Phe Arg Glu Gln
                100                 105                 110
Ile Ser His Ala Glu Ile Thr Leu Ile Leu Gly Ser Val Arg Asp
            115                 120                 125
Ala Cys Thr Gly Val Ile Asn Met Asn Ala Ala Cys Gln Trp Gly
    130                 135                 140
Arg Ser Leu Lys Leu Arg Ile Pro Ser Glu Glu Leu Ala Lys Ile Pro
```

```
                    145                 150                 155                 160
Thr Ser Gly Thr Trp Lys Ala Thr Leu Val Leu Asp Tyr Leu Gln Trp
                165                 170                 175

Gly Gly Asp Asp Pro Leu Gly Thr Ser Thr Thr Asp Ile Thr Leu Asn
            180                 185                 190

Val Thr Asp His Phe Ala Glu Asn Ala Ala Ile Tyr Phe Pro Gln Phe
        195                 200                 205

Gly Thr Ala Thr Pro Arg Val Asp Leu Asn Leu His Arg Met Asn Ala
    210                 215                 220

Ser Gln Met Ser Gly Arg Ala Asn Leu Asp Met Cys Leu Tyr Asp Gly
225                 230                 235                 240

Gly Val Lys Ala Arg Ser Leu Gln Met Met Glu Gly Ser Asn Lys Ser
                245                 250                 255

Gly Thr Gly Phe Gln Val Ile Lys Ser Asp Ser Ala Asp Thr Ile Asp
            260                 265                 270

Tyr Ala Val Ser Met Asn Tyr Gly Gly Arg Ser Ile Pro Val Thr Arg
        275                 280                 285

Gly Val Glu Phe Ser Leu Asp Asn Val Asp Lys Ala Ala Thr Arg Pro
    290                 295                 300

Val Val Leu Pro Gly Gln Arg Gln Ala Val Arg Cys Val Pro Val Pro
305                 310                 315                 320

Leu Thr Leu Thr Thr Gln Pro Phe Asn Ile Arg Glu Lys Arg Ser Gly
                325                 330                 335

Glu Tyr Gln Gly Thr Leu Thr Val Thr Met Leu Met Gly Thr Gln Thr
            340                 345                 350

Pro

<210> SEQ ID NO 33
<211> LENGTH: 165
<212> TYPE: PRT
<213> ORGANISM: Artificial Sequence
<220> FEATURE:
<223> OTHER INFORMATION: ETEC Protein Homology Sequence

<400> SEQUENCE: 33

Met Lys Leu Lys Lys Thr Ile Gly Ala Met Ala Leu Thr Thr Met Phe
1               5                   10                  15

Val Ala Met Ser Ala Ser Ala Val Glu Lys Asn Ile Thr Val Thr Ala
            20                  25                  30

Ser Val Asp Pro Thr Ile Asp Ile Leu Gln Ala Asp Gly Ser Ser Leu
        35                  40                  45

Pro Thr Ala Val Glu Leu Thr Tyr Ser Pro Ala Ala Ser Arg Phe Glu
    50                  55                  60

Asn Tyr Lys Ile Ala Thr Lys Val His Thr Asn Val Ile Asn Lys Asn
65                  70                  75                  80

Val Leu Val Lys Leu Val Asn Asp Pro Lys Leu Thr Asn Val Leu Asp
                85                  90                  95

Ser Thr Lys Gln Leu Pro Ile Thr Val Ser Tyr Gly Gly Lys Leu Ser
            100                 105                 110

Thr Ala Asp Val Thr Phe Glu Pro Ala Glu Leu Asn Phe Gly Thr Ser
        115                 120                 125

Gly Val Thr Gly Val Ser Ser Gln Asp Leu Val Ile Gly Ala Thr
    130                 135                 140

Thr Ala Gln Ala Pro Ser Ala Asn Tyr Ser Gly Val Val Ser Ile Leu
145                 150                 155                 160
```

Met Thr Leu Ala Ser
            165

<210> SEQ ID NO 34
<211> LENGTH: 168
<212> TYPE: PRT
<213> ORGANISM: Artificial Sequence
<220> FEATURE:
<223> OTHER INFORMATION: ETEC Protein Homology Sequence

<400> SEQUENCE: 34

Met Lys Phe Lys Lys Thr Ile Gly Ala Met Ala Leu Thr Thr Met Phe
1               5                   10                  15

Val Ala Val Ser Ala Ser Ala Val Glu Lys Asn Ile Thr Val Thr Ala
            20                  25                  30

Ser Val Asp Pro Ala Ile Asp Leu Leu Gln Ala Asp Gly Asn Ala Leu
        35                  40                  45

Pro Ser Val Lys Leu Ala Tyr Ser Pro Ala Ser Lys Ile Phe Glu Ser
    50                  55                  60

Tyr Arg Val Met Thr Gln Val His Thr Asn Asp Ala Thr Lys Lys Val
65                  70                  75                  80

Ile Val Lys Leu Ala Asp Thr Pro Gln Leu Thr Asp Val Leu Asn Ser
                85                  90                  95

Thr Val Gln Met Pro Ile Ser Val Ser Trp Gly Gly Val Leu Ser Thr
            100                 105                 110

Thr Ala Lys Glu Phe Glu Ala Ala Ala Leu Gly Tyr Ser Ala Ser Gly
        115                 120                 125

Val Asn Gly Val Ser Ser Gln Glu Leu Val Ile Ser Ala Ala Pro
    130                 135                 140

Lys Thr Ala Gly Thr Ala Pro Thr Ala Gly Asn Tyr Ser Gly Val Val
145                 150                 155                 160

Ser Leu Val Met Thr Leu Gly Ser
            165

<210> SEQ ID NO 35
<211> LENGTH: 170
<212> TYPE: PRT
<213> ORGANISM: Artificial Sequence
<220> FEATURE:
<223> OTHER INFORMATION: ETEC Protein Homology Sequence

<400> SEQUENCE: 35

Met Lys Leu Lys Lys Thr Ile Gly Ala Met Ala Leu Ala Thr Leu Phe
1               5                   10                  15

Ala Thr Met Gly Ala Ser Ala Val Glu Lys Thr Ile Ser Val Thr Ala
            20                  25                  30

Ser Val Asp Pro Thr Val Asp Leu Leu Gln Ser Asp Gly Ser Ala Leu
        35                  40                  45

Pro Asn Val Ala Leu Thr Tyr Ser Pro Ala Val Asn Asn Phe Glu Ala
    50                  55                  60

His Thr Ile Asn Thr Val His Thr Asn Ser Asp Lys Gly Val
65                  70                  75                  80

Val Val Lys Leu Ser Ala Asp Pro Val Leu Ser Asn Val Leu Asn Pro
                85                  90                  95

Thr Leu Gln Ile Pro Val Ser Val Asn Phe Ala Gly Lys Pro Leu Ser
            100                 105                 110

Thr Thr Gly Ile Thr Ile Asp Ser Asn Asp Leu Asn Phe Ala Ser Ser

-continued

```
                115                 120                 125
Gly Val Asn Tyr Val Ser Ser Thr Gln Lys Leu Ser Ile His Ala Asp
            130                 135                 140

Ala Thr Arg Val Thr Gly Gly Ala Leu Thr Ala Gly Gln Tyr Gln Gly
145                 150                 155                 160

Leu Val Ser Ile Ile Leu Thr Lys Ser Thr
                165                 170
```

<210> SEQ ID NO 36
<211> LENGTH: 170
<212> TYPE: PRT
<213> ORGANISM: Artificial Sequence
<220> FEATURE:
<223> OTHER INFORMATION: ETEC Protein Homology Sequence

<400> SEQUENCE: 36

```
Met Lys Leu Asn Lys Ile Ile Gly Ala Leu Val Leu Ser Ser Thr Phe
1               5                   10                  15

Val Ser Met Gly Ala Ser Ala Ala Glu Lys Asn Ile Thr Val Thr Ala
            20                  25                  30

Ser Val Asp Pro Thr Ile Asp Leu Met Gln Ser Asp Gly Thr Ala Leu
        35                  40                  45

Pro Ser Ala Val Asn Ile Ala Tyr Leu Pro Gly Glu Lys Arg Phe Glu
    50                  55                  60

Ser Ala Arg Ile Asn Thr Gln Val His Thr Asn Asn Lys Thr Lys Gly
65                  70                  75                  80

Ile Gln Ile Lys Leu Thr Asn Asp Asn Val Val Met Thr Asn Leu Ser
                85                  90                  95

Asp Pro Ser Lys Thr Ile Pro Leu Glu Val Ser Phe Ala Gly Thr Lys
            100                 105                 110

Leu Ser Thr Ala Ala Thr Ser Ile Thr Ala Asp Gln Leu Asn Phe Gly
        115                 120                 125

Ala Ala Gly Val Glu Thr Val Ser Ala Thr Lys Glu Leu Val Ile Asn
    130                 135                 140

Ala Gly Ser Thr Gln Gln Thr Asn Ile Val Ala Gly Asn Tyr Gln Gly
145                 150                 155                 160

Leu Val Ser Ile Val Leu Thr Gln Glu Pro
                165                 170
```

<210> SEQ ID NO 37
<211> LENGTH: 168
<212> TYPE: PRT
<213> ORGANISM: Artificial Sequence
<220> FEATURE:
<223> OTHER INFORMATION: ETEC Protein Homology Sequence

<400> SEQUENCE: 37

```
Met Lys Leu Lys Tyr Thr Ile Gly Ala Met Ala Leu Ser Thr Ile Phe
1               5                   10                  15

Val Ala Val Ser Ala Ser Ala Val Glu Lys Asn Ile Thr Val Thr Ala
            20                  25                  30

Ser Val Asp Pro Thr Ile Asp Ile Leu Gln Ala Asn Gly Ser Ala Leu
        35                  40                  45

Pro Thr Ala Val Asp Leu Thr Tyr Leu Pro Gly Ala Lys Thr Phe Glu
    50                  55                  60

Asn Tyr Ser Val Leu Thr Gln Ile Tyr Thr Asn Asp Pro Ser Lys Gly
65                  70                  75                  80
```

```
Leu Asp Val Arg Leu Val Asp Thr Pro Lys Leu Thr Asn Ile Leu Gln
            85                  90                  95

Pro Thr Ser Thr Ile Pro Leu Thr Val Ser Trp Ala Gly Arg Thr Leu
            100                 105                 110

Ser Thr Ser Ala Gln Lys Ile Ala Val Gly Asp Leu Gly Phe Gly Ser
            115                 120                 125

Thr Gly Thr Ala Gly Val Ser Asn Ser Lys Glu Leu Val Ile Gly Ala
            130                 135                 140

Thr Thr Ser Gly Lys Pro Ser Ala Gly Lys Tyr Gln Gly Val Val Ser
145                 150                 155                 160

Ile Val Met Thr Gln Ser Thr Asn
            165
```

<210> SEQ ID NO 38
<211> LENGTH: 142
<212> TYPE: PRT
<213> ORGANISM: Artificial Sequence
<220> FEATURE:
<223> OTHER INFORMATION: ETEC Protein Homology Sequence

<400> SEQUENCE: 38

```
Val Asp Pro Thr Ile Asp Ile Leu Gln Ala Asn Gly Ser Ala Leu Pro
1               5                   10                  15

Thr Ala Val Asp Leu Thr Tyr Leu Pro Gly Ala Lys Thr Phe Glu Asn
            20                  25                  30

Tyr Ser Val Leu Thr Gln Ile Tyr Thr Asn Asp Pro Ser Lys Gly Leu
            35                  40                  45

Asp Val Arg Leu Val Asp Thr Pro Lys Leu Thr Asn Ile Leu Gln Pro
50                  55                  60

Thr Ser Thr Ile Pro Leu Thr Val Ser Trp Ala Gly Lys Thr Leu Ser
65                  70                  75                  80

Thr Ser Ala Gln Lys Ile Ala Val Gly Asp Leu Gly Phe Gly Ser Thr
            85                  90                  95

Gly Thr Ala Gly Val Ser Asn Ser Lys Glu Leu Val Ile Gly Ala Thr
            100                 105                 110

Thr Ser Gly Thr Ala Pro Ser Ala Gly Lys Tyr Gln Gly Val Val Ser
            115                 120                 125

Ile Val Met Thr Gln Ser Thr Asp Thr Ala Ala Pro Val Pro
            130                 135                 140
```

<210> SEQ ID NO 39
<211> LENGTH: 133
<212> TYPE: PRT
<213> ORGANISM: Artificial Sequence
<220> FEATURE:
<223> OTHER INFORMATION: ETEC Protein Homology Sequence

<400> SEQUENCE: 39

```
Val Asp Pro Lys Leu Asp Leu Leu Gln Ala Asp Gly Thr Ser Leu Pro
1               5                   10                  15

Asp Ser Ile Ala Leu Thr Tyr Ser Ala Ser Asn Asn Phe Glu Val
            20                  25                  30

Tyr Ser Leu Asn Thr Ala Ile His Thr Asn Asp Lys Thr Lys Ala Val
            35                  40                  45

Val Val Lys Leu Ser Ala Pro Ala Val Leu Ser Asn Ile Met Lys Pro
50                  55                  60

Ser Ser Gln Ile Pro Met Lys Val Thr Leu Gly Gly Lys Thr Leu Ser
65                  70                  75                  80
```

```
Thr Ala Asp Ala Glu Phe Ala Ala Asp Thr Leu Asn Phe Gly Ala Ser
                85                  90                  95

Gly Val Glu Asn Val Ser Ser Val Gln Gln Leu Thr Ile His Ala Glu
            100                 105                 110

Ala Ala Pro Pro Glu Ala Gly Asn Tyr Gln Gly Val Ile Ser Leu Ile
            115                 120                 125

Met Thr Gln Lys Thr
    130

<210> SEQ ID NO 40
<211> LENGTH: 134
<212> TYPE: PRT
<213> ORGANISM: Artificial Sequence
<220> FEATURE:
<223> OTHER INFORMATION: ETEC Protein Homology Sequence

<400> SEQUENCE: 40

Val Asp Pro Lys Leu Asp Leu Leu Gln Ala Asp Gly Thr Ser Leu Pro
 1               5                  10                  15

Asp Ser Ile Ala Leu Thr Tyr Ser Ser Ala Ser Asn Asn Phe Glu Val
             20                  25                  30

Tyr Ser Leu Asn Thr Ala Ile His Thr Asn Asp Lys Ser Lys Gly Val
             35                  40                  45

Val Val Lys Leu Ser Ala Ser Pro Val Leu Ser Asn Ile Met Pro Asn
    50                  55                  60

Ser Gln Ile Pro Met Lys Val Thr Leu Gly Gly Glu Thr Leu Asn Thr
65                  70                  75                  80

Thr Asp Thr Glu Phe Thr Val Asp Thr Leu Asn Phe Gly Thr Ser Gly
                85                  90                  95

Val Glu Asn Val Ser Ser Thr Gln Gln Leu Thr Ile His Ala Asp Thr
            100                 105                 110

Gln Gly Thr Ala Pro Glu Ala Gly Asn Tyr Gln Gly Ile Ile Ser Leu
            115                 120                 125

Ile Met Thr Gln Lys Thr
    130
```

ISOLATION AND CHARACTERIZATION OF THE *CSA* OPERON (ETEC-CS4 PILI) AND METHODS OF USING SAME

CROSS-REFERENCE TO RELATED APPLICATIONS

This Application is a Divisional of U.S. application Ser. No. 09/839,894, filed Apr. 20, 2001; issued as U.S. Pat. No. 6,902,736 which in turn claims priority to U.S. Provisional Patent Application No. 60/198,626, filed Apr. 20, 2000; the disclosure of each of which is hereby incorporated by reference in its entirety.

BACKGROUND OF THE INVENTION

1. Field of the Invention

The disclosed invention relates to the isolation and characterization of the csa operon, which encodes the CS4 pili and its use as an immunogenic agent with utility in preventing ETEC colonization of a subject.

2. Description of the Related Art

Human ETEC strains are a major cause of diarrhea in infants and young children in developing countries (Black et al., *Lancet*, I: 141-143 (1981); Levine, *J. Infect. Dis.*, 155: 377-389 (1987); Qadri, et al., *J. Clin. Microbiol.*, 38:27-31 (2000)), which account for a high rate of infantile morbidity and mortality. Human ETEC strains are also a major cause of travelers' diarrhea. (Black, *Rev. Infect. Dis.*, 8S:S131-S135 (1986); DuPont et al., *N. Engl. J. Med.*, 285:1520-1521 (1976); Hyams et al., *N. Engl. J. Med.*, 325:1423-1428 (1991); Merson, et al., *N. Engl. J. Med.*, 294:1299-1305 (1976)). ETEC infection is characterized by watery diarrhea often accompanied by low-grade fever, abdominal cramps, malaise and vomiting.

ETEC strains colonize the small bowel lumen by means of surface pili called colonization factor antigens (CFA), and coli surface antigens (CS), and cause diarrhea through the action of heat labile (LT) and/or heat stable (ST) enterotoxins. ETEC fimbriae are proteinaceous filaments exhibiting different morphologies such as rigid rod like shapes of 2-7 nm in diameter, fibrilar thin flexible wiry structures, or bundles. (Gaastra et al., *Trends. Microbiol.*, 4:444-452 (1996)).

Human ETEC strains display a variety of over 20 serologically distinct pili on their cell surfaces. The most common human ETEC strains express CFA/I, CFA/II and CFA/IV (Levine, et al., "Fimbrial vaccines," In P. Klemm (ed.), *Fimbriae: adhesion, biogenics, genetics and vaccines*, Boca Raton: CRC Press, 1994; McConnell, et al., *Epidemiol. Infect.*, 106: 477-484 (1991)). CFA/I produces a single type of fimbriae, while CFA/II and CFA/IV strains produce several types of coli surface antigens. CFA/II strains express CS1, CS2 and CS3; and CFA/IV strains (originally called PCF8775) express the nonpilus antigen CS6 either alone or together with CS4 or CS5 fimbria. (McConnell, et al., *Infect. Immun.*, 56:1974-1980 (1988); McConnell, et al., *FEMS Microbiol. Lett.*, 52:105-108 (1989); Svennerholm, et al., *Infect. Immun.*, 56:523-528 (1988); Thomas, et al., *J. Gen. Microbiol.*, 131:2319-2326 (1985)). The occurrence of CS4+ CS6+producing strains is restricted to serotype O25:H42. (McConnell, et al., *Infect. Immun.*, 56:1974-1980 (1988); Willshaw, et al., *FEMS Microbiol. Lett.*, 49:473-478 (1988); Willshaw, et al., *FEMS Microbiol. Lett.*, 56:255-260 (1990); Willshaw, et al., *FEMS Microbiol. Lett.*, 66:125-129 (1991)).

The CS4 pili is rigid, 7 nm in diameter, and is composed of subunits with a molecular mass of 17.0 kDa. (Knutton, et al., *Infect. Immun.*, 57:3364-3371 (1989); McConnell, et al., *Infect. Immun.*, 56:1974-1980 (1988); Wolf, et al., *Infect. Immun.*, 57:164-173 (1989)). Because of their epidemiological importance and due to the fact that cross protection does not occur between strains of ETEC expressing different fimbriae, at least these CFA/I and CS1—CS6 fimbrial types must be included in a broad spectrum ETEC vaccine, (Gaastra et al., *Trends. Microbiol.*, 4:444-452 (1996); Levine, *J. Pediatr. Gastroenterol. Nutr.*, In Press (2000); Levine, et al., "Fimbrial vaccines," In P. Klemm (ed.), *Fimbriae: adhesion, biogenics, genetics and vaccines*, Boca Raton: CRC Press, 1994). Of these seven important fimbriae, only the genes encoding CS4 have not been cloned and sequenced.

The genes that are required for the expression of functional pili are characteristically linked in gene clusters (Sakellaris and Scott, *Mol. Microbiol.*, 30:681-687 (1998)), and consist of the structural genes, assembly cassette genes and regulatory genes. The assembly cassette genes include chaperone and usher genes. The chaperone protein is thought to bind to fimbrial subunit proteins in the periplasmic space and prevent premature folding and degradation. The usher proteins are outer membrane proteins that serve as pores for the transport and assembly of the fimbriae. The structural gene encodes for the pilin protein that forms the fimbriae that is composed of repeated subunits of the pilin protein. Some fimbriae such as, CFA/I, CS1 and CS2, contain a minor pilin protein which is associated with the pili tip, that is probably involved in the attachment of the bacteria to the cell receptors. (Sakellaris, et al., *Proc. Natl. Acad. Sci. U.S.A.*, 96:12828-12832 (1999)). Fimbria expression is controlled by genes such as rns and cfaD that are similar to the araC family of transcriptional regulators that positively regulate transcription. (Grewal et al., *Vaccine*, 11:221-226 (1993); de Haan et al., *FEMS Microbiol. Lett.*, 67:341-346 (1991); 19, 21, Savelkoul, et al., *Microb. Pathog.*, 8:91-99 (1990)).

Genes encoding ETEC fimbriae have been located on large plasmids [CFA/I, (Hamers et al., *Microb. Pathog.*, 6:297-309 (1989); 20); CS1, (Froehlich et al., *Mol. Microbiol.*, 12:387-401 (1994)); CS3, (Jalajakumari, et al., *Mol. Microbiol.*, 3:1685-1695 (1989), Manning, et al., *Mol. Gen. Genet.*, 200: 322-327 (1985)); CS5, (Duthy, et al., *J. Bacteriol.*, 181:5847-5851 (1999)) and CS6, (Wolf, et al., *FEMS Microbiol. Lett.*, 148:35-42 (1997))], or on the chromosome [CS2, (Froehlich et al., *Mol. Microbiol.*, 12:387-401 (1994), Froehlich et al., *Infect. Immun.*, 63:4849-4856 (1995))]. Early experiments to locate the CS4 encoding genes revealed disparate results without conclusive localization, (Sommerfelt, et al., *Microb. Pathog.*, 11:297-304 (1991); Sommerfelt, et al., *Infect. Immun.*, 60:3799-3806 (1992); Sommerfelt, et al., *J. Clin. Microbiol.*, 30:1823-1828 (1992); Willshaw, et al., *FEMS Microbiol. Lett.*, 56:255-260 (1990); Wolf, et al., *Infect. Immun.*, 57:164-173 (1989)).

Because the attachment of ETEC strains to intestinal cells is crucial for establishment of infection, the prevention of disease is based mainly upon immune responses against the pili that interfere with the attachment process. Studies performed with 14 healthy human volunteers who ingested $5 \times 10^8$ *E. coli* E24377A (O139:H28), a CS1 and CS3 producing strain, showed that all 14 became colonized, 9 developed a typical diarrheal syndrome, and 6 of these ill persons manifested a significant increase in serum IgG antibody to purified CS1 and CS3 antigens. Levine, M. M., et al., *Infect. Immun.*, 44:409-420 (1984). These results suggest that the fimbria play a role in pathogenesis, and stimulate an immune response.

Passive protection against ETEC infection was demonstrated in a clinical trial done at the University of Maryland, which demonstrated that oral prophylaxis with hyperimmune anti CFA/I immunoglobulin provided 90% protection against diarrhea caused by oral challenge with $10^9$ cfu of ETEC strain H10407, a CFA/I producing strain. Tacket, et al., N. Eng. J. Med., 318: 1240 (1988). In another study oral immunization with purified CS1 and CS3 antigens encapsulated in biodegradable polymer microspheres were used to induce the development of IgA anti CS ASC (Antibody Secreting Cells) and jejunal fluid secretory IgA anti CS in 50% of the vaccinees. Levine, et al., Fimbriae (pili) adhesions as vaccines, in *Protein-Carbohydrate Interactions in Biological Systems. The molecular Biology of Microbial Pathogenicity*, Lark, et al., Eds., Academic Press, London, p 154, 1986. This exposure also protected 30% of vaccinees from diarrhea following challenge with the virulent ETEC E24377A (CS1$^+$CS3$^+$LT$^+$ST$^+$) strain. A protective efficacy of 75% was demonstrated by immunization with the attenuated ETEC strain. Feeding volunteers with $5 \times 10^{10}$ live *E. coli* E1392-75-2A (O6:H16) a CS1$^+$ CS3$^+$ LT$^-$ ST$^-$ strain, induced significant rise in intestinal fluid secretory IgA antibodies to CS1 and CS3 fimbria, and conferred protection to 9/12 volunteers that were challenged with a virulent heterologous serotype strain ETEC E24377A (O139:H28).

Another approach to develop an ETEC vaccine is to immunize with killed mixed ETEC strains. This type of vaccine is based on the fact that prior infection with an ETEC strain elicits protective immunity against a clinical illness that might be caused from subsequent exposure to the homologous strain. Oral immunization of children and adult volunteers with such a vaccine resulted in significant intestinal IgA responses against the CFA and CS components of the various strains. The vaccine induced high level of intestinal IgA antibody, IgA antibody ASC in the blood, and serum antibodies towards the colonization factor antigens. Jertborn, et al., Vaccine 16:255 (1997). Those results indicate that antibodies towards ETEC pilis provide protection against diarrhea caused by ETEC strains.

A combined vaccine against diarrheal disease caused by *Shigella*, *Salmonella* and ETEC has been proposed. These vaccines are composed of live attenuated *Shigella* or *Salmonella* strains that express ETEC fimbriae. The recombinant bacteria colonize the intestine and induced the mucosal and systemic immune response against the bacteria and the pili. Noriega et al., (*Infect. Immun.*, 64:23-27 (1996)) co-expressed CFA/I and CS3 in *Shigella* CVD1203, immunized guinea pigs and mice, and showed that the immunized animals developed high titer of tears secreted IgA (similar to mucosal sIgA), and serum IgG antibodies, towards the *Shigella* LPS and the fimbrial antigens. The ETEC human recombinant LT (K63) gene was expressed in *Shigella* CVD1204, a guanine dependent strain, and showed production of sIgA and serum IgG toward the *Shigella* LPS as well as towards the LT-A and LT-B subunits of the LT enterotoxin, following immunization of guinea pigs. Koprowski, et al., (*Infect. Immun.*, 68:4884-92 (2000)) co-expressed in CVD1204 the CFA/I and LT (K63) antigens, and demonstrates production of antibodies of the sIgA and serum IgG toward the *Shigella* LPS, the CFA/I pili antigens and the LT antigens. Altboum et al, (Attenuated *Shigella flexneri* 2a ΔguaBA strain CVD 1204 expressing ETEC CS2 and CS3 fimbriae as a live mucosal vaccine against *Shigella* and enterotoxigenic *Escherichia coli* infection, In press) immunized guinea pigs with a mixture of CVD 1204 strains expressing ETEC CS2 and CS3 fimbria. All the immunized animals developed tears sIgA and serum IgG antibodies against *Shigella* LPS, CS2 and CS3 antigens, agglutinating antibodies against *Shigella* and ETEC CS2 and CS3 strains, and were protected against keratoconjunctivitis caused by eye challenge with the virulent *S. flexneri* 2a 2457T strain. Those results indicate that a combined immunization with live attenuated *Shigella* strains expressing ETEC fimbria might induce protection against Shigellosis and ETEC infection.

SUMMARY OF THE INVENTION

The disclosed invention relates to compositions and methods of using csa operon products and the nucleotide and amino acid sequences encoded thereby. One embodiment relates to an immunogenic composition comprising a recombinant product of a csa operon and a carrier. Various aspects of this embodiment relate to compositions in which the recombinant product of the csa operon is CsaA, CsaB, CsaC, CsaD, CsaE, or a product that is at least 95% homologous to any one of these csa operon products. Additionally, the recombinant product of the csa operon can comprise the csa operon itself.

Another embodiment relates to an isolated nucleotide sequence comprising a csa operon or a functional fragment thereof. Another embodiments relates to a purified polypeptide sequence expressed from a recombinant csa operon.

Also disclosed are various methods of using the csa operon, products, and fragments thereof. One embodiment teaches a method of generating an immune response, comprising providing an immunogenic composition to a subject, wherein the immunogenic composition comprises a csa operon, a functional fragment thereof, or product thereof, and contacting the subject with the immunogenic composition, whereby an immune response is generated in the subject.

Another embodiment relates to a method of producing a polypeptide product from a csa operon or functional fragment thereof, comprising providing the csa operon in an expression vector, introducing the expression vector into a host cell, such that a recombinant host cell is produced, and subjecting the recombinant host cell to conditions such that a protein from the csa operon is expressed.

Additional embodiments encompass cells containing recombinant the csa operon or fragments thereof and vectors comprising the csa operon or fragments thereof.

BRIEF DESCRIPTION OF THE DRAWINGS

FIG. 3. Alignment of the amino acid sequence of CsaE to other homologous proteins. The predicted amino acid sequence of CsaE (SEQ ID NO:28) based on the gene sequence was used in a BLAST search for other homologous proteins. CfaE (SEQ ID NO:29) is the tip adhesion moiety of CS2; CooD (SEQ ID NO:30) is the tip adhesion moiety of CS1; and TsaD (SEQ ID NO:31) is the adhesion protein from *Salmonella typhi*. CotD (SEQ ID NO:32) is the spore coat protein of *Bacillus subtilis*.

FIG. 4. Alignment of the amino acid sequence of CsaB to other ETEC fimbrial subunit proteins. The predicted amino acid sequence of CsaB (SEQ ID NO:33) based on the DNA sequence was used in a BLAST search to identify homologous proteins. The other fimbrial subunits were CfaA (SEQ ID NO:34), CooA (SEQ ID NO:35), CotA (SEQ ID NO:36), CsuA1 (SEQ ID NO:37), CsuA2 (SEQ ID NO:38), CsdA (SEQ ID NO:39), and CsbA (SEQ ID NO:40).

DETAILED DESCRIPTION OF THE PREFERRED EMBODIMENTS

Figure 1A:
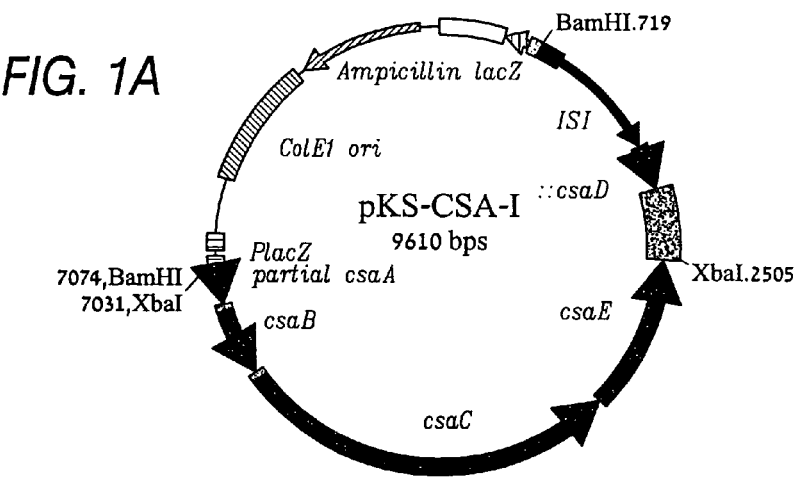
FIG. 1. Plasmid constructs containing the entire csa operon. Plasmid pKS-CSA-I contains the csaB, csaC, csaE, csaD' genes, and IS1 element, (1A). Plasmid pKS-CSA-II contains the csaA genes and upstream sequences flanked with IS21 element.(1B). Schematic representation of the csa operon, (1C). Scale, in base pairs. (1D).

The description below relates to the csa operon, which encodes the proteins required for the production of CS4 antigen, and the generation of immunogenic compositions containing products or fragments of the csa operon. Methods of making and using the disclosed immunogenic compositions are also described.

To generate the disclosed immunogenic compositions, the csa operon has been sequenced and cloned into an expression vector. The genes of the csa operon have been expressed in *Shigella* CVD1204, resulting in the production of CS4 in this recombinant organism. Preliminary results from immunization of guinea pigs with this recombinant strain indicate the development of an immune response against both *Shigella* and the CS4 pili. Accordingly, the work described herein relating to the csa operon is applicable to the formulation and administration of immunogenic compositions with activity against a variety of diseases.

Organization of the csa Operon

The csa operon is located on a DNA fragment of approximately ten (10) kilobases in length. The operon comprises 5 genes that are flanked on both sides by insertion elements. This structure is similar to the pathogenicity island described in FIG. 1.

From the entire fragment, 7245 base pairs were sequenced on both strands and the data are presented in FIG. 2. The size of the csa operon was found to be approximately 6099 base pairs in length and encompasses five open reading frames.

Sequence homology to genes encoding the subunits of other ETEC fimbriae for which biochemical analysis is available indicates the following functions for each of the open reading frames. The csaA gene encodes the CsaA protein, which is hypothesized to be a periplasmic chaperon-like protein. The csaB gene encodes the CsaB protein, which is hypothesized to be the major pilin subunit. Amino terminal sequence analysis of the CS4 pilin subunit confirms the role for this gene. The csaC gene encodes the CsaC protein is hypothesized to be a membrane usher protein. The csaD gene encodes a truncated CsaD, which is hypothesized to be a regulatory protein. The csaE gene encodes the CsaE protein, which is hypothesized to be a tip-associated pilin protein. The amino acid sequences of the CsaA-E proteins are described in FIG. 3.

The location of the individual genes in the csa operon, and the properties of the CsaA-E proteins, are described in Table 1.

TABLE 1

Properties of the csa operon.

| Gene | Location (bp) | PRO | No. of AA | Calculated MW | Theoretical pI | Signal peptide, No. of AA |
|---|---|---|---|---|---|---|
| | | | properties of the CS4 proteins: | | | |
| csaA | 283-999 | CsaA | 238 | 27305.6 | 9.29 | 19 |
| csaB | 1028-1531 | CsaB | 167 | 17343.9 | 6.56 | 23 |
| csaC | 1589-4192 | CsaC | 867 | 97686.93 | 8.42 | 22 |
| csaE | 4196-5281 | CsaE | 361 | 40102.4 | 8.75 | 23 |
| csaD | 5790-6119 | CsaD | 109 | Missing the N-terminal 48 amino acids. | | |

The amino acid sequences of the CsaA-E proteins share homology to similar proteins from other ETEC fimbriae. A comparison of protein homologies is shown in Table 2.

TABLE 2

Homology of CsaA-E proteins to other ETEC fimbriae proteins.

| CS4 Pro | Pili | Protein | NCBI no. | Identities | Positive | Gaps |
|---|---|---|---|---|---|---|
| | Homology to: | | | | | |
| CsaA | CFA/I | CfaA | M55661 | 208/238 (87%) | 218/238 (91%) | |
| | CS1 | CooB | P25731 | 124/221 (56%) | 161/221 (72%) | 4/221 (1%) |
| | CS2 | CotB | S57934 | 111/238 (46%) | 157/238 (65%) | 3/238 (1%) |
| CsaB | CS4 | CsfA | X97493 | 109/134 (81%) | 110/134 (81%) | |
| | CFA/I | CfaB | P02971 | 99/170 (58%) | 122/170 (71%) | 3/170 (1%) |
| | CS14 | CsuA1 | X97491 | 95/164 (57%) | 116/164 (69%) | |
| | CS1 | CooA | P25730 | 85/168 (50%) | 108/168 (63%) | 4/168 (2%) |
| | CS2 | CotA | S57935 | 76/167 (45%) | 105/167 (62%) | 3/167 (1%) |
| | CS14 | CsuA2 | X97492 | 67/132 (50%) | 84/132 (62%) | 1/132 (1%) |
| | CS19 | CsdA | X97494 | 56/131 (42%) | 75/131 (56%) | 1/132 (0%) |
| | CS17 | CsbA | X97495 | 54/132 (40%) | 75/132 (55%) | 1/132 (0%) |
| CsaC | CFA/I | CfaC | P25733 | 800/868 (92%) | 821/868 (94%) | |
| | CS1 | CooC | S49538 | 531/841 (63%) | 659/841 (78%) | 3/841 (0%) |
| | CS2 | CotC | S57936 | 469/839 (55%) | 610/839 (71%) | 3/839 (0%) |
| CsaE | CFA/I | CfaE | P25734 | 268/361 (74%) | 293/361 (80%) | 1/361 (0%) |
| | CS1 | CooD | S49539 | 177/329 (59%) | 224/329 (67%) | 11/329 3%) |
| | CS2 | CotD | S57937 | 161/339 (47%) | 218/339 (63%) | 7/339 (2%) |
| CsaD | CFA/I | CfaD | P25393 | 90/101 (89%) | 98/101 (96%) | |
| | | RNS | P16114 | 89/101 (88%) | 98/101 (96%) | |
| | | CSVR | P3460 | 75/103 (72%) | 88/103 (84%) | |
| | AAF/I | AGGR | P43464 | 57/101 (56%) | | |

The csa operon encodes the synthesis of ETEC CS4 fimbriae. This operon was cloned from ETEC E11881A, a CS4 producer strain. A nucleic acid fragment comprising 7239 base pairs was sequenced (in both directions). The results indicate that the csa operon is located on a nucleic acid fragment 6095 base pairs in length. (Accession No. AF296132).

The sequence of the csa operon was analyzed. The analysis of the operon indicated that the csa operon encodes five proteins. These proteins are the fimbriae structural protein (CsaB), the tip associated protein (CsaE), a chaperon-like protein (CsaA), a usher-like protein (CsaC), and a truncated regulatory protein (CsaD).

The CsaB protein consist of 167 amino acids, (23 of which comprise a signal peptide), producing an ~17 kDa peptide. The amino acid sequence of the CsaB protein shares homology with other ETEC fimbriae proteins. For example, CsaB is 71% homologous to the CfaB protein of CFA/I, 69% and 62% homologous to the two CS14 structural proteins, 63% homologous to the CS1 structural protein, 62% homologous to the CS2 structural protein, 56% homologous to the CS19 structural protein, and 55% homologous to the CS17 structural protein.

The CsaE protein is believed to be a tip associated protein based on its homology to known tip proteins of other ETEC fimbriae. It is a protein of 361 amino acids, 23 amino acids of which are cleaved to produce a globular ~40 kDa protein. The amino acid sequence of the CsaE protein shares homology to CFA/I, CS1 and CS2 pili tip proteins, of 80%, 67% and 63%, respectively. The fimbrial assembly proteins CsaA and CsaC share homology to similar proteins from CFA/I, CS1 and CS2 pili.

CsaD is believed to be a regulatory protein based on its homology to other known ETEC regulatory proteins. Its 48 terminal amino acids were deleted as a result of an insertion of an IS1 element. In addition, two frame shift mutations following 100 amino acids resulted in a stop codon. ETEC CFA/I strain E7473 contains a truncated CfaD' like protein (144 amino acids out of 265), which also contains a stop codon and various frame shift mutations. (Jordi, et al., *DNA Seq.*, 2:257-263 (1992)). The position of the frame shift mutation in cfaD' (Accession AAC41418) is at the same region as in csaD'.

Upstream to the csaA gene (approximately 3.5 kb) there is an additional IS21 element, rendering the csa operon flanked between the two insertion elements, which is characteristic of a mobile structure. The size of this pathogenicity island-like structure is about 10,500 base pairs and its G+C ratio is lower than that of *E. coli* (38.8% versus 50.8%).

Other ETEC fimbrial operons are carried on similar mobile structures. The CS1 operon contains IS sequences on both sides (IS150 (Accession: X62495), and IS2 (Accession No.: X76908)(Froehlich, et al., *Mol. Microbiol.*, 12:387-401 (1994)). The CS2 operon contains at its upstream site IS3 and IS1 DNA sequences, (Accession No.: Z47800)(Froehlich, et al., *Infect. Immun.*, 63:4849-4856 (1995)). The CS6 pili contains IS elements, upstream IS91 and IS102, and downstream IS629 and IS3, (Accession U04844)(Wolf, et al., *FEMS Microbiol. Lett.*, 148:35-42 (1997)). The CS5 pili operon contains IS1 sequences at the upstream position that are 99% homologous to the IS1 sequences of the csa operon, and at its downstream site, IS30 sequences. (Accession AJ224079) (Duthy, et al., *J. Bacteriol.*, 181:5847-5851 (1999)).

The CS4 major fimbrial protein shares a high degree of amino acid sequence homology to CFA/I, CS 1 and CS2 fimbrial proteins. Cross-reaction between antibodies against CS4 and CFA/I, CS1, CS2, and CS17 fimbriae were described by McConnell et al 1989. (McConnell, et al., *FEMS Microbiol. Lett.*, 52:105-108 (1989)).

The high homology between the structural proteins of CS4 and CFA/I fimbriae resulted in antibodies that cross-reacted with both fimbriae. Monoclonal antibodies against CFA/I cross reacted with CS4 and inhibited the binding of both fimbriae containing strains to human jejunal enterocytes and to Caco-2 cells. These antibodies also inhibited hemagglutination and conferred passive protections against fluid accumulation in rabbit ileal loops caused by infection of both ETEC strains. (Rudin, et al., *Microb. Pathog.*, 21:35-45 (1996)). Moreover, it has been hypothesized that immunization with purified CFA/I and CS4 fimbriae may prime and boost immune response against the homologous and heterologous fimbriae. (Rudin and Svennerholm, *Microb. Pathog.*, 16:131-139 (1994); Rudin, et al., *Epidemiol. Infect.*, 119:391-393 (1997)).

Nucleotide Sequences Relating to the csa Operon

Having identified the csa operon and the genes encoded thereby, this knowledge has been used to produce useful immunogenic compositions. As is discussed more fully in the Examples below, the genes of the csa operon were cloned, sequenced and expressed. Polynucleotide molecules encoding the proteins of the csa operon and their sequences are provided below.

Representative polynucleotide molecules encoding the proteins of the csa operon (SEQ ID. NO.: 27) include sequences comprising csaA (SEQ. ID. NO.: 1), csaB (SEQ. ID. NO.: 3), csaC (SEQ. ID. NO.: 5), csaD (SEQ. ID. NO.: 7), and csaE (SEQ. ID. NO.: 9). Polynucleotide molecules encoding the proteins of the csa operon include those sequences resulting in minor genetic polymorphisms, differences between strains, and those that contain amino acid substitutions, additions, and/or deletions.

In some instances, one can employ such changes in the sequence of a recombinant csa operon-encoded protein to substantially decrease or increase the biological activity of a particular csa operon-encoded protein relative to the activity of the corresponding wild-type csa operon-encoded protein. Such changes can also be directed towards an endogenous csa operon encoded sequence using, for example, various molecular biological techniques to alter the endogenous gene and therefore its protein product.

Nucleotide sequences encoding csa operon proteins can be used to identify polynucleotide molecules encoding other proteins with biological functions similar to that of the csa operon. Complementary DNA molecules encoding csa operon-like proteins can be obtained by constructing a cDNA library from mRNA from eukaryotic cells or a DNA library from other prokaryotic organisms. DNA molecules encoding csa operon-like proteins can be isolated from such a library using the sequences disclosed herein with standard hybridization techniques or by the amplification of sequences using polymerase chain reaction (PCR) amplification.

In a similar manner, genomic DNA encoding csa operon protein homologs can be obtained using probes designed from the sequences disclosed herein. Suitable probes for use in identifying csa operon produced protein homologue sequences can be obtained from csa operon-specific sequences. Alternatively, oligonucleotides containing specific DNA sequences from a csa operon-coding region can be used to identify related csa clones. One of ordinary skill in the art will appreciate that the regulatory regions of the csa operon and homologous genes and operons can be obtained using similar methods.

csa operon homologous polynucleotide molecules can be isolated using standard hybridization techniques with probes of at least about 7 nucleotides in length and up to and including the full coding sequence. Homologous csa operon sequences can be identified using degenerate oligonucleotides capable of hybridization based on the sequences disclosed herein for use PCR amplification or by hybridization at moderate or greater stringency. The term, "capable of hybridization" as used herein means that the subject nucleic acid molecules (whether DNA or RNA) anneal to an oligonucleotide of 15 or more contiguous nucleotides of SEQ. ID. NOs: 1, 3, 5, 7, and 9.

The choice of hybridization conditions will be evident to one skilled in the art and will generally be guided by the purpose of the hybridization, the type of hybridization (DNA-DNA or DNA-RNA), and the level of desired relatedness between the sequences. Methods for hybridization are well established in the literature. One of ordinary skill in the art realizes that the stability of nucleic acid duplexes will decrease with an increased number and location of mismatched bases; thus, the stringency of hybridization can be used to maximize or minimize the stability of such duplexes. Hybridization stringency can be altered by: adjusting the temperature of hybridization; adjusting the percentage of helix-destabilizing agents, such as formamide, in the hybridization mix; and adjusting the temperature and salt concentration of the wash solutions. In general, the stringency of hybridization is adjusted during the post-hybridization washes by varying the salt concentration and/or the temperature, resulting in progressively higher stringency conditions.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. As mentioned above, however, optimal conditions will vary, depending on the particular hybridization reaction involved, and can be determined empirically. In general, conditions of high stringency are used for the hybridization of the probe of interest.

Alternatively, polynucleotides having substantially the same nucleotide sequence set forth in SEQ. ID. NOs: 1, 3, 5, 7, and 9 or functional fragments thereof, or nucleotide sequences that are substantially identical to SEQ. ID. NOs: 1, 3, 5, 7, and 9, can represent members of a csa-like operon. By "substantially the same" or "substantially identical" is meant a nucleic acid or polypeptide exhibiting at least 80%, 85%, 90%, 91%, 92%, 93%, 94%, 95%, 96%, 97%, 98%, 99%, or 100% homology to a reference nucleic acid. For nucleotide sequences, the length of comparison sequences will generally be at least 10 to 500 nucleotides in length. More specifically, the length of comparison will be at least 50 nucleotides, at least 60 nucleotides, at least 75 nucleotides, and at least 110 nucleotides in length.

One embodiment of the invention provides isolated and purified polynucleotide molecules encoding one or more csa operon proteins, wherein the polynucleotide molecules that are capable of hybridizing under moderate to stringent conditions to an oligonucleotide of 15 or more contiguous nucleotides of SEQ. ID. NOs: 1, 3, 5, 7, and 9, including complementary strands thereto.

DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Screening procedures which rely on nucleic acid hybridization make it possible to isolate any gene sequence from any organism, provided the appropriate probe is available. Oligonucleotide probes, which correspond to a part of csa operon sequences provided herein and encoding a Csa protein, can be synthesized chemically. This synthesis requires that short, oligo-peptide stretches of the amino acid sequence be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA or DNA clone by the hybridization of the target DNA to that single probe in the mixture that is its complete complement. (Wallace, et al., *Nucl. Acid Res.*, 9:879, 1981). Alternatively, a subtractive library is useful for elimination of non-specific cDNA clones.

Among the standard procedures for isolating DNA sequences of interest is the formation of plasmid- or phage-carrying genomic libraries which include total DNA from the organism of interest. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target DNA can be employed in DNA/DNA hybridization procedures which are carried out on cloned copies of the DNA which have been denatured into a single-stranded form (Jay, et al., *Nucl. Acid Res.*, 11:2325, 1983).

The nucleotide sequences of the csa operon disclosed herein have a myriad of applications. Representative uses of the nucleotide sequences of the invention include the construction of DNA and oligonucleotide probes useful in Northern, Southern, and dot-blot assays for identifying and quantifying the level of expression of csa operon encoded proteins in a cell. csa operon encoded proteins have a variety of uses, for example, as antigens with which to elicit an immune response.

In addition, considering the important role the CS4 pili plays in ETEC attachment and colonization, it is thought highly likely that compositions containing the CS4 pili or compositions with activity against the same can result from expression of the csa operon. In this case, the proteins of the csa operon can prove highly useful in the generation of immunogenic compositions that can be used to generate an immune response in a subject.

Similarly, csa operon nucleotide sequences can be employed for the construction of recombinant cell lines, recombinant organisms, expression vectors, and the like. Such recombinant constructs can be used to express recombinant csa operon proteins. In one embodiment, the recombinant constructs can be used to screen for candidate therapeutic agents capable of altering the pathology of a CS4 antigen-expressing organism. In another embodiment, the proteins of the csa operon present an attractive set of proteins with which to create immunogenic compositions. For example, the CS4 pili can be expressed, purified, and used to prepare an immunogenic subunit composition. In another embodiment, recombinant CS4 pili can be expressed in an organism, and the whole organism can be formulated into an immunogenic composition.

When the coding regions of the csa operon are used in the construction of various types of vectors, the csa sequences are often inserted into the coding region of the vector under the control of a promoter. Additionally, other elements, including regulatory elements, which are commonly found in vectors suitable for use in various molecular biology techniques, can also be included.

In one embodiment, a vector comprising a DNA molecule encoding a Csa protein is provided. Preferably, a DNA molecule including a csaA, csaB, csaC, csaD, or csaE gene, or a combination of these genes is inserted into a suitable expression vector, which is in turn used to transfect or transform a suitable host cell. Exemplary expression vectors include a promoter capable of directing the transcription of a polynucleotide molecule of interest in a host cell. Representative expression vectors include both plasmid and/or viral vector sequences. Suitable vectors include retroviral vectors, vaccinia viral vectors, CMV viral vectors, BLUESCRIPT (Stratagene, San Diego, Calif.) vectors, bacculovirus vectors, and the like. In another embodiment, promoters capable of directing the transcription of a cloned gene or cDNA can be inducible or constitutive promoters and include viral and cellular promoters.

In some embodiments, it can be preferable to use a selectable marker to identify cells that contain the cloned DNA. Selectable markers are generally introduced into the cells along with the cloned DNA molecules and include genes that confer resistance to drugs, such as ampicillin, neomycin, hygromycin, and methotrexate. Selectable markers can also complement auxotrophies in the host cell. Other selectable markers provide detectable signals, such as beta-galactosidase to identify cells containing the cloned DNA molecules.

Antisense

Antisense csa nucleotide sequences can be used to block csa expression. Suitable antisense oligonucleotides are at least 11 nucleotides in length and can include untranslated (upstream) and associated coding sequences. As will be evident to one skilled in the art, the optimal length of an antisense oligonucleotide depends on the strength of the interaction between the antisense oligonucleotide and the complementary mRNA, the temperature and ionic environment in which translation takes place, the base sequence of the antisense oligonucleotide, and the presence of secondary and tertiary structure in the mRNA and/or in the antisense oligonucleotide. Suitable target sequences for antisense oligonucleotides include promoter regions, ribosome binding sites, and sites that interfere with ribosome progression.

Antisense oligonucleotides can be prepared, for example, by the insertion of a DNA molecule containing the target DNA sequence into a suitable expression vector such that the DNA molecule is inserted downstream of a promoter in a reverse orientation as compared to the particular csa gene itself. The expression vector can then be transduced, transformed or transfected into a suitable cell resulting in the expression of antisense oligonucleotides. Alternatively, antisense oligonucleotides can be synthesized using standard manual or automated synthesis techniques. Synthesized oligonucleotides are introduced into suitable cells by a variety of means including electroporation, calcium phosphate precipitation, or microinjection. The selection of a suitable antisense oligonucleotide administration method will be evident to one skilled in the art.

With respect to synthesized oligonucleotides, the stability of antisense oligonucleotide-mRNA hybrids is advantageously increased by the addition of stabilizing agents to the oligonucleotide. Stabilizing agents include intercalating agents that are covalently attached to either or both ends of the oligonucleotide. In preferred embodiments, the oligonucleotides are made resistant to nucleases by, for example, modifications to the phosphodiester backbone by the introduction of phosphotriesters, phosphonates, phosphorothioates, phosphoroselenoates, phosphoramidates, phosphorodithioates, or morpholino rings.

Amino Acids

The identification of the csa operon and the proteins encoded thereby is described. Representative polypeptides produced from the genes of the csa operon include sequences comprising CsaA (SEQ. ID. NO.: 2), CsaB (SEQ. ID. NO.: 4), CsaC (SEQ. ID. NO.: 6), CsaD (SEQ. ID. NO.: 8), and CsaE (SEQ. ID. NO.: 10). Variants of the csa operon encoded proteins include those amino acid sequences resulting from in minor genetic polymorphisms, differences between strains, and those that contain amino acid substitutions, additions, and/or deletions.

The csa operon encoded proteins, as described herein, encompass the whole proteins encoded by the operon, as well as fragments of csa proteins that are functionally active. csa operon encoded proteins purified from naturally occurring materials and closely related, functionally similar proteins retrieved by antisera specific to the csa proteins, and recombinantly expressed proteins encoded by genetic materials (DNA, RNA, cDNA) retrieved on the basis of their similarity to regions in the csa operon sequences are also encompassed by the present description.

According to the present description, polynucleotide molecules encoding csa operon encoded proteins encompass those molecules that encode csa proteins or peptides that share identity with the sequences shown in SEQ. ID. NOs.: 2, 4, 6, 8, and 10. Such molecules preferably share greater than 30% identity at the amino acid level with the disclosed sequences in csa. In preferred embodiments, the polynucleotide molecules can share greater identity at the amino acid level across highly conserved regions.

It is contemplated that amino acid sequences substantially the same as the sequences set forth in SEQ. ID. NOs.: 2, 4, 6, 8, and 10, are encompassed by the present description. A preferred embodiment includes polypeptides having substantially the same sequence of amino acids as the amino acid sequence set forth in SEQ ID NOs.: 2, 4, 6, 8, and 10, or functional fragments thereof, or amino acid sequences that are substantially identical to SEQ ID NOs.: 2, 4, 6, 8, and 10. By "substantially the same" or "substantially identical" is meant a polypeptide exhibiting at least 80%, 85%, 90%, 90%, 91%, 92%, 93%, 94%, 95%, 96%, 97%, 98%, 99%, or 100% homology to a reference amino acid sequence. For polypeptides, the length of comparison sequences will generally be at least 16 amino acids, preferably at least 20 amino acids, more preferably at least 25 amino acids, and most preferably 35 amino acids.

Homology is often measured using sequence analysis software (e.g., Sequence Analysis Software Package of the Genetics Computer Group, University of Wisconsin Biotechnology Center, 1710 University Avenue, Madison, Wis. 53705 or the NCBI BLAST program). Such software matches similar sequences by assigning degrees of homology to various substitutions, deletions, substitutions, and other modifications.

The term "functional fragments" include those fragments of SEQ ID NOs.: 2, 4, 6, 8, and 10, or other proteins that have a similar amino acid sequence as that of the csa operon encoded proteins, that retain the function or activity of the various csa proteins. One of skill in the art can screen for the functionality of a fragment by using the examples provided herein, where full-length csa operon encoded proteins are described. It is also envisioned that fragments of various csa operon encoded proteins can be identified in a similar manner.

By "substantially identical" is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed, (e.g., as described herein). Preferably, such a sequence is at least 85%, and more preferably from 90%, 91%, 92%, 93%, 94%, 95%, 96%, 97%, 98%, 99%, to 100% homologous at the amino acid level to SEQ ID NOs:2, 4, 6, 8, or 10.

By a "substantially pure polypeptide" is meant a csa operon encoded protein that has been separated from components that naturally accompany it. Typically, the polypeptide is substantially pure when it is at least 60%, by weight, free from the proteins and other naturally occurring molecules with which it is typically associated. Preferably, the preparation is at least 75%, 80%, 90%, 95%, and most preferably at least 99%, by weight, csa operon encoded protein. A substantially pure csa operon encoded polypeptide can be obtained, for example, by extraction from a natural source; by expression of a recombinant nucleic acid encoding a csa operon encoded polypeptide; or by chemically synthesizing the protein. Purity can be measured by any appropriate method, e.g., column chromatography, polyacrylamide gel electrophoresis, or by HPLC analysis.

A protein is substantially free of naturally associated components when it is separated from those contaminants that accompany it in its natural state. Thus, a protein that is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

As would be evident to one skilled in the art, the polynucleotide molecules of the present disclosure can be expressed in a variety of prokaryotic and eucaryotic cells using regulatory sequences, vectors, and methods well established in the literature.

csa operon encoded proteins produced according to the present description can be purified using a number of established methods such as affinity chromatography using an anti-Csa protein antibodies coupled to a solid support. Fusion proteins of an antigenic tag and a csa operon encoded protein can be purified using antibodies to the tag. Optionally, additional purification is achieved using conventional purification means such as liquid chromatography, gradient centrifugation, and gel electrophoresis, among others. Methods of protein purification are known in the art and can be applied to the purification of recombinant csa operon encoded proteins described herein. Purification of csa operon products is discussed more completely below.

Construction of csa operon encoded fusion proteins is also contemplated. Fusion proteins will typically contain additions, substitutions, or replacements of one or more contiguous amino acids of the native csa operon encoded protein with amino acid(s) from a suitable fusion protein partner. Such fusion proteins are obtained using recombinant DNA techniques well known by one of skill in the art. Briefly, DNA molecules encoding the hybrid csa operon encoded proteins of interest are prepared using generally available methods such as PCR mutagenesis, site-directed mutagenesis, and/or restriction digestion and ligation. The hybrid DNA is then inserted into expression vectors and introduced into suitable host cells.

One embodiment of the present invention involves the isolation of proteins that interact with csa operon encoded proteins or are receptors for CS4 pili. csa operon encoded proteins can be used in immunoprecipitation to isolate interacting factors or used for the screening of interactors using different methods of two hybrid screening. Isolated interactors of csa operon encoded proteins can be used to modify or block CS4 mediated binding to a host cell.

Synthetic peptides, recombinantly derived peptides, fusion proteins, chiral proteins (stereochemical isomers, racemates, enantiomers, and D-isomers) and the like are provided which include a portion of a csa operon encoded protein or the entire protein. The subject peptides have an amino acid sequence encoded by a nucleic acid which hybridizes under stringent conditions with an oligonucleotide of 15 or more contiguous nucleotides of SEQ. ID. NOs: 1, 3, 5, 7, and 9. Representative amino acid sequences of the subject peptides are disclosed in SEQ. ID. NOs: 2, 4, 6, 8, and 10. The subject peptides find a variety of uses, including preparation of specific antibodies and preparation of antagonists of CS4 binding.

Antibodies

As noted above, the described teachings provide antibodies that bind to csa operon encoded proteins. The production of non-human antisera or monoclonal antibodies (e.g., murine, lagomorph, porcine, equine) is well known and can be accomplished by, for example, immunizing an animal with a csa operon encoded protein or peptides. For the production of monoclonal antibodies, antibody producing cells are obtained from immunized animals, immortalized and screened, or screened first for the production of the antibody that binds to the particular csa operon encoded protein or peptides and then immortalized. It can be desirable to transfer the antigen binding regions (e.g., F(ab')2 or hypervariable regions) of non-human antibodies into the framework of a human antibody by recombinant DNA techniques to produce a substantially human molecule.

Following synthesis or expression and isolation or purification of a csa operon encoded protein or a portion thereof, the isolated or purified protein can be used to generate antibodies and tools for identifying agents that interact with the csa operon encoded protein and fragments of interest. Depending on the context, the term "antibodies" can encompass polyclonal, monoclonal, chimeric, single chain, Fab fragments and fragments produced by a Fab expression library. Antibodies that recognize csa operon encoded proteins and fragments thereof have many uses including, but not limited to, biotechnological applications, therapeutic/prophylactic applications, and diagnostic applications.

For the production of antibodies, various hosts including goats, rabbits, rats, mice, etc., can be immunized by injection with csa operon encoded proteins or any portion, fragment or oligopeptide that retains immunogenic properties. Depending on the host species, various adjuvants can be used to increase immunological response. Such adjuvants include, but are not limited to, detoxified heat labile toxin from *E. coli*, Freund's, mineral gels such as aluminum hydroxide, and surface active substances such as lysolecithin, pluronic polyols, polyanions, peptides, oil emulsions, keyhole limpet hemocyanin, and dinitrophenol. BCG (*Bacillus Calmette-Guerin*) and *Corynebacterium parvum* are also potentially useful adjuvants.

Peptides used to induce specific antibodies can have an amino acid sequence consisting of at least three amino acids, and preferably at least 10 to 15 amino acids. Preferably, short stretches of amino acids encoding fragments of csa operon encoded proteins are fused with those of another protein such as keyhole limpet hemocyanin such that an antibody is produced against the chimeric molecule. While antibodies capable of specifically recognizing csa operon encoded proteins can be generated by injecting synthetic 3-mer, 10-mer, and 15-mer peptides that correspond to a protein sequence of the csa operon encoded protein or proteins of interest into mice, a more diverse set of antibodies can be generated by using recombinant csa operon encoded proteins, purified csa operon encoded proteins, or fragments of csa operon encoded proteins.

To generate antibodies to csa operon encoded proteins and fragments thereof, a substantially pure csa operon encoded protein or a fragment thereof is isolated from a transfected or transformed cell or the wildtype ETEC organism. The concentration of the polypeptide in the final preparation is adjusted, for example, by concentration on an Amicon filter device, to the level of a few micrograms/ml. Monoclonal or polyclonal antibody to the polypeptide of interest can then be prepared as follows:

Monoclonal antibodies to csa operon encoded proteins or a fragment thereof can be prepared using any technique that provides for the production of antibody molecules by continuous cell lines in culture. These include, but are not limited to, the hybridoma technique originally described by Koehler and Milstein (*Nature* 256:495-497 (1975), the human B-cell hybridoma technique (Kosbor et al. *Immunol Today* 4:72 (1983); Cote et al *Proc Natl. Acad. Sci* 80:2026-2030 (1983), and the EBV-hybridoma technique Cole et al. *Monoclonal Antibodies and Cancer Therapy*, Alan R. Liss Inc, New York N.Y., pp 77-96 (1985). In addition, techniques developed for the production of "chimeric antibodies", the splicing of mouse antibody genes to human antibody genes to obtain a molecule with appropriate antigen specificity and biological activity can be used. (Morrison et al. *Proc Natl Acad. Sci* 81:6851-6855 (1984); Neuberger et al. *Nature* 312:604-608 (1984); Takeda et al. *Nature* 314:452-454(1985). Alternatively, techniques described for the production of single chain antibodies (U.S. Pat. No. 4,946,778) can be adapted to produce csa operon encoded protein-specific single chain antibodies. Antibodies can also be produced by inducing in vivo production in the lymphocyte population or by screening recombinant immunoglobulin libraries or panels of highly specific binding reagents as disclosed in Orlandi et al., *Proc Natl. Acad. Sci.*, 86:3833-3837 (1989), and Winter G. and Milstein C; *Nature* 349:293-299 (1991).

Antibody fragments that contain specific binding sites for csa operon encoded proteins can also be generated. For example, such fragments include, but are not limited to, the $F(ab')_2$ fragments that can be produced by pepsin digestion of the antibody molecule and the Fab fragments that can be generated by reducing the disulfide bridges of the $F(ab')_2$ fragments. Alternatively, Fab expression libraries can be constructed to allow rapid and easy identification of monoclonal Fab fragments with the desired specificity. (Huse W. D. et al. *Science* 256:1275-1281 (1989)).

By one approach, monoclonal antibodies to csa operon encoded proteins or fragments thereof are made as follows. Briefly, a mouse is repetitively inoculated with a few micrograms of the selected protein or peptides derived therefrom, over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology Elsevier*, New York. Section 21-2.

Polyclonal antiserum containing antibodies to heterogeneous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and can require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988-991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 μM). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980). Antibody preparations prepared according to either protocol are useful in quantitative immunoassays that determine concentrations of antigen-bearing substances in biological samples; they are also used semi-quantitatively or qualitatively (e.g., in diagnostic embodiments that identify the presence of a csa operon encoded protein in biological samples). It is also contemplated that various methods of molecular modeling and rational drug design can be applied to identify compounds that resemble a csa operon encoded protein, fragment, or derivative thereof, and molecules that interact with csa operon encoded proteins and, thereby modulate their function.

Expression Vectors

Recombinant gene expression vectors comprising the csa operon, or portions thereof, can be constructed in a variety of forms well-known in the art. Preferred expression vectors include plasmids and cosmids. Expression vectors include one or more fragments of the csa operon. Typically, an expression vector will comprise one or more genes of csa operon. In one embodiment, an expression vector will comprise and operatively encode the csaA, csaB, csaC, csaE, and csaD coding regions. Alternative embodiments of the described expression vectors can have various combinations of the coding regions csa operon. For example, an expression can comprise the csaB, the csaE coding regions, or a combination of both.

As used herein, the phrase "operatively encode" refers to one or more protein coding regions associated with those regulatory sequences required for expression of the polypeptide encoded by the coding region. Examples of such regulatory regions including promoter binding sites, enhancer elements, ribosome binding sites, and the like. Those of ordinary skill in the art will be able to select regulatory sequences and incorporate them into the recombinant expression vectors described herein without undue experimentation. For example, suitable regulatory sequences for use in various eukaryotic and prokaryotic systems are described in Ausubel, et al., *Short Protocols in Molecular Biology*, 3$^{rd}$ ed., John Wiley & Sons, Inc, New York, 1997, which is hereby incorporated by reference in its entirety.

Expression vectors for use with the csa operon will typically contain regulatory sequences derived from a compatible species for expression in the desired host cell. For example, when *E. coli* is the host cell, the host cell population can be typically transformed using pBR322, a plasmid derived from an *E. coli* species. (Bolivar, et al., Gene, 2:95, 1977). pBR322 contains genes for ampicillin (AMPR) and tetracycline resistance and thus provides easy means for identifying transformed cells.

Promoters suitable for use with prokaryotic hosts illustratively include the beta-lactamase and lactose promoter systems (Chang, et al., Nature, 275:617, 1978; and Goeddel, et al., Nature, 281:544, 1979), alkaline phosphatase, the tryptophan (trp) promoter system (Goeddel, Nucleic Acids Res., 8:4057, 1980) and hybrid promoters such as the taq promoter (de Boer, et al., Proc. Natl. Acad. Sci. USA, 80:21-25, 1983). Other functional bacterial promoters are also suitable. Their nucleotide sequences are generally known in the art, thereby enabling a skilled worker to ligate them to a polynucleotide which encodes the peptide of interest (Siebenlist, et al., Cell, 20:269, 1980) using linkers or adapters to supply any required restriction sites.

In addition to prokaryotes, eukaryotic microbes such as yeast cultures can also be used as source for the regulatory sequences. *Saccharomyces cerevisiae* is a commonly used eukaryotic host microorganism. Suitable promoting sequences for use with yeast hosts include the promoters for 3-phosphoglycerate kinase (Hitzeman, et al., J. Biol. Chem., 255:12073, 1980) or other glycolytic enzymes (Hess, et al. J. Adv. Enzyme Reg. 7:149, 1968; and Holland, Biochemistry, 17:4900, 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degraded enzymes associated with nitrogen metabolism, metallothionine, glyceraldehyde-3-phosphate dehydrogenase, and enzymes responsible for maltose and galactose utilization. Yeast enhancers also are advantageously used with yeast promoters.

In another embodiment, a recombinant virus is used as the expression vector. Exemplary viruses include the adenoviruses, adeno-associated viruses, herpes viruses, vaccinia, or an RNA virus such as a retrovirus or an alphavirus. Preferably, the retroviral vector is a derivative of a murine or avian retrovirus. Preferably the alphavirus vector is derived from Sindbis or Semliki Forest Virus. All of these vectors can transfer or incorporate a gene for a selectable marker so that transduced cells can be identified and generated.

By inserting one or more sequences of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector, such as to the vicinity of a mucosal inductor site, using a MALT-specific antibody. Those of skill in the art will know of, or can readily ascertain without undue experimentation, specific polynucleotide sequences which can be inserted into the retroviral genome to allow target specific delivery of the retroviral vector containing the polynucleotides of interest.

It will be appreciated that the same techniques that are utilized to incorporate the nucleotide sequences of the csa operon and optionally other immunostimulatory polynucleotides into viral gene expression vectors can be used to incorporate the sequences into live and attenuated live viruses for use as immunogenic compositions.

Targeting of mucosal tissues can be performed by exploiting inherent biological properties of the lymphoid bed which is to be targeted. These include the crypt architecture of the tonsillar pillars which can be used to entrap particles, and also include the M cells of Peyer's patches in the gut, which M cells specifically endocytose a wide variety of particles including lipid particles and other small particulates. Therefore, those skilled in the art can prepare a wide variety of molecular particulate preparations which, if provided to intestine, will lodge within the crypt portions of intestinal Peyer's patches and be endocytosed by M cells. If such particles provide for delivery of a biologically active polynucleotide to M cells, then such particles will enable the stimulation or modulation of mucosal immune response induction by the Peyer's patch lymphoid tissue to which the M cell traffics.

Construction of suitable vectors containing desired coding, non-coding and control sequences employ standard ligation techniques. Isolated plasmids or DNA fragments are cleaved, tailored, and re-ligated in the form desired to construct the plasmids required.

For example, for analysis to confirm correct sequences in plasmids constructed, the ligation mixtures can be used to transform a host cell and successful transformants selected by antibiotic resistance where appropriate. Plasmids from the transformants are prepared, analyzed by restriction and/or sequenced by, for example, the method of Messing, et al., (Nucleic Acids Res., 9:309, 1981), the method of Maxam, et al., (Methods in Enzymology, 65:499, 1980), or other suitable methods which will be known to those skilled in the art. Size separation of cleaved fragments is performed using conventional gel electrophoresis as described, for example, by Maniatis, et al., (Molecular Cloning, pp. 133-134, 1982).

Host cells can be transformed with the expression vectors described herein and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

Purification

The purification of one or more of the products of the csa operon is disclosed below. Steps involved in the purification of csa operon products include (1) solubilization of the desired protein, (2) the development of one or more isolation and concentration procedures, (3) stabilization of the protein following purification, and (4) development of a suitable assay to determine the presence of the desired protein. Various aspects of protein isolation and purification are discussed in detail in Cooper, T. G., "The Tools of Biochemistry," John Wiley & Sons, New York, 1977, which is hereby incorporated by reference in its entirety. As the techniques of protein isolation and purification are notoriously well known in the art, this disclosure will refrain from discussing them in detail. Nevertheless, elements of the cited reference are summarized and discussed below.

Solubilization is required of most proteins to be purified, as most isolation procedures commonly used operate in aqueous solutions. In some cases solubilization can be achieved by merely lysing a host cell within which a desired protein has been expressed. In other situations, additional steps, such as extracting the desired protein from a subcellular organelle may be required. Osmotic lysis, grinding, the use of blenders, ultrasonic waves, presses, and other well known techniques of protein solubilization are contemplated for use with the methods disclosed herein.

Regarding the isolation and concentration of csa operon products, there are variety of techniques available that are well known in the art. These techniques include (1) differential solubility, (2) ion exchange chromatography, (3) absorption chromatography, (4) molecular sieve techniques, (5) affinity chromatography, (6) electrophoresis, and (7) electrofocusing. Each of these techniques can be useful in the purification of one or more csa operon products. An immunogenic purification methodology for the purification of the CS4 pili is described in Wolf, et al., "Characterization of CS4 and CS6 antigenic components of PCF8775, a putative colonization factor complex from enterotoxigenic *Escherichia coli* E8775," *Infect Immun.* 57(1):164-73 (1989), which is hereby incorporated by reference in its entirety. For purifying intact CS4 fimbriae, use the methods described in Hall, et al., *J. Bacteriol.* 171:6372 (1989).

Stabilizing and maintaining a purified product of the csa operon in a functional state warrants attention to a number of different conditions. These conditions include (1) pH, (2) degree of oxidation, (3) heavy metal concentration, (4) medium polarity, (5) protease concentration, and (6) temperature. One of ordinary skill in the art would readily know which of the available techniques to use to maintain purified csa operon products in an active form without undue experimentation.

Developing one or more assays with which to determine the presence and functionality of the purified product of the csa operon will hinge on the individual proteins themselves. Perhaps the most useful assay to develop involves the generation of one or more antibodies with which to identify the various products of the csa operon. The generation of antibodies is discussed herein. Because the nucleotide and amino acid sequences of each of the csa operon encoded gene sequences is known, it would be trivial for one of ordinary skill in the art to generate suitable antibodies for the detect of Csa proteins, using techniques that are notoriously well known.

Compositions

The proteins encoded by the csa operon can be used to formulate immunogenic compositions that facilitate an immune response. Examples of a typical immune response include a mucosal immune response and a systemic immune response. A variety of embodiments utilizing the proteins of the csa operon are envisioned.

Recombinant Organisms

In one embodiment, a nucleotide sequence comprising the csa operon or a functional fragment thereof is introduced into an exogenous organism using standard molecular biology techniques well known to those of ordinary skill in the art. Exemplary techniques are discussed in Ausubel, et al., "Short Protocols in Molecular Biology." The resulting recombinant organism can then be used as an immunogen against which an immune response may be engendered. In a preferred embodiment, an attenuated pathogenic organism serves as the exogenous organism. It is contemplated that an entire recombinant organism or a functional fragment thereof, such as an isolated membrane fraction, liposome, or the like, can be used to generate an immunogenic composition.

For example, one application of the discoveries described herein is directed to the development of a multivalent hybrid vaccine to prevent both *Shigella* dysentery and ETEC diarrhea, (Altboum, Z., et al., Attenuated *Shigella flexneri* 2a ΔguaBA strain CVD 1204 expressing ETEC CS2 and CS3 fimbriae as a live mucosal vaccine against *Shigella* and enterotoxigenic *Escherichia coli* infection, In press; Koprowski, et al., *Infect. Immun.*, 68:4884-92 (2000); Kotloff, et al., Vaccine, 13:495-502 (1995); Levine, et al., "Fimbrial vaccines," In P. Klemm (ed.), *Fimbriae: adhesion, biogenics, genetics and vaccines*, Boca Raton: CRC Press, 1994; Noriega, et al., *Infect. Immun.*, 64:23-27 (1996)). U.S. Pat. No. 6,190,669, to Noriega, et al., entitled "Attenuated mutants of *salmonella* which constitutively express the Vi antigen," which is hereby incorporated by reference in its entirety, contains additional teaching relating to the generation of such chimeric organisms suitable for use in the preparation of an immunogenic composition containing the CS4 pili.

In a preferred embodiment, the ETEC-CS4 fimbrial encoding genes of the csa operon are isolated and used to construct an efficient multivalent *Shigella*-ETEC immunogenic composition that will protect from diarrhea caused by either *Shigella* and CS4 expressing ETEC strains. One aspect of this embodiment is directed to creating an immunogenic composition capable of generating an immune response against LTh, the LT variant found in human ETEC strains. The immunogenic properties of cloned CFA/I, CS2, CS3 and LThK63 encoding genes in *S. flexneri* 2a strain CVD 1204 have been reported. This work has been expanded by including the expression of the CS4 pili as an intact fimbriae in both *E. coli* and *Shigella* strains.

Other multivalent immunogenic compositions effective against enteric bacteria are contemplated. For example, a multivalent immunogenic composition against *Salmonella* spp.; *Clostridium* spp., such as *Clostridium botulinum*; *Staphylococcus* spp, such as *S. aureus*; *Campylobacter* spp., such as *C. jejuni*; *Yersinia* spp., such as *Y. enterocolitica* and *Y. pseudotuberculosis*; *Listeria* spp., such as *L. monocytogenes*; various *Vibrio* spp., including *V. cholerae* O1, *V. cholerae* non-O1, *V. parahaemolyticus*, *V. vulnificus*; *Clostridium* spp., such as *C. perfringens*; *Bacillus* spp., such as *B. cereus*;

*Aeromonas* spp., such as *A. hydrophila; Plesiomonas* spp., such as *P. shigelloides; Shigella* spp.; *Streptococcus* spp.; various miscellaneous enterics such as *Klebsiella* spp.; *Enterobacter* spp.; *Proteus* spp.; *Citrobacter* spp.; *Aerobacter* spp.; *Providencia* spp.; *Serratia* spp.; and members of the enterovirulent *Escherichia coli* Group (EEC Group) which comprises, enterotoxigenic *Escherichia coli* (ETEC), enteropathogenic *Escherichia coli* (EPEC), enterohemorrhagic *Escherichia coli* (EHEC) such as *Escherichia coli* O157:H7, and enteroinvasive *Escherichia coli* (EIEC).

Subunit Vaccines

Another embodiment described herein relates to the generation of immunogenic compositions comprising distinct immunogenic proteins or fragments thereof, or functional fragments of organisms of interest. Such immunogenic compositions are referred to here as subunit immunogenic composition because at least one of the components of the composition is a subunit of an organism, rather than an entire organism. Typically, a subunit immunogenic composition as described herein comprises one or more immunogenic components.

In a preferred embodiment, the subunit immunogenic composition described herein comprise a carrier component and an immunogenic component. Typically, the carrier component will function as a binding moiety with which the originating organism uses to bind to and gain entrance into the host organism. One example of such a carrier component is the CS4 antigen, which is encoded by the csa operon. The CS4 antigen allows ETEC strains expressing this protein complex to bind to the mucosa of a human host. In a preferred embodiment the CsaB and/or the CsaE proteins can function as carrier components.

Although not wishing to be bound by theory, it is hypothesized that the subunit immunogenic composition described herein function by exposing the immunogenic component of the subunit immunogenic composition to the mucosa, and various immune system components present there. In one theory, the generation of a desired immune response by the subunit immunogenic compositions described herein occurs by increasing the exposure of the immunogenic compositions to the target tissue. The presence of both a carrier component and an immunogenic component are theorized to achieve this goal.

Any protein, peptide, or amino acid sequence that elicits an immune response can be used as the immunogenic component in the subunit immunogenic compositions described herein.

The carrier components of the described subunit immunogenic compositions can also possess immunogenic characteristics themselves. Typically, adjuvants are used in immunogenic compositions to enhance the immune response directed against the immunogenic component of the immunogenic compositions disclosed. Carrier components that possess both mucosa binding characteristics and immunogenic characteristics can be used. For example, in one embodiment, the CsaB and/or the CsaE proteins can function both as the carrier component and the immunogenic component.

For the carrier components described above, the entire molecule can be used as the carrier component, or a functionally active fragment of the molecule can be used. Mutagenized forms of these molecules can also be used as carrier components.

In one embodiment, one or more Csa proteins are isolated and purified. The one or more Csa proteins can be mixed or coupled with one or more immunogenic compounds. For example, in one embodiment, CsaB can be expressed, purified, and cross-linked to a toxin, toxoid (an attenuated toxin), or some other immunogenic compound for use in a subunit immunogenic compositions.

In another embodiment, expressed Csa proteins or fragments thereof, or whole CS4 antigen complexes can be cross-linked to an immunogenic component. The immunogenic component can also be an isolated protein, functional fragment thereof, whole organism (such as a bacterium or a virus), or functional fragment thereof, that is isolated either in part or as is used as a whole pathogenic organism. The Csa proteins can be isolated from the bacterium itself or it can be produced using recombinant DNA techniques well known in the art.

In accordance with one aspect of the present invention, the smaller fragments of expression product of the csa operon are used to provide an immunogenic composition. Specifically, these fragments will comprise an immunogenic region of such expression product, typically from about 5, 6, 8, 10 or 12 amino acids to about 20, 22, 24, 30, or more amino acids. Suitable fragments or immunogenic regions can be readily ascertained using as screening procedures the techniques set forth in Examples 1-4. In one embodiment of a suitable screening procedure, a large number of candidate fragments are more or less randomly produced and used to immunize guinea pigs or other suitable models. Alternatively, full-length polypeptides shown to be active in the present invention can be truncated and screened in an iterative process to isolate the immunogenic and protective activity to a minimal fragment. Such screening can be readily carried out without undue experimentation and the active fragments are within the contemplation of the present invention.

The Csa proteins used to form the immunogenic compositions of this embodiment can be the whole protein, such as the CsaB or CsaE proteins, an immunogenic fragment of a Csa protein, a mutagenized form of a Csa protein, or a fusion protein comprising a Csa protein or a fragment thereof and a suitable fusion partner. A suitable fusion partner for such a Csa fusion protein or a fragment thereof might be any protein, peptide or amino acid sequence that facilitates the expression and/or purification of the Csa fusion protein using recombinant DNA techniques known in the art. Alternatively, one or more additional immunogens can serve as the fusion partner in a Csa fusion protein.

Nucleotide Immunogenic Compositions

In another embodiment, an immune response can be elicited using nucleotide-containing compositions. In one aspect of this embodiment, a mucosal or systemic immune response is elicited in a host by administering an antigen-encoding polynucleotide preparation, comprising DNA or RNA, which encodes an antigenic epitope to the host. In a preferred embodiment, the nucleotide-containing composition is administered to a mucosal inductor site in the mucosal tissue of the host.

Naked DNA may be administered directly to mucosa, for instance in saline drops, or in a recombinant gene expression vector. Preferably, the recombinant gene expression vectors are not capable of replication or dissemination. Nucleotide-containing immunogenic compositions also comprise live viral immunogenic compositions wherein the viruses include immunostimulatory polynucleotides. According to a preferred method of the invention, a target protein antigen is administered through its expression by a recombinant gene expression vector.

U.S. Pat. No. 6,110,898, to Malone, et al., entitled, "DNA vaccines for eliciting a mucosal immune response," which is hereby incorporated by reference in its entirety, provides detailed teaching for the generation of such immunogenic compositions.

Formulations and Administration

The immunogenic compositions described herein can be formulated in a variety of useful formats for administration by a variety of routes. Concentrations of the immunogenic components in the formulations described will be such that an effective dose of the immunogenic components are included in the formulation. Determination of such a concentration would be readily apparent to those of ordinary skill in the art.

Administration of the immunogenic compositions can be by nasal application, by inhalation, ophthalmically, orally, rectally, vaginally, or by any other mode that results in the immunogenic contacting the mucosal tissues.

In one embodiment, the immunogenic composition exists as an atomized dispersion for use in delivery by inhalation. The atomized dispersion of the immunogenic components will typically contain carriers for atomized or aerosolized dispersions, such as buffered saline and other compounds well known to those of skill in the art. The delivery of the described immunogenic compositions via inhalation has the effect of rapid dispersion to a large area of mucosal tissues, as well as absorption by the blood for circulation of the immunogenic components. One example of a method of preparing an atomized dispersion is found in U.S. Pat. No. 6,187,344, entitled, "Powdered Pharmaceutical Formulations Having Improved Dispersibility," which is hereby incorporated by reference in its entirety.

The immunogenic compositions described herein can also be formulated in the form of a suppository, whether rectal or vaginal. Typical carriers for formulation of the inactive portion of a suppository include polyethylene glycol, glycerine, cocoa butter and other compounds well known to those of skill in the art. Other suppository formulations suitable for delivery of the described immunogenic compositions are also contemplated. Delivery of the described immunogenic compositions via suppository it hypothesized to have the effect of contacting a mucosal surface with the immunogenic compositions for release to proximal mucosal tissues. Distal mucosal tissues also receive the immunogenic compositions by diffusion.

Additionally, immunogenic compositions are contemplated as existing in a liquid form. The liquid can be for oral dosage, for ophthalmic or nasal dosage as drops, or for use as an enema or douche. When the immunogenic compositions is formulated as a liquid, the liquid can be either a solution or a suspension of the immunogenic compositions.

A colloidal dispersion system may be used for targeted delivery of nucleic acid-containing immunogenic compositions. Colloidal dispersion systems include macromolecule complexes, nanocapsules, microspheres, beads, and lipid-based systems including oil-in-water emulsions, micelles, mixed micelles, and liposomes. A preferred colloidal system is a lipid preparation including unilamaller and multilamellar liposomes.

Liposomes are artificial membrane vesicles that are useful as delivery vehicles in vitro and in vivo. It has been shown that large unilamellar vesicles (LUV), which range in size from 0.2-4.0 µm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988). In addition to such LUV structures, multilamellar and small unilamellar lipid preparations that incorporate various cationic lipid amphiphiles can also be mixed with anionic polynucleotides to form nucleolipidic particles which are often also referred to as liposomes (Felgner, et al, Proc Natl. Acad. Sci. U.S.A. 84 (21): 7413 1987) and used to deliver the nucleic acids into cells.

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. The appropriate composition and preparation of cationic lipid amphiphile:polynucleotide formulations are known to those skilled in the art, and a number of references which provide this information are available (e.g., Bennett, et al, J. Liposome Res. 6(3):545).

Examples of lipids useful in liposome production include phosphatidyl compounds, such as phosphatidyiglycerol, phosphatidyicholine, phosphatidylserine, phosphatidylethanolamine, sphingolipids, cerebrosides, and gangliosides. Particularly useful are diacylphosphatidyiglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. Examples of cationic amphiphilic lipids useful in formulation of nucleolipid particles for polynucleotide delivery include the monovalent lipids DOTAP, DOTMA, and DC-Chol, the polyvalent lipids LipofectAMINE, DOGS, TRANS-FECTAMTN™ and other amphiphilic polyamines. These agents may be prepared with helper lipids (such as Dioleoyl Phosphatidyl Ethanolamine) or with various carrier compositions, including various adjuvants, such as cholera-derived molecules including cholera toxin.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs that contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

There are a variety of suitable formulations for the solution or suspension well known to those of skill in the art, depending on the intended use thereof.

Delivery of the described immunogenic compositions in liquid form via oral dosage has the aim of exposing the mucosa of the gastrointestinal and urogenital tracts to the immunogenic compositions. A suitable dose, stabilized to resist the pH extremes of the stomach, would deliver the immunogenic compositions to all parts of the gastrointestinal tract, especially the upper portions thereof. All means of stabilizing the immunogenic compositions in a liquid oral dosage such that the effective delivery of the composition is distributed along the gastrointestinal tract are contemplated for use with the immunogenic compositions described herein.

Delivery of the described immunogenic compositions in liquid form via ophthalmic drops has the aim of exposing the mucosa of the eyes and associated tissues to the immunogenic compositions. A typical liquid carrier for eye drops is buffered and contains other compounds well known to those of skill in the art.

Delivery of the described immunogenic compositions in liquid form via nasal drops has the aim of exposing the mucosa of the nose and sinuses and associated tissues to the immunogenic compositions. Liquid carriers for nasal drops are typically various forms of buffered saline.

Administration of the compounds discussed above can be practiced in vitro or in vivo. When practiced in vitro, any sterile, non-toxic route of administration may be used. When practiced in vivo, administration of the compounds discussed above may be achieved advantageously by subcutaneous, intravenous, intramuscular, intraocular, oral, transmucosal, or transdermal routes, for example by injection or by means of a controlled release mechanism. Examples of controlled release mechanisms include polymers, gels, microspheres, liposomes, tablets, capsules, suppositories, pumps, syringes, ocular inserts, transdermal formulations, lotions, creams, transnasal sprays, hydrophilic gums, microcapsules, inhalants, and colloidal drug delivery systems.

The compositions described herein are administered in a pharmaceutically acceptable form and in substantially non-toxic quantities. A variety of forms of the compounds administered are contemplated. The compounds may be administered in water with or without a surfactant such as hydroxypropyl cellulose. Dispersions are also contemplated, such as those utilizing glycerol, liquid polyethylene glycols, and oils. Antimicrobial compounds may also be added to the preparations. Injectable preparations may include sterile aqueous solutions or dispersions and powders, which may be diluted or suspended in a sterile environment prior to use. Carriers such as solvents or dispersion media contain water, ethanol polyols, vegetable oils and the like may also be added to the compounds described herein. Coatings such as lecithins and surfactants may be used to maintain the proper fluidity of the composition. Isotonic agents such as sugars or sodium chloride may be added, as well as products intended to delay absorption of the active compounds such as aluminum monostearate and gelatin. Sterile injectable solutions are prepared according to methods well known to those of skill in the art and can be filtered prior to storage and/or use. Sterile powders may be vacuum or freeze dried from a solution or suspension. Sustained-release preparations and formulations are also contemplated. Any material used in the composition described herein should be pharmaceutically acceptable and substantially non-toxic in the amounts employed.

Although in some of the experiments that follow the compounds are used at a single concentration, it should be understood that in the clinical setting, the compounds may be administered in multiple doses over prolonged periods of time. Typically, the compounds may be administered for periods up to about one week, and even for extended periods longer than one month or one year. In some instances, administration of the compounds may be discontinued and then resumed at a later time.

All compound preparations may be provided in dosage unit forms for uniform dosage and ease of administration. Each dosage unit form contains a predetermined quantity of active ingredient calculated to produce a desired effect in association with an amount of pharmaceutically acceptable carrier. Such a dosage would therefore define an effective amount of a particular compound.

The immunogenic compositions described herein can be administered in amounts appropriate to those individual compounds to produce an immune response. Appropriate doses for each can readily be determined by techniques well known to those of ordinary skill in the art. Such a determination will be based, in part, on the tolerability and efficacy of a particular dose using techniques similar to those used to determine proper chemotherapeutic doses.

Additionally, a kit comprising the necessary components of a immunogenic composition that elicit an immune response to a selected immunogenic component are also contemplated.

EXAMPLE 1

Isolation and Characterization of the csa Operon

The csa operon that encodes the synthesis of ETEC-CS4 pili was isolated from strain E11881A, cloned and sequenced. The csa operon consist of 5 contiguous genes encoding CsaA-CsaE proteins, which share homology to other pili assembly proteins, and especially to CFA/I. The csa operon was expressed in an attenuated *Shigella* strain, CVD1204 guaBA, constructing the *Shigella* expressing CS4 fimbriae vaccine strain CVD1204 (pGA2-CS4). Immunization of guinea-pigs with CVD1204 (pGA2-CS4) elicited the production of anti-CS4 antibodies that reacted with CS4 producing strains and prevented biological activities mediated by ETEC strains. This work contributes to previously reported results regarding the on expression of CFA/I, CS2, CS3 and LT in attenuated *Shigella*, emphasizing the feasibility of constructing an efficient multivalent *Shigella*—based oral ETEC vaccine.

The genes that encode the synthesis of ETEC CS4 fimbriae, csaA, B, C, D, E, D', (the csa operon), were isolated from strain E11881A. The csa operon encodes a 17 kDa major fimbrial subunit (CsaB), a 40 kDa tip associated protein (CsaE), a 27 kDa chaperon like protein (CsaA), a 97 kDa usher protein (CsaC), and for a deleted regulatory protein (CsaD') containing 100 amino acids out of 265. The csa operon is flanked by IS1E that inserted into the csaD' gene, and IS21 sequences upstream to the csaA. The csa operon is located on the large virulence plasmid that carries the LT genes.

A BLAST search of the predicted amino acid sequences indicated high homology of the CS4 proteins to structural and assembly proteins of CFA/I in particular, and to CS 1 and CS2 fimbriae proteins. The csaA, B, C, E operon was cloned on a 15 copy number stabilized plasmid down stream from an osmotically regulated ompC promoter. Plasmid pGA2-CS4 directs in both DH5α and *Shigella flexneri* 2a strains the production of CS4 fimbriae, as detected by western blot analysis and bacterial agglutination using anti-CS4 fimbriae immune sera. Electron microscopic examination of *Shigella* expressing the CS4 fimbriae indicated the production of lots of rod like shape extensions. Immunization of guinea pigs with *S. flexneri* 2a CVD1204 (pGA2-CS4) elicited the production of anti-CS4 antibodies that bind to CS4 fimbrial proteins, agglutinates CS4 producing strains, inhibits hemagglutination by ETEC strains and prevented the adhesion of ETEC strains to human mucosal cell line Caco-2.

Isolation of the csa Operon

Genomic DNA of strain E11881A was isolated using GNOME DNA KIT (BIO 101, Carlsbad, Calif.) protocol. The DNA was partially digested with Sau3AI, the DNA fragments with size of 5->20 kilobase pairs were isolated from agarose gels and ligated into vector pKS that was digested with BamHI and treated with shrimp alkaline phosphatase. The ligation mix was transformed into DH5α. DH5α transformants were grown in LB in the presence of carbenicillin at 50 µg/ml or kanamycin at 50 µg/ml.

The resulting transformants were harvested into 96 well microtiter plates, and assayed for the csa operon by PCR tests, based on the published sequence of the csfA gene, (the structural gene of the CS4 fimbriae, NCBI Accession number X97493). Based on that sequence, two primers were constructed which amplified 319 base pair fragment. The primers are: CS44 bp 1 to 29: GTTGACCCTACAATTGATATTTTG-CAAGC (SEQ ID NO:11) CS45 bp 378 to 348: CGAC-CCCACTATAATTCCCGCCGTTGGTGC (SEQ ID NO:12). Pools of 1200 colonies were analyzed and 2 colonies were positive in the PCR test. Both colonies were found to contain the same plasmid, pKS-CSA-I, (FIG. 1A). Sequencing of the cloned DNA fragment, indicated that plasmid pKS-CSA-I contains most of the csa operon, missing 430 bp from the 5' end of the csaA gene. DNA sequencing of the csa operon revealed a high degree of homology to the DNA sequences of the CFA/I operon (Table 2).

Figure 1B:
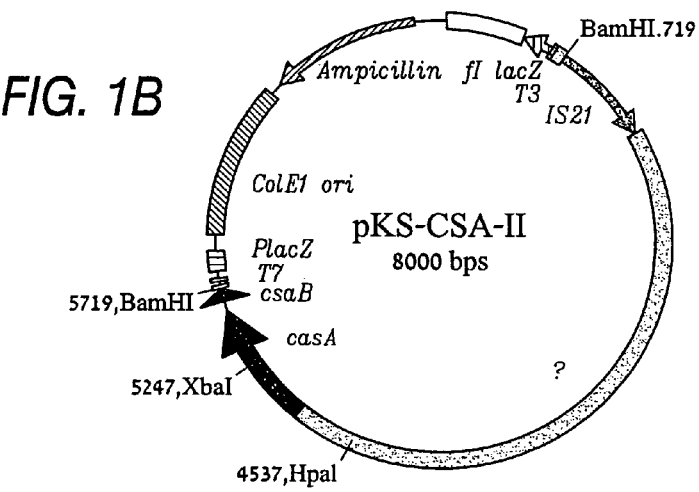

Based on that homology, two new primers were designed for screening the genomic library for the 5' end by PCR. Primer CS433 is based on the csaA sequences at bp 718, and primer CS434 is based on the CFA/I sequences from bp 878. CS433: GTGATATGTTTTGTTCACTTGGTAAAGATC (SEQ ID NO:13) CS434: CTCATGGCTCCATTTGTTG-CAAATGCAAACTTTATG (SEQ ID NO:14). PCR assays using these primers amplified a 429 bp DNA fragment from the genomic DNA of strain E118811A. By screening the DNA library, a positive clone that contained the entire csaA gene together with upstream DNA sequences was isolated. The clone contains the 8000 base pair plasmid pKS-CSA-II, (FIG. 1B).

DNA Sequence Analysis

Figure 1C:
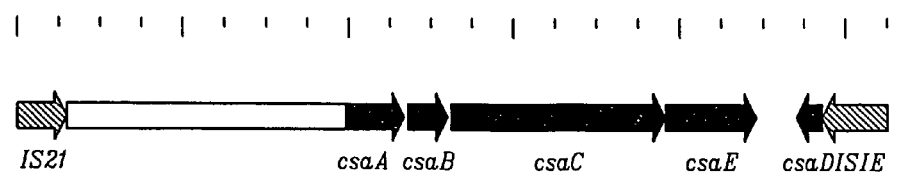
Figure 1D:

DNA sequences of the CS4 encoding genes in plasmids pKS-CSA-I and pKS-CSA-II were determined in both strands. The sequencing primers were synthesized on PERKIN ELMER™ DNA Synthesizer model 3948 at the 40 nM synthesis scale. The sequencing was performed using a PERKIN ELMER™ DNA Synthesizer 373, with the Dye Terminators from the BIGDYE KIT, PERKIN ELMER™ (Boston, Mass.). The sequencing results identified the csa operon and its flanking genes, as is schematically described in FIG. 1C.

The vector used for expression of the CS4 encoding genes in *Shigella*, pGA2, was derived from plasmid pEXO1 by replacing the gfp encoding gene (751 bp DNA, flanked by the restriction enzymes ClaI and NheI), with an 87 bp linker that contains multiple cloning sites (mcs), that was constructed by PCR, as indicated. pEXO1 is an expression plasmid derived from pGEN222. (Galen, et al., *Infect. Immun.,* 67:6424-6433 (1999)). Plasmid pGEN222 carries a two-component plasmid maintenance system comprised of the hok-sok post-segregational killing system plus the parA plasmid partitioning system. these two components have been shown to work in concert to minimize plasmid loss from a population of actively growing bacteria and to lyse any bacteria from which plasmids have segregated. pEXO1 was created from pGEN222 by replacing the bla gene, encoding β-lactamase, with an engineered aph allele encoding reduced levels of resistance to kanamycin (Blomfield, et al., *Mol. Microbiol.,* 5:1447-1457 (1991)). It was observed that expression of the wildtype aph allele within attenuated *S. typhi* vaccine strains lead to plasmid instability. Therefore, transcription of this aph allele was modified by PCR such that the separation of the −35 and −10 regions within the promoter was increased from 18 to 19 base pairs; this re-engineered allele was then introduced as an Nhe I fragment into pGEN222 cleaved with Xba I and Spe I to replace the bla gene.

The PCR fragment encoding for mcs was used as a Cla I-Nhe I restriction fragment to replace the Cla I-Nhe I restriction fragment within pEXO1 encoding the gfpuv allele, creating pGA2. pGA2 is therefore expected to be present at approximately 15 copies per chromosomal equivalent, and to drive expression of CS4 encoding genes from the osmotically responsive ompC promoter.

The mcs was constructed by PCR using the following primers:

```
Primer 4a:
                                          (SEQ ID NO:15)
GGGATCGATCCCGGGGCGGCCGCGGGCCCGGTACCAGGCCTTCTAGAAAG

CTTGACGTCG;

primer 4b:
                                          (SEQ ID NO:16)
CCCGCTAGCGGCGCGCCTCGCGAGGATCCGTCGACGACGTCAAGCTTTCT

AGAAGGCCTGG;

Primer 4c:
                                          (SEQ ID NO:17)
AAGCTTGACGTCGTCGACGG;

Primer 4d:
                                          (SEQ ID NO:18)
CCCGCTAGCGGCGCGCCTCGCG.
```

Construction of the CS4 Encoding Plasmid

Plasmid pGA2-CS4 (FIG. 2B), was constructed in three steps. The 5' end of the csaA gene was cloned from plasmid pKS-CSA-II on a 710 bp HpaI/XbaI fragment, into pKS SmaI/XbaI. The HpaI site is located 241 bp upstream the ATG codon for the csaA gene. The DNA fragment was then further cloned as a KpnI/XbaI fragment into pGA2 KpnI/XbaI, to construct pGA2-ΔcsaA plasmid. The remaining CS4 encoding genes, (the 3' end of csaA, csaB, csaC, and csaE) were cloned from pKS-CSA-I as a 4526 bp XbaI fragment. The two XbaI sites are located in the csaA gene, and in the stop codon of the csaE gene. The DNA fragment was ligated to pGA2-ΔcsaA XbaI site, to construct plasmid pGA2-CS4.

Additional DNA Primers for PCR Assays

For location of different genes by PCR assays, the following primers were constructed. For LT gene (AB011677, GI 3062900): LTA bp 162:CCGTGCTGACTCTACACCCCCAGATG (SEQ ID NO:19) and LTB bp 895:GCACATAGAGAGGATAGTAACGCCG (SEQ ID NO:20). For gyrA gene (X57174, GI 41641): GYRA bp 347:CGGTCATTGTTGGCCGTGCGCTGCC (SEQ ID NO:21) and GYRA bp 1147:CACGCAGCGCGCTGATGCCTTCCACGCG (SEQ ID NO:22). For csaD gene: CS4D3: from csa operon bp 5540-5564, and cfaD (GI 145505) bp 1236-1260.

CATATTTGATATCTGAGATATCTGG (SEQ ID NO:23) CS4D2: From csa operon bp 6005-60030, and cfaD bp 771-794, TGTTGCATTCAGATTGAACGGAG (SEQ ID NO:24). CS4D1: From cfaD bp 606-629, at similar region to rns. This DNA region is missing in csa operon: TATTATGAT-TCATAAATACACTGT (SEQ ID NO:25). PCR assays using primers CS4D2/CS4D3 is expected to amplify a 476 bp DNA, and with primers CS4D1/CS4D3, a 646 bp DNA.

Transformation of *Shigella* Strains

Shigella strains were grown in trypticase soy agar (TSA) agar plates containing 0.1% Congo red and 10 µg/ml guanine. Competent cells of *S. flexneri* 2a CVD1204 were prepared by growing the cells in L broth supplemented with guanine to $OD_{600\,nm}$ of 0.6. The cells were precipitated, washed twice with cold $H_2O$, once with cold 10% glycerol and resuspended in the same buffer at 1/100 of the original volume. A mixture of 150 µl cells and plasmid DNA were electroporated in a 0.2 cm curettes in a GENE PULSER™ (BioRad Laboratories, Hercules, Calif.) using 2.5 kV, 200Ω, 25 µF, or 1.75 kV, 600Ω, 25 µF. Transformants were selected on kanamycin, guanine and Congo red containing TSA plates.

Detection of Pili Synthesis

ETEC strains were grown on CFA (Hamers, et al., *Microb. Pathog.*, 6:297-309 (1989)) plates at 37° C., and the bacteria was resuspended in phosphate buffered saline (PBS). *Shigella* strains that contain the plasmid pGA2-CS4 were grown in TS broth, [Trypton (Difco), 1.5%; Soyton (Difco), 0.5%)], containing 0, 50, 150 and 300 mM NaCl to a logarithmic phase growth. The bacteria were assayed for pili production by bacterial agglutination assays, and by immunoblotting of cell extracts. For immunoblotting the bacterial cultures were adjusted to $OD_{600\,nm}$=10 and boiled for 10 minutes in Laemnli sample buffer (BioRad). The cell extracts proteins were separated on SDS-PAGE (15%), transferred to nitrocellulose filters (MSI) and probed with anti-CS4 serum. The specific anti-CS4 antiserum was produced in rabbits by immunization with ETEC strain E11881A (a $CS4^+$ $CS6^+$ producer strain), and absorption of the sera on EII88IC (a $CS4^-CS6^+$ strain).

Hemagglutination

For hemagglutination tests (Willshaw, et al., *FEMS Microbiol. Lett.*, 49:473-478 (1988)), ETEC and *Shigella* strains were grown overnight on CFA or TSA/CR/guanine/kanamycin containing plates, respectively, and were resuspended in PBS to $OD_{600\,nm}$ of 10. The slide hemagglutination tests, were performed as described by Sakellaris, et al 1999 (Sakellaris, et al., *Proc. Natl. Acad. Sci. U.S.A.*, 96:12828-12832 (1999)), by mixing 20 µl bacterial suspension with 20 µl PBS containing 0.1M D-mannose and 20 µl washed human erythrocytes of group A. For hemagglutination inhibition assays, the bacterial suspensions were incubated with four-fold diluted antibodies for 1 hour at 37° C. prior to the hemagglutination tests.

Adhesion and Inhibition of Adhesion to Caco-2 Cells

Caco-2 cells were grown for 15 days in 8 chamber slides in Dulbecco's modified Eagels medium containing fetal calf serum (20%) and glutamine (1%). Adhesion assays were performed by incubating washed cells with bacterial concentrations of $10^7$ and $10^8$/ml, for 2 and 3 hours in DMEM containing 0.1M D-mannose, (Viboud, et al., *Microb. Pathog.*, 21:139-147 (1996)). In the inhibition of adhesion assays, the bacterial cultures were incubated with antibodies for 1 hour, at 37° C. prior to their addition to the washed Caco-2 cells. Following the incubation, the Caco-2 cells were washed 5 times with PBS, fixed with methanol and stained with Giemsa (10%).

Immunization

Guinea pigs, anesthetized subcutaneously with ketamine HCL (40 mg/kg) and xylazine (5 mg/kg), were inoculated intranasal administration twice on days 0 and 14, with ~2×10⁹ bacteria (0.1 ml of $40OD_{600}$ nm) that grew on TSA/Congo red/guanine containing plates and harvested in PBS. Two groups of animals were immunized: group I with CVD1204 (pGA2), and group II with CVD1204 (pGA2-CS4), a CS4 producing strain. Sera were obtained on days 0, 14 and 30 by anterior vena cava puncture of anesthetized animals.

Results

Cloning and Sequencing of the CS4 Fimbriae Encoding Genes

The csa operon that encode the synthesis of the CS4 fimbriae, was isolated from a genomic DNA library of strain E11881A, as described above. Most of the csa operon was cloned on plasmid pKS—CSA-I that contains the carboxy terminal part of the csaA gene, the csaB, csaC, csaE genes and a disrupted csaD' gene. The csaD' was disrupted by integration of an IS1 element, creating a deletion of the amino terminal 48 amino acids, and a frame shift mutation that resulted in stop codon. Agglutinations assays of DH5α (pKS-CSA-I) strains with rabbit serum anti E11881A (that was absorbed on strain E11881C) were positive, which indicated expression of the CS4 fimbriae. Western blot tests indicated the presence of two fimbrial bands, the mature 17 kDa protein, and a higher MW protein, probably the pre cleaved form. By further screening of the CS4 library plasmid pKS-CSA-II was isolated. The plasmid contains the csa promoter site, the csaA gene and the amino terminal region of csaB. Up stream of the csaA gene is an IS 21 element. The csa operon is located on a ~10,500 bp DNA fragment that is flanked by insertion elements, similar to a pathogenicity island, as schematically described in FIG. 1C.

7,239 bp of the CS4 pathogenicity island was sequenced in both directions, indicating a 34.88% G+C region. The csa operon is located between bp 1 and 6,095 bp. It contains 5 ORF, 4 genes, csaA, csaB, csaC, and csaE are transcribed in the same direction down stream from a predicted promoter site, and csaD' from the antiparallel strand. The location of each gene is described in Table 1, and schematically presented in FIG. 1C. A BLAST search for homology of the csa DNA sequence (bases 1 to 6096) to other genes indicated homology to CFA/I, CS1 and CS2 ETEC fimbriae encoding genes, to the structural genes of CS4 and CS14, and to fimbriae regulatory genes cfaD, rns, csvR and aggR, as presented in Table 2. The results of the BLAST search indicate that the csa operon has a high DNA similarity to cfaI operon; 5,420 bp out of 6,069 bp are >91% similar. Comparing the DNA sequence of each gene to other fimbriae encoding genes indicate the following results:

csaA: 93% of the 717 bp of the csaA DNA sequences are identical to 716 bp of cfaA (M55661.1), and 44 bp from its 5' end are 90% identical to csoA and cooB 713 bp genes (X62879.1 and X62495.1).

csaB: 402 bp of csfA (X97493.1), the published DNA sequence of the CS4 structural gene, are 99% identical to 501 bp of the csaB DNA sequences. Of the 512 bp of cfaB, (M55661.1), the sequence of 107 bp is 93% identical to csaB. 93 bases from the 5' end of csuA1504 bp, (X9749.1), the structural gene for CS14 fimbriae, are 89% identical to csaB. 35 bp from the 5' end of cotA 512 bp gene (Z47800.1) is 94% identical to csaB.

csaC: 2601 bp of csaC gene share 96% DNA sequences similarity to 2507 bp of cfaC (M55661.1), 80% homology to 391 bp out of 2618 bp of cooC (X76908.1), and 85% homology to 124 bp out of 2597 bp of cotC (Z47800.1) genes.

csaE: 1086 bp of the csaE DNA sequences are ≧84% identical to 999 bp out of 1082 bp of cfaE (M55661.1), and 32 bp out of 1091 bp of cooD (X76908.1) are 90% identical to csaE.

csaD': csaD' DNA sequence is similar to cfaD' (CFA/I), cfaD, rns and csvR from ETEC strains, and aggR from EHEC fimbriae. DNA sequence similarity between csaD', cfaD and rns is of 751/817 bp (91%) for cfaD, and 721/787 (91%) for rns.

Comparing the regions of similarity in both genes indicated that csaD' gene is missing 143 bp from its 5'-end because of an insertion of an IS element. Blast search for DNA sequences downstream the csa operon indicated that from base 6096 to 6870 there is homology to IS1E sequences, (NCBI X52537, identities=765/769, 99%), from bp 6892 to 7054, there is homology to EPEC strain plasmid pB171 (GI 6009376), between bp 16240 and 16471. And from bp 7062-7239 there is homology to *Shigella sonnei* strain P9 plasmid collIb (GI 4512437) between bp 4895 and 5568.

Promoter Site

The promoter site for the csa operon was predicted using the "Promoter Prediction By Neural Network", and it is proposed to be located between bp 145 to 194, 89 bp upstream the ATG codon for csaA gene. The predicted promoter sequences is as follow: TGTGGGTATTTGTTTGGACATCG CAGCATTAAATATAAAAATAGCACAGG (SEQ ID NO:26). The large underline "A" is the predicted transcription start, and the shaded nucleotides are the possible −10 and −35 sequences. A BLAST search indicated a 28/31 bp (90%) homology to the CFA/I fimbrial operon, at between bp 687 to 717, 131 bp upstream to the cfaA gene.

CS4 pili structural and assemble proteins. The csa operon encodes the synthesis of five proteins: CsaA, CsaB, CsaC, CsaE and CsaD. The location of the genes and the size of the putative proteins are described in Table 1. According to sequence similarity of the CsaA-E proteins to other ETEC fimbriae proteins, the predicted functions of the CsaA-E proteins is as follow:

CsaA function as a periplasmic chaperon like protein. PSORT analysis indicate that the putative protein is a bacterial periplasmic space protein (certainty of 0.939). CsaB is the major pilin subunit. CsaC is a membrane usher protein. A PSORT analysis predicted an outer membrane location (certainty of 0.926). CsaE is assumed to be at the fimbriae tip. A PHDsec analysis (for the prediction of secondary structure) indicated that the protein is a compact protein as a globular domain. CsaD' is a fimbriae regulatory protein. The CsaD' protein contains 100 amino acids from the carboxy terminal part of the protein, missing the first 48 amino acids (based on homology to cfaD gene from CFA/I pili), because of an insertion of an IS1E element. Following the 100 amino acid is a frame shift mutation that encodes for a stop codon.

Homology of the CsaA-E Proteins to Other Fimbriae Proteins

A BLAST search with the putative amino acid sequence of CsaA-E proteins indicated homology to fimbriae proteins from ETEC strains and *Salmonella typhi* as described in Table 3. The amino acid sequence of the structural and assemble proteins of the CS4 fimbria have similarity to ETEC proteins producing the CFA/I, CS1 and CS2 fimbriae, and to the *Salmonella* fimbria. In addition, the CS4 structural proteins have amino acid sequences similar to the structural proteins of CS14, CS17, CS19 and *B. cepacia*. The CS4 fimbriae structural protein CsaB and the tip-associated protein CsaE are responsible for the fimbrial structure and for the bacterial attachment to intestine cells. An alignment of the amino acids sequences of the fimbrial proteins that are similar to CsaB and CsaE is described in FIGS. 3 and 4.

TABLE 3

Similarity in AA sequences between ETEC CsaA-E proteins and other fimbrial proteins

| CS4 protein | Pili | Protein | #amino acids | Identities | region in CS4 proteins | region in compared protein | Gene no. |
|---|---|---|---|---|---|---|---|
| CsaA | CFA/I | CfaA | 238 | 208/238 (87%) | 1-238 | 1-238 | gi 145508 |
|  | CS1 | CooB | 238 | 124/221 (56%) | 1-219 | 1-219 | gi 95719 |
|  | CS2 | CotB | 238 | 111/238 (46%) | 2-238 | 2-238 | gi 897726 |
|  |  | TsaA[1] | 236 | 60/194 (30%) | 17-207 | 22-204 | gi 5640159 |
|  | CS5 | 25.9 KD | 224 | 52/218 (23%) |  |  | P33792 |
| CsaB | CS4 | CsfA | 134 | 109/134 (81%) | 34-160 | 1-134 | gi 1304302 |
|  | CFA/I | CfaB | 170 | 99/170 (58%) | 1-167 | 1-170 | GI 145509 |
|  | CS14 | CsuA1 | 168 | 95/164 (57%) | 1-164 | 1-164 | gi 1304304 |
|  | CS1 | CooA | 171 | 85/168 (50%) | 1-164 | 1-168 | gi 78442 |
|  | CS2 | CotA | 170 | 76/167 (45%) | 1-164 | 1-167 | gi 897727 |
|  | CS14 | CsuA2 | 142 | 67/132 (50%) | 34-164 | 1-132 | gi 1304306 |
|  | CS19 | CsdA | 133 | 56/131 (42%) | 34-164 | 1-130 | gi 1304300 |
|  | CS17 | CsbA | 135 | 54/132 (40%) | 34-164 | 1-132 | gi 1304298 |
|  |  | TsaB[1] | 191 | 58/169 (34%) | 1-166 | 22-187 | gi 5640160 |
|  | Cable | CblA[2] | 184 | 50/150 (33%) | 20-167 | 13-159 | gi 606843 |
| CsaC | CFA/I | CfaC | 869 | 800/868 (92%) | 16-883 | 2-869 | gi 2121079 |
|  | CS1 | CooC | 872 | 531/841 (63%) | 40-880 | 31-868 | gi 488736 |
|  | CS2 | CotC | 866 | 469/839 (55%) | 40-878 | 29-864 | gi 897728 |
|  | CS6 | CssD |  | 120/549 (21%) |  |  | P53513 |
|  |  | TsaC[1] | 895 | 260/867 (29%) | 42-872 | 25-882 | gi 5381204 |
|  |  | AtfC[3] | 843 | 111/491 (22%) | 211-670 | 207-665 | gi 1504107 |
|  |  | CaflA[4] | 833 | 100/511 (19%) | 209-685 | 205-661 | gi 3883097 |
| CsaE | CFA/I | CfaE | 360 | 268/361 (74%) | 2-362 | 1-360 | gi 2121080 |
|  | CS1 | CooD | 363 | 177/329 (59%) | 41-362 | 39-363 | gi 488737 |
|  | CS2 | CotD | 364 | 161/339 (47%) | 29-362 | 28-364 | gi 897729 |
|  |  | TsaD[1] | 359 | 90/303 (29%) | 71-361 | 79-358 | gi 5640162 |
|  |  | rfbF[5] | 187 | 19/66 (28%) | 146-211 | 55-114 | gi 48590 |

TABLE 3-continued

Similarity in AA sequences between ETEC CsaA-E proteins and other fimbrial proteins

| CS4 protein | Pili | Protein | #amino acids | Identities | region in CS4 proteins | region in compared protein | Gene no. |
| --- | --- | --- | --- | --- | --- | --- | --- |
| CsaD | CFA/I | CfaD | 265 | 90/101 (89%) | 9-109 | 49-149 | gi 145506 |
|  | CFA/I | CfaD | 144 | 90/101 (89%) | 9-104 | 49-144 | gi 145508 |
|  |  | RNS | 265 | 89/101 (88%) | 9-104 | 49-149 | gi 145512 |
|  |  | CSVR | 305 | 75/103 (72%) | 9-104 | 49-151 | gi 95726 |
|  | AAF/I | AGGR | 265 | 57/101 (56%) | 9-109 | 49-149 | gi 420983 |

[1] *Salmonella typhi*
[2] *Burkholderia cepacia*
[3] *Proteus mirabilis* outer membrane usher protein
[4] *Yersinia pestis* F1 capsule anchoring protein
[5] *Yersinia enterocolitica*

Localization of the csa Operon in Strain E11881A

In order to identify the location of the csa operon, total genomic DNA was isolated from strain E11881A, and was subjected to agarose gel electrophoresis. The electrophoresis results indicated the presence of 3 plasmids: a large plasmid located above the chromosomal band, and two smaller plasmids located under the chromosomal DNA band. The plasmids and the chromosomal bands were gel eluted and tested by PCR assays for the presence of the csa operon, using primers CS44/CS45 for amplification of the csaB gene. These results indicated that the csa operon was located on the large plasmid. The location of the LT gene was detected by PCR assays using primers LTA162/LTB895 (for amplification of a 708 bp DNA), indicating the LT encoding genes were located on the large plasmid. Amplification of the gyrA gene, using primers GYRA347/GYRA1147 (for amplification of a 748 bp DNA) indicated a chromosomal location. In order to see whether strain E11881A contained a complete csaD gene, PCR assays were performed with primers that are homologous to csaD' gene (CS4D2 and CS4D3), and with primer CS4D1 that is homologous to cfaD and rns genes (CSD41/CSD43). The results indicates that strain E11881A does not contain the complete cfaD gene. Primers CS4D2/CS4D3 amplified the expected 476 DNA fragment, while primers CS4D1/CS4D3, did not amplified an expected 646 bp. Strains E11881E, DS9-1H10407, and C91f, contained the complete gene.

Expression of the CS4 Pili in DH5α and CVD1204

Figure 2B:
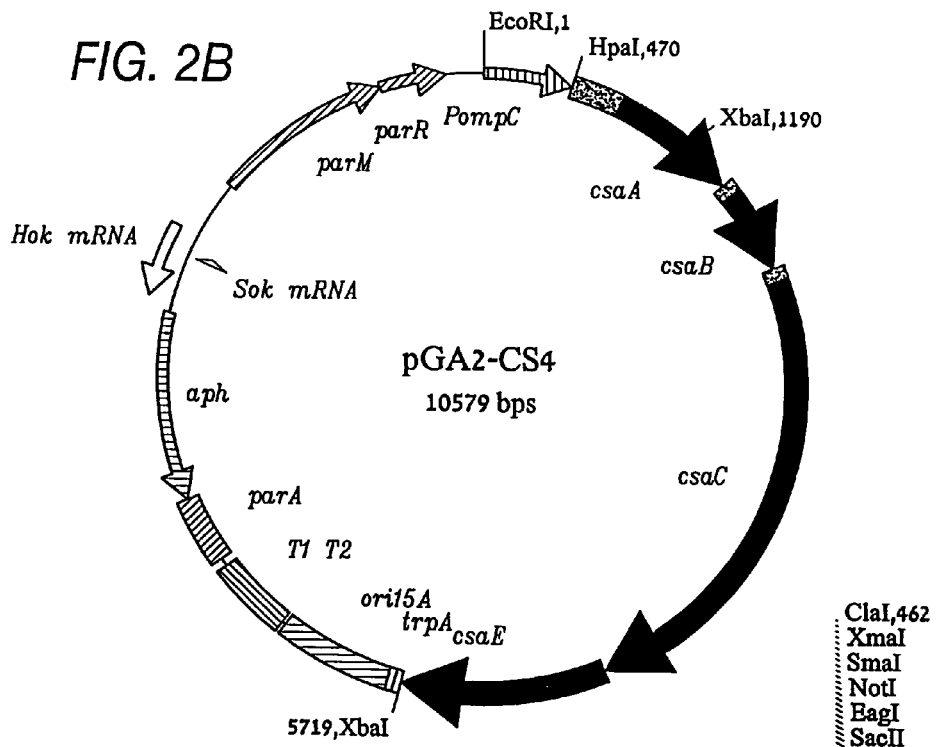
FIG. 2B, Plasmid pGA2-CS4 that contained the cloned CS4 fimbriae encoding genes, csaA, csaB, csaC, and csaE.
Figure 2A:
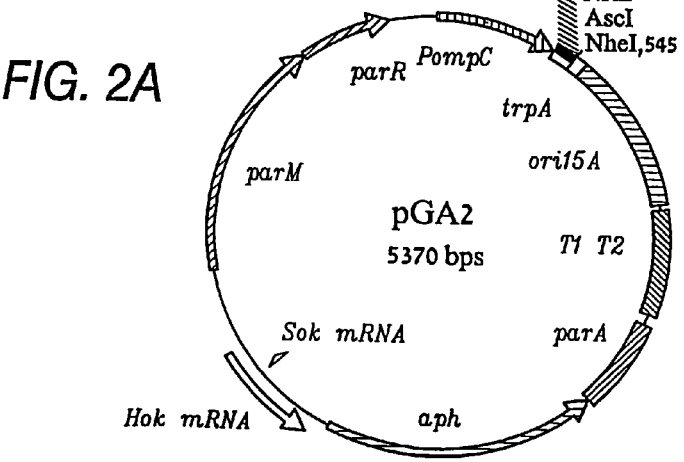
FIG. 2. The CS4 fimbriae expression plasmid. Schematic description of the stabilized plasmid pGA2, (FIG. 2A), that is maintained with 15 copies per cell, and contained the hok-sok post-segregational killing system, the parA and parM plasmid partitioning system; the aph allele for resistance to kanamycin, and multiple cloning sites.

The expression of the CS4 fimbriae was detected following cloning of 5281 bp of the csa operon in vector pGA2, to construct the plasmid pGA2-CS4, (FIG. 2B). The cloned csa operon contained 240 bp of the promoter region up stream the ATG codon for csaA gene, the csaA, csaB, csaC and csaE genes. The csa operon was cloned downstream of the ompC promoter, which is osmotically regulated. Plasmid pGA2-CS4 was transferred to *E. coli* DH5α and *Shigella* CVD1204 strains. CS4 fimbriae production by strains DH5α (pGA2-CS4) and CVD1204 (pGA2-CS4) strains was detected by agglutination assays using rabbit serum against the CS4 fimbriae and western blot of cell extracts. Western blot results indicates that the cloned csaABCE gene cluster encodes for a 17 kDa band that correspond to the CS4 fimbriae.

Antibody Response of Guinea-Pigs to CVD1204 (pGA2-CS4)

To test whether the cloned csa operon could induce an immune response against ETEC-CS4, guinea pigs were immunized by two intranasal administrations of $2 \times 10^9$ live CVD1204 (pGA2-CS4), and as control with CVD1204 (pGA2) strain. The immunized animals were tested for bacterial agglutination, immunoblotting, and inhibition of hemagglutination and adherence of CS4 expressing strains to Caco-2 cells.

Agglutination Assays

Bacterial agglutination assays done with immune guinea pigs indicated that immunized animals with CVD1204 (pGA2-CS4) developed antibodies that agglutinates all CS4 producing strains, and especially the high fimbriae producing strains DS 9-1, DH5α(pGA2-CS4) and CVD1204(pGA2-CS4), as described in Table 4. The end point of serum dilution that agglutinates DS 9-1 and DH5α(pGA2-CS4) strains is >1:100 and >1:1000, respectively. The control sera from animals immunized with CVD1204 (pGA2) strain, agglutinate CVD1204 strains. Bacterial agglutination assays using rabbit anti-CS4 antiserum were also performed and the data from these assays is presented in Table 5.

TABLE 4

Bacterial agglutination assays by rabbit anti CS4 antiserum

| Strain | NaCl mM | End point dilution of the antibody that result in bacterial agglutination | Induction factor |
| --- | --- | --- | --- |
| CVD1204(pGA2-CS4) | 0 | 1:400 |  |
|  | 50 | 1:800 | 2 |
|  | 150 | 1:1600 | 4 |
|  | 300 | 1:800 | 2 |
| CVD1204(pGA2) | 0 | <1:10 |  |
|  | 150 | <1:10 | none |

TABLE 5

Bacterial agglutination assays by immune guinea pigs serum

|  |  | Intensity of bacterial agglutination by immune guinea pigs sera[2] against: | |
| --- | --- | --- | --- |
| Tested strain[1] | Relevant phenotype | CVD1204 (pGA2-CS4) | CVD1204 (pGA2) |
| E11881A | CS4+ CS6+ | + | − |
| E11881E | CS4+ CS6+ | + | − |
| EII881C | CS4− CS6+ | − | − |
| E11881/G28 | CS4− CS6− | − | − |
| DS9-1 | CS4+ CS6+ | ++++ | − |

TABLE 5-continued

Bacterial agglutination assays by immune guinea pigs serum

| | | Intensity of bacterial agglutination by immune guinea pigs sera[2] against: | |
|---|---|---|---|
| Tested strain[1] | Relevant phenotype | CVD1204 (pGA2-CS4) | CVD1204 (pGA2) |
| DH5α(pGA2-CS4) | CS4+ | ++++ | − |
| DH5α | CS4− | − | − |
| CVD1204(pGA2-CS4) | CS4+ | ++++ | + |
| CVD1204 | CS4− | + | ++ |

[1]ETEC and *Shigella* strains were grown on CFA and TSA, guanine, Km plates, respectively; and resuspended to $OD_{600}$ nm of 5.
[2]The assays were performed with antibodies dilution of 1:10 and higher.

Immunoblotting Assays

The immunized guinea pigs were tested in immunoblotting experiments to bind to CS4 fimbriae proteins. The assays were performed by probing CS4 producing strains with the guinea pig immune serum and rabbit anti-CS4 serum. Cell extract were isolated from ETEC strains E11881A and DS 9-1, that grew on CFA plates at 37° C. and 22° C. (a condition that suppresses fimbriae production), from DH5α (pGA2-CS4) and CVD1204 (pGA2-CS4) strains that grew in LB broth in the presence of Km. The immunoblotting results showed that guinea pigs serum from CS4 immunized animals reacted with a 17 kDa band protein which is the CS4 fimbrial structural protein. ETEC strains produced a 17 kDa band at 37° C. but not at 22° C. *E. coli* and *Shigella* strains that contains the plasmid pGA2-CS4 produced 17 kDa protein bands, which was not produced in the corresponding untransformed cells.

Inhibition of Hemagglutination

ETEC strains that produce the CS4 fimbriae cause a mannose resistant agglutination of human red blood cells type A. The ability of ETEC-CS4 strains, DH5α, and a CVD1204 strain that contains the cloned CS4 encoding genes, were tested for hemagglutination. The results are presented in Table 6. The hemagglutination assays indicated that all CS4 pili producing strains caused hemagglutination. ETEC-CS4 strains demonstrate a more intense hemagglutination than strains expressing the cloned csa operon. Non CS4 producing strains did not caused any hemagglutination.

TABLE 6

Efficiency of bacterial induced hemagglutination

| Tested strains | Relevant phenotype | Hemagglutination |
|---|---|---|
| E11881A | CS4+ CS6+ | ++ |
| E11881E | CS4+ CS6+ | +++ |
| EII881C | CS4− CS6+ | − |
| DS 9-1 (37° C.*) | CS4+ CS6+ | ++++ |
| DS 9-1 (22° C.*) | CS4− | − |
| DH5α(pGA2-CS4) | CS4+ | + |
| DH5α | CS4− | − |
| CVD1204(pGA2-CS4) | CS4+ | + |
| CVD1204(pGA2) | CS4− | − |

*Temperature of growth.

The guinea pigs anti-CS4 antiserum was tested for inhibition of hemagglutination. ETEC-CS4 strains were incubated with various antibody dilutions prior to their addition to the red blood cells suspension. The results that are presented in Table 7 indicates that the guinea pigs anti-CS4 antibodies inhibits the hemagglutination, while the control immune serum against the *Shigella* has no effect on the ETEC-CS4 induced hemagglutination.

TABLE 7

Efficiency of inhibition of bacterial induced hemagglutination by guinea pigs anti-CS4 antibodies

| Tested strains | End point dilution of antibodies that inhibit bacterial induced hemagglutination. Antibodies were from guinea pigs immunized with: | |
|---|---|---|
| E11881A | 1:256 | <1:2 |
| DS 9-1 | 1:32 | <1:2 |

Inhibition of Adherence of ETEC-CS4 Strains to Caco 2 Cells

ETEC-CS4 producing strains have the ability to adhere to human carcinoma cell line Caco-2. The adhesion of ETEC strain DS 9-1 to the Caco-2 cells, and the effect of the guinea-pigs anti-CS4 antibodies on this adhesion were tested. The results indicate that ~10-100 bacteria adhere to the Caco-2 cells. As a control, the adhesion of DH5α bacteria was tested, and only very few bacteria were found to adhere. Preincubation of the ETEC DS 9-1 with guinea pigs anti-CS4 serum (1:10 dilutions), totally inhibit the adherence of the bacterial cells to the Caco-2 cells.

EXAMPLE 2

Construction of an Attenuated *S. typhi* Strain that Constitutively Expresses CS4

In order to change the expression of CS4 in pGA2-CS4 from osmotically regulated to constitutive, a strong promoter, e.g., $P_{tac}$, is used. The promoter $P_{tac}$ is constitutively active in *Salmonella* spp., as these organisms lack laqI. Accordingly, constitutive CS4-expressor derivatives of CVD 915 are constructed in the manner described below.

First, the ompC promoter is removed from the pGA2-CS4 construct and replaced with the $P_{tac}$ promoter, resulting in the creation of pGA2tac-CS4. After confirming the presence of the $P_{tac}$ promoter in pGA2tac-CS4, the construct is introduced into *S. typhi* strain CVD-915, using standard molecular biology techniques.

Constitutive expression of the CS4 antigen is assessed by the agglutination assay described in Example 1. Using wild-type *S. typhi* strain Ty2 as the positive control, and untransformed CVD-915 (CVD $915^-$) as the negative control, expression of the CS4 antigen is found to be strong, constitutive, and not regulated by changes in osmolarity.

EXAMPLE 3

Immune Response Against Constitutively Expressed CS4

Groups of ten 6 weeks old Balb/c mice are immunized intranasally with $1.0\times10^{10}$ cfu of strain CVD 915 with pGA2tac-CS4 (CVD $915^+$) or CVD 915 without pGA2tac-CS4 (CVD $915^-$). Mice are bled prior and 30 days after their immunization, and their serum is stored at −20° C. until use. Antibodies present in the serum against *S. typhi* LPS, H (flagella) and CS4 antigens are determined by ELISA. The results indicate that immunization with strain CVD $915^+$ elicits antibody levels against the CS4 antigen that are significantly higher than those obtained with strain CVD $915^-$. The immune responses against other *S. typhi* antigens (LPS and H) are similar between both immunized groups. The results demonstrate that the constitutive expression of the CS4 antigen enhances the immune response against this antigen without interfering with the immune response against other somatic *S. typhi* antigens.

EXAMPLE 4

Immune Response Against Constitutively Expressed CS4

The enterotoxic *E. coli* strain expressing the CS4 antigen (ETEC-CS4) from Example 1 is formulated into an immunogenic composition for nasal administration into a human subject (ETEC-CS4). Approximately $1.0 \times 10^{10}$ cfu of the recombinant bacteria ETEC-CS4 is nasally administered to a human subject. A booster is administered two weeks subsequent to the first administration. Blood is subsequently drawn from the subject and assayed for the presence of anti-ETEC-CS4 and anti-CS4 antibodies. Such antibodies are found in the blood sample.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of generating an immune response in a subject, comprising:
   administering an immunogenic composition to a subject, wherein said immunogenic composition comprises isolated CsaA comprising the amino acid sequence of SEQ ID NO:2, isolated CsaB comprising the amino acid sequence of SEQ ID NO:4, isolated CsaC comprising the amino acid sequence of SEQ ID NO:6, isolated CsaD comprising the amino acid sequence of SEQ ID NO:8 and isolated CsaE comprising the amino acid sequence of SEQ ID NO:10, and a carrier, thereby generating an immune response in a subject.

2. The method of claim 1, wherein the carrier is a composition comprising components suitable for parenteral administration.

3. The method of claim 2, wherein the carrier is a composition comprising components suitable for intranasal administration.

4. The method of claim 2, wherein the carrier is a composition comprising components suitable for intramuscular administration.

5. The method of claim 1, wherein the carrier is a composition comprising components suitable for enteric administration.

6. A method for generating an immune response in a vertebrate against enterotoxigenic *Escherichia coli* (ETEC), comprising administering an immunogenic composition to a vertebrate, wherein said immunogenic composition comprises isolated CsaA consisting of the amino acid sequence of SEQ ID NO:2, isolated CsaB consisting of the amino acid sequence of SEQ ID NO:4, isolated CsaC consisting of the amino acid sequence of SEQ ID NO:6, isolated CsaD consisting of the amino acid sequence of SEQ ID NO:8 and isolated CsaE consisting of the amino acid sequence of SEQ ID NO:10, and a carrier, thereby generating an immune response in a vertebrate against ETEC.

* * * * *